United States Patent
Dawson et al.

(10) Patent No.: US 10,093,939 B2
(45) Date of Patent: *Oct. 9, 2018

(54) CITRUS TRISTEZA VIRUS BASED VECTORS FOR FOREIGN GENE/S EXPRESSION

(71) Applicant: **University

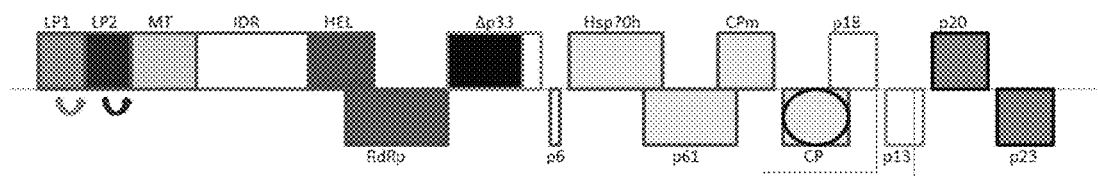
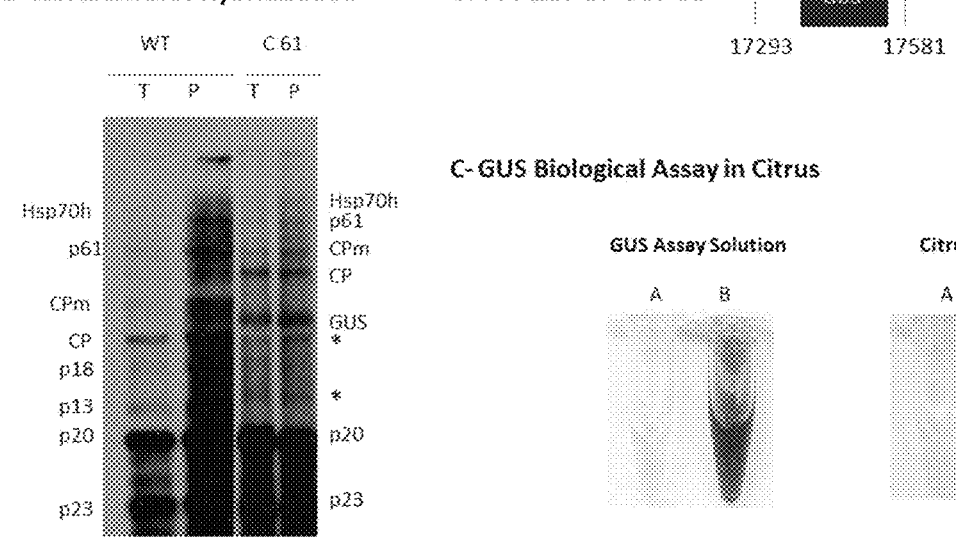
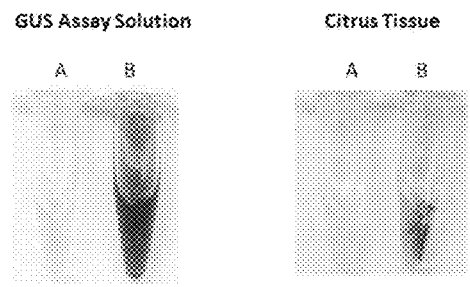
FIG. 2

A- CTV9RΔp33
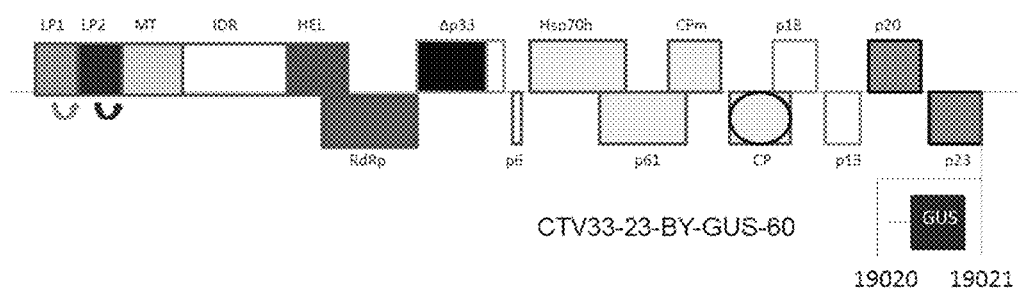
B- Northern Blot Hybridization
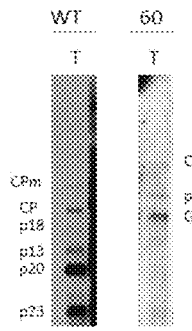
C- GUS Biological Activity
*N. benthamiana*
*Citrus macrophylla*
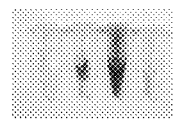
FIG. 6

Internal Ribosome Entry Site Strategy (IRES)

A-CTV9RΔp33

CTV33-23-ITEV-GFP-41;CTV33-23-I3XARC-GFP-43

B- Northern Blot Hybridization

CTV ΔCla 333R

A= CTVp333R-23-ITEV-GFP
B= CTVp333R-23-I3XARC-GFP
C= CTV ΔCla 333R
D= CTVp333R-23-B-GFP

FIG. 7

Poly-Peptide Fusion

A- CTV9RΔp33

FIG. 8

Replacement of p13 gene
A- CTV9RΔp33
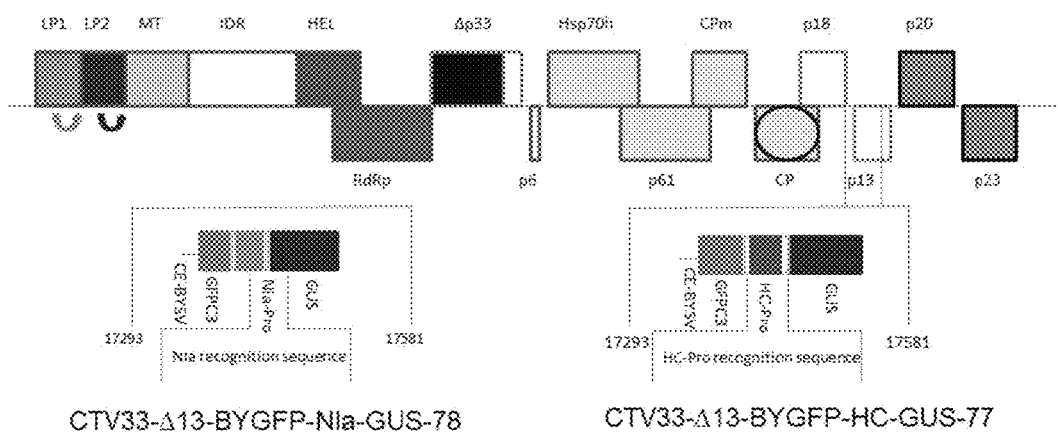
CTV33-Δ13-BYGFP-NIa-GUS-78    CTV33-Δ13-BYGFP-HC-GUS-77
B-Activity of Reporter genes
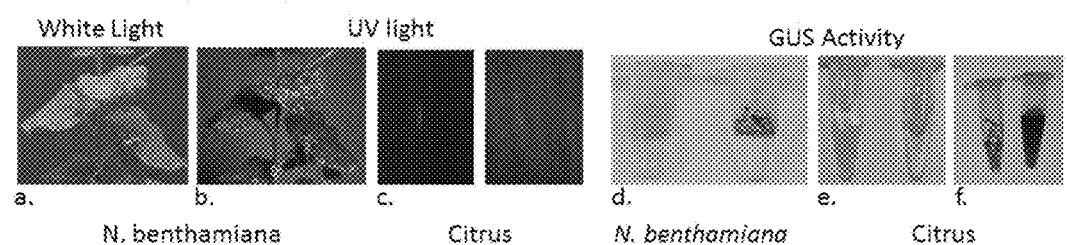
FIG. 11

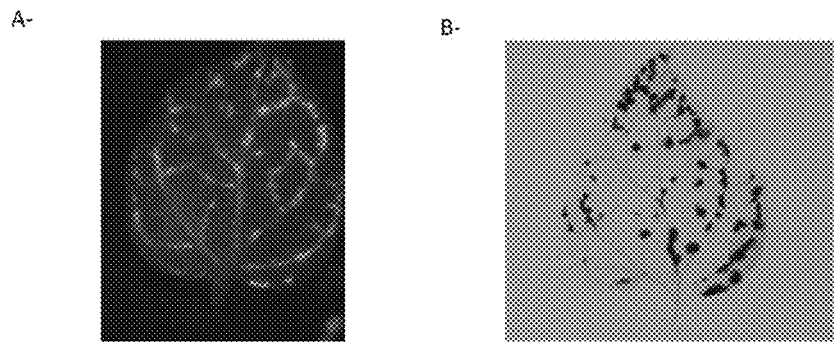
FIG. 12
Insertion between p23 and 3'NTR
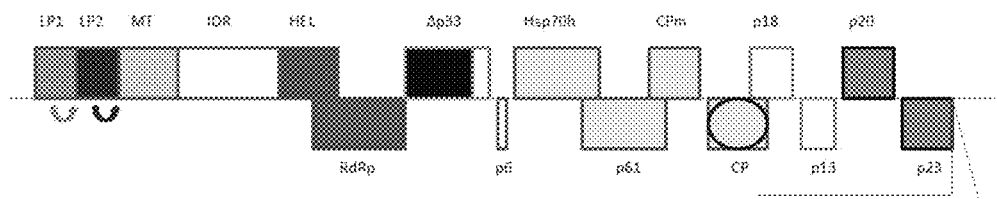
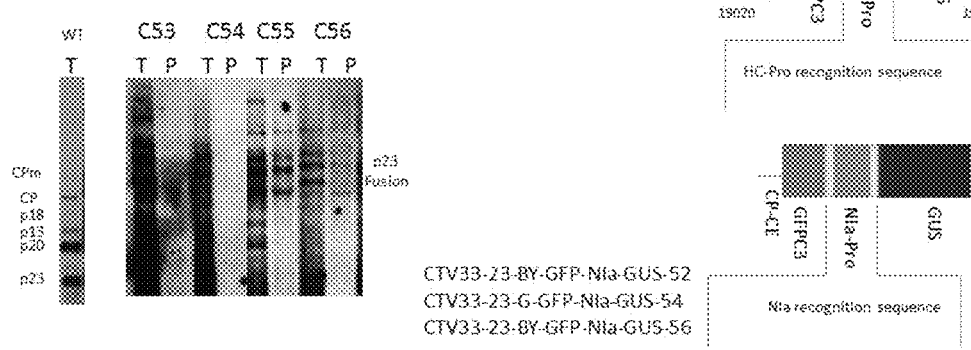
FIG. 13

*Example 6: Expression of multiple foreign genes simultaneously from different locations*

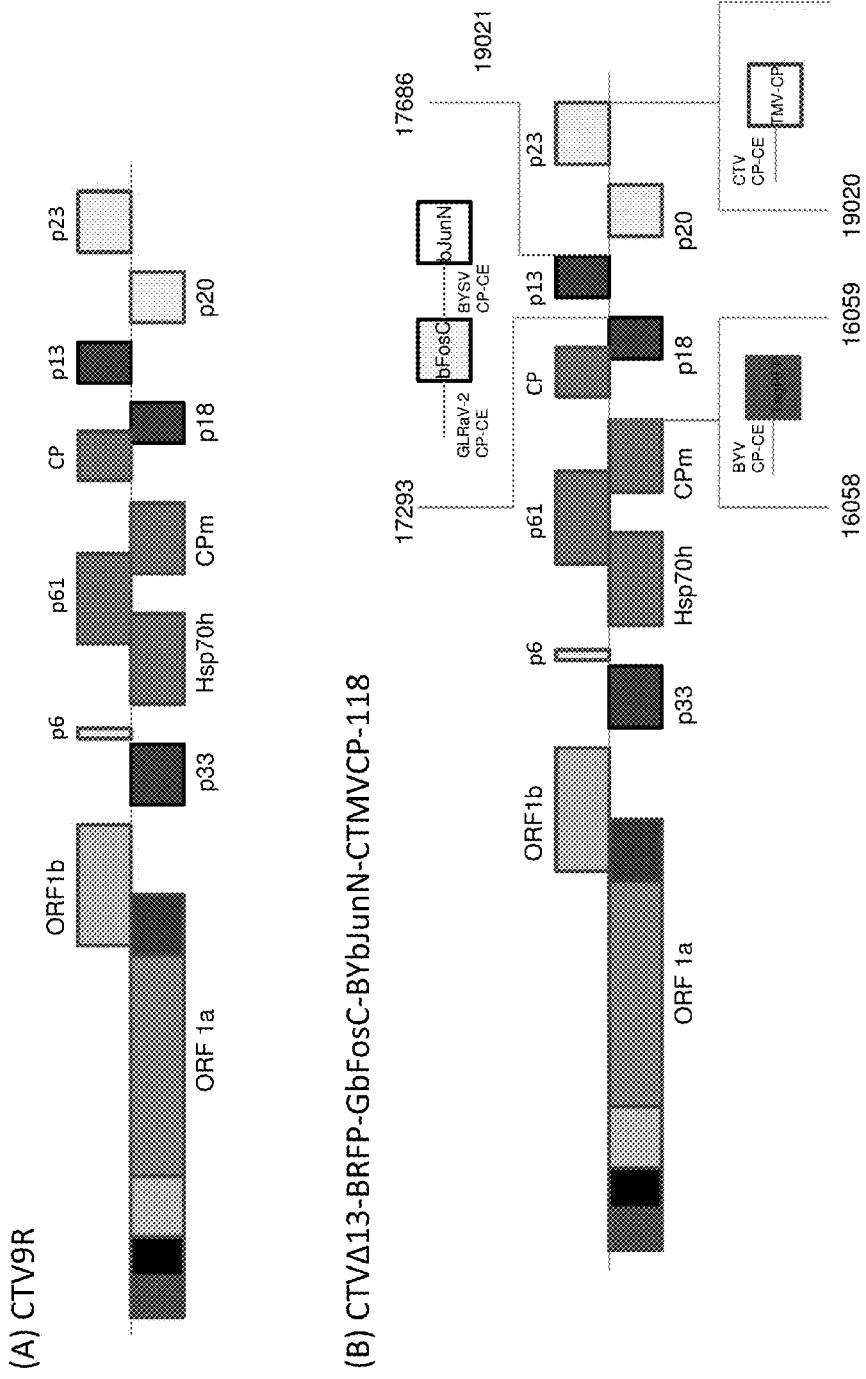

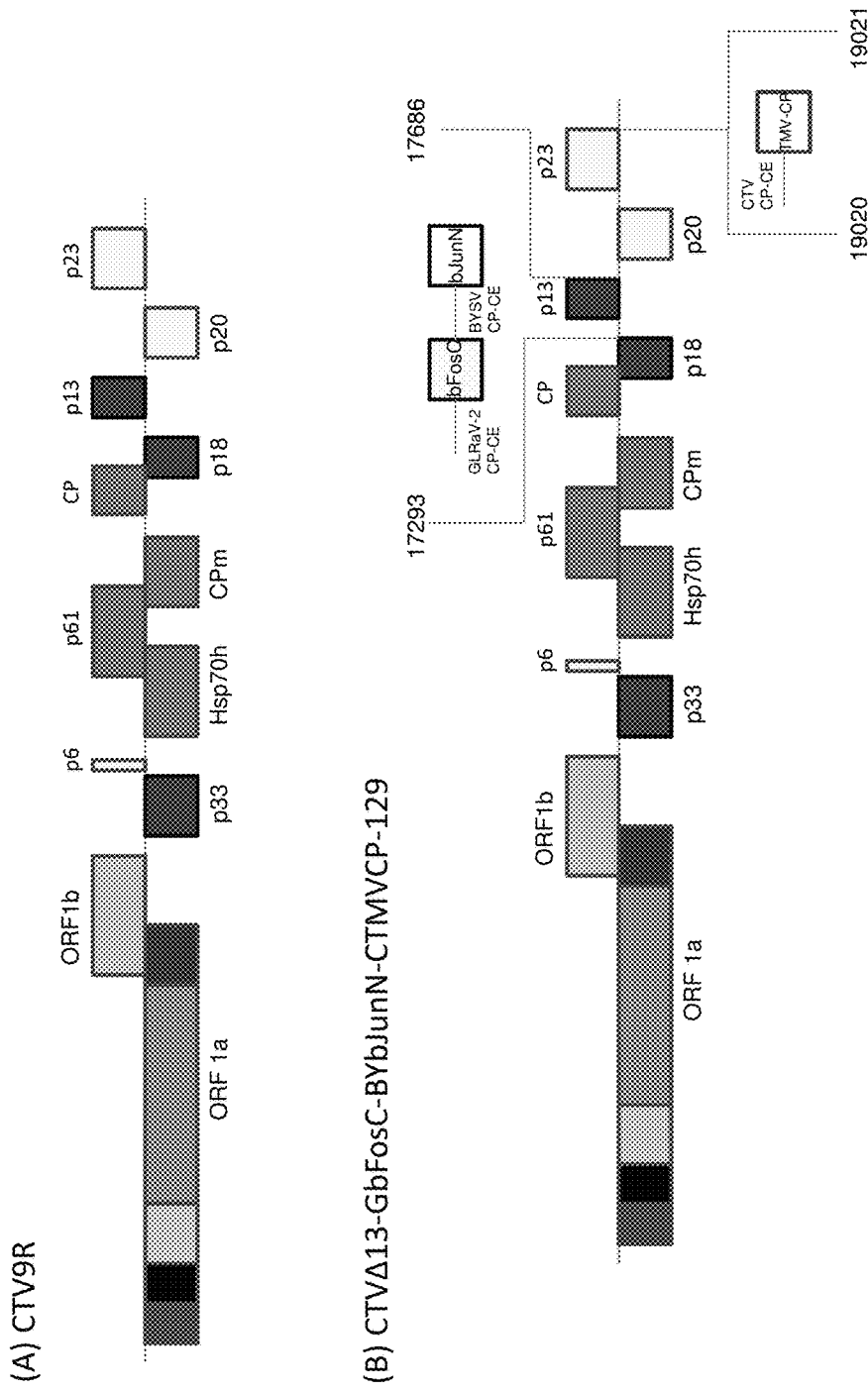
Fig. 21 3 gene vector
(A) CTV9R
(B) CTVΔ13-GbFosC-BYbJun

Fig. 22 3Gene vector (A) CTV9R

ORF 1a — ORF1b — p33 — p6 — Hsp70h — p61 — CPm — CP — p18 — p13 — p20 — p23

(B) CTV-BRFP-BYGFP-CTMVCP-117

ORF 1a — ORF1b — p33 — p6 — Hsp70h — p61 — CPm — CP — p18 — p13 — p20 — p23

16058 — BYV CP-CE
16059
17685
17686 — BYSV CP-CE — GFPC3
19020
19021 — CTV CP-CE — TMV-CP

Infiltrated into N. benthamiana (partial systemic movement visualised via GFP)

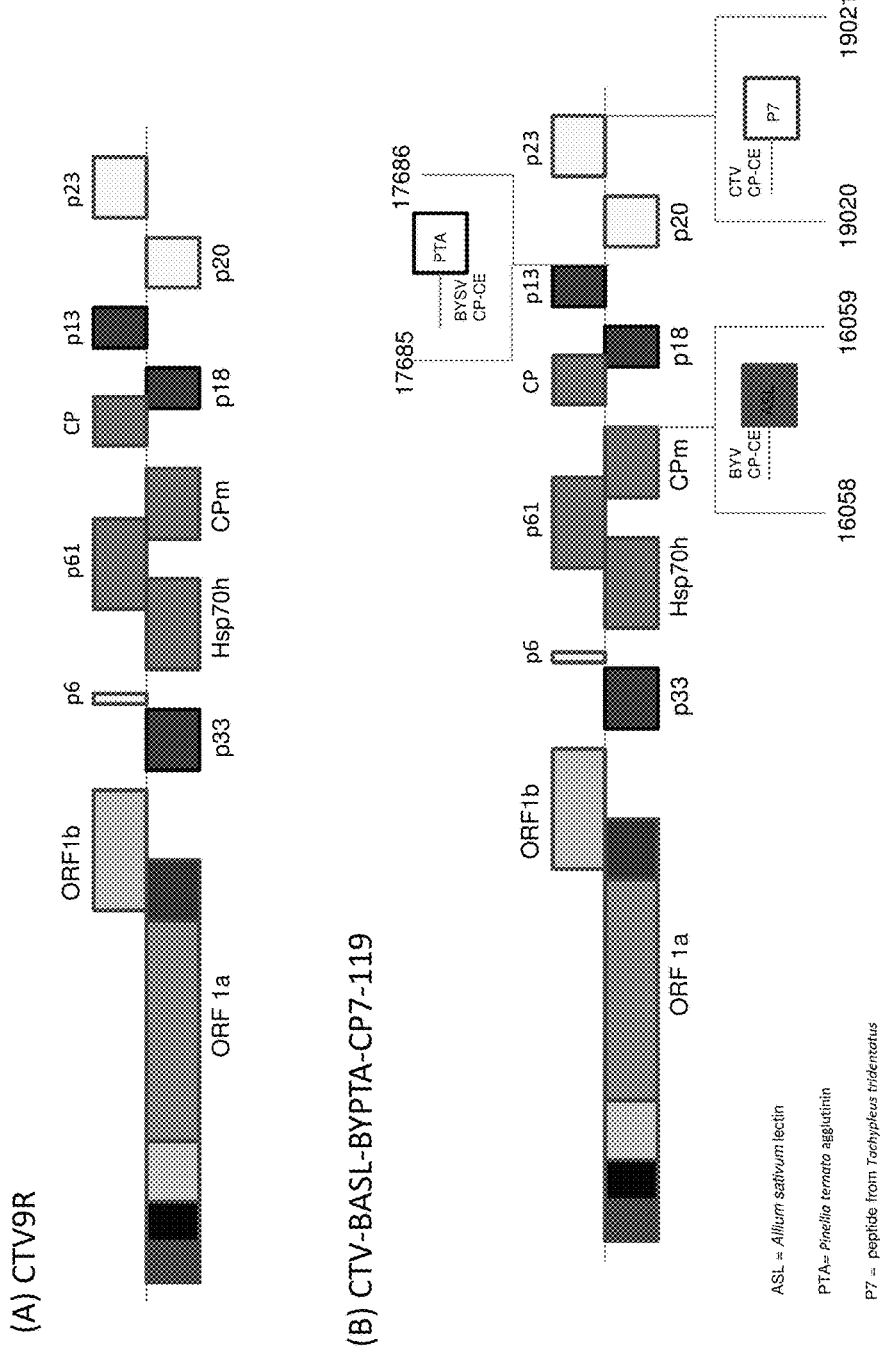

Fig. 24 3Gene vector (A) CTV9R (B) CTV-BASL-BYPTA-CP10-120

ASL = *Allium sativum* lectin
PTA = *Pinellia ternata* agglutinin
P10 = peptide from *Sus scorfa*

Infiltrated into N. benthamiana but no visual systemic movement observed in 24 plants

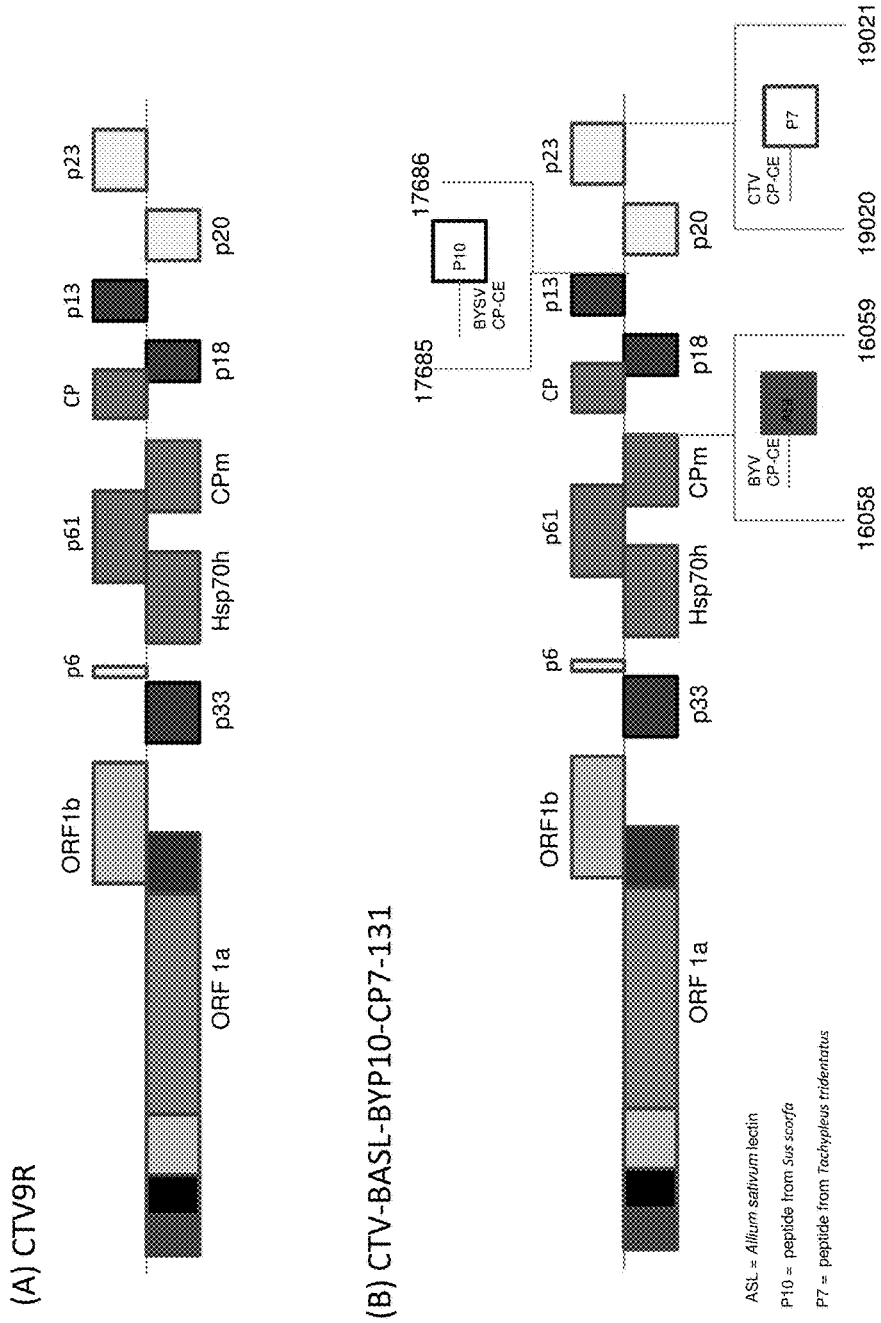
Fig. 25 3Gene vector

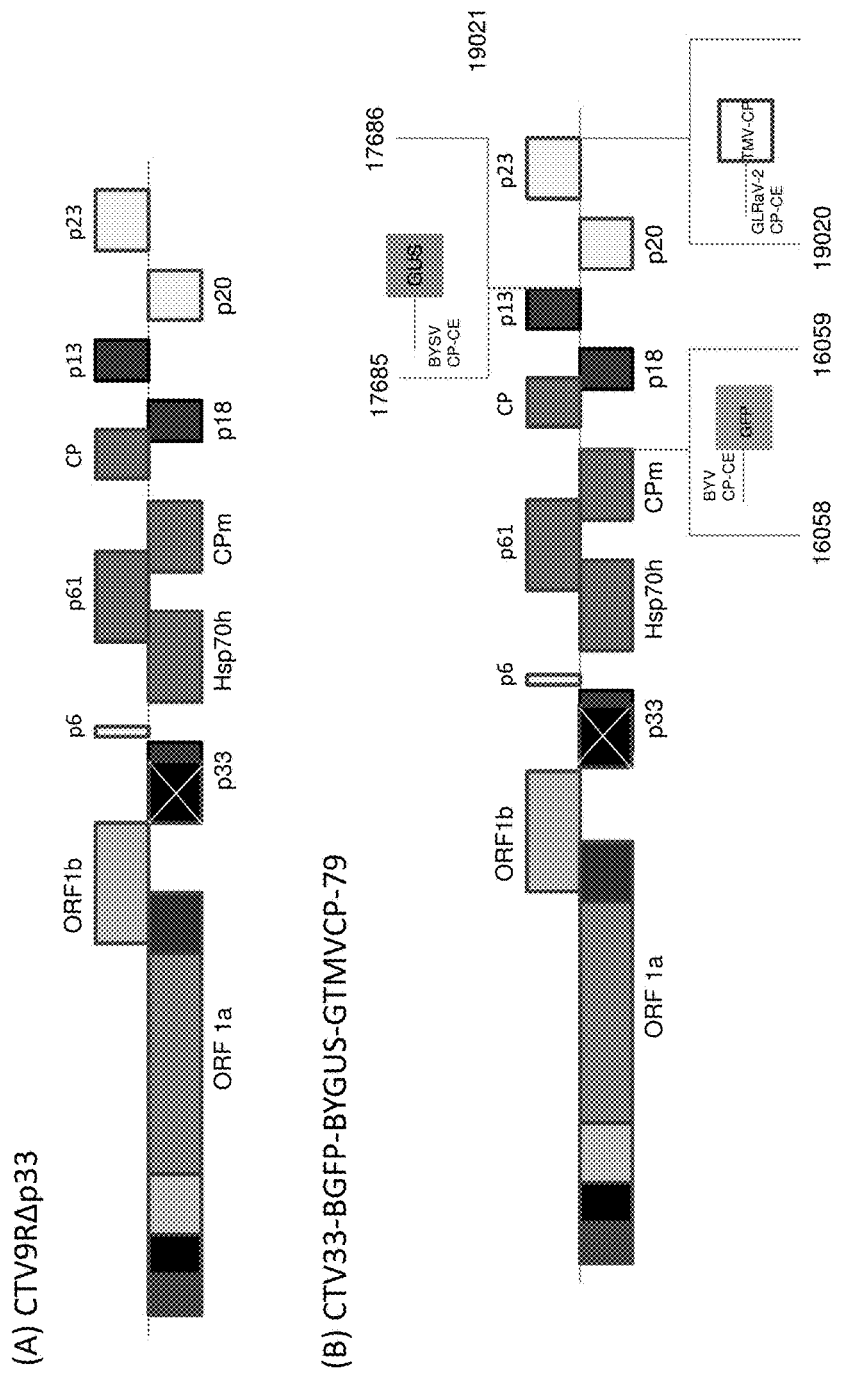
Fig. 26 3Gene vector

Fig. 27 3 Gene vector
(A) CTV9RΔp33
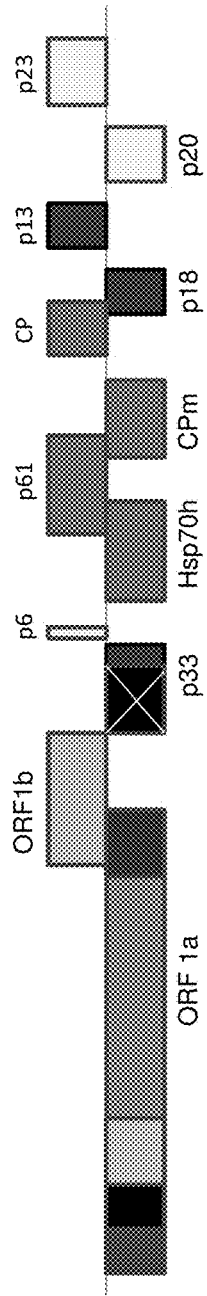
(B) CTV33-BGFP

Fig. 28 3Gene vector
(A) CTV9RΔp33
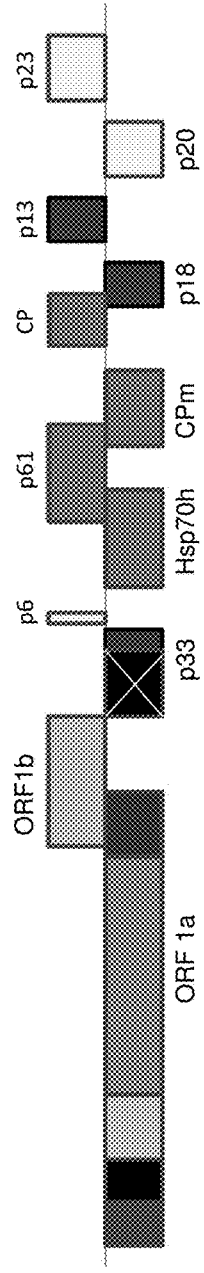
(B) CTV33-Δ13-BGFP-BY

CITRUS TRISTEZA VIRUS BASED VECTORS FOR FOREIGN GENE/S EXPRESSION

CROSS-REFERENCE TO RELATED APPLICATIONS

This application is related to U.S. Provisional Application No. 61/537,154 filed Sep. 21, 2011, to which priority is claimed under 35 USC 119 and which is incorporated herein by reference and is a continuation-in-part of U.S. Ser. No. 12/174,159 filed Jul. 16, 2008 which issued is U.S. Pat. No. 8,629,334 on Jan. 14, 2014.

SEQUENCE LISTING

The instant application contains a Sequence Listing which has been submitted in ASCII format via EFS-Web and is hereby incorporated by reference in its entirety. Said ASCII copy, created on Dec. 27, 2012, is named 10457204.txt and is 18,121 bytes in size.

BACKGROUND

The early development of viral vectors was aimed at the inexpensive production of high levels of specialty proteins that could be scaled up in the field. The first attempt at a plant viral vector utilized Cauliflower mosaic virus, a dsDNA virus (Brisson et al., 1984; Gronenborn et al., 1981). However, this vector was too unstable to be useful (Fütterer et al., 1990). The development of reverse genetics systems amenable for manipulation of RNA viruses made many more viruses candidates for vector development (Ahlquist et al., 1984).

Virus vectors are key ingredients in basic research and have great potential for commercial applications. Lack of stability of foreign inserts has been a major drawback for potential applications of virus vectors for commercial protein expression in field applications.

SUMMARY

The present disclosure is based on multiple studies testing the vector limits of using CTV to express foreign genes ranging from 806 to 3480 nucleotides in size. In one embodiment, gene cassettes were introduced into the CTV genome as replacement of the p13 gene. In other embodiments, a gene was inserted at different locations (e.g., p13-p20, p20-p23 and p23-3'NTR (non-translated region)). In another embodiment, a fusion to p23 and protease processing were tested. In alternative embodiments, genes were inserted behind IRES sequences to create bi-cistronic messages.

Twenty seven expression vectors have been created and tested in *Nicotinia benthamiana* protoplasts and plants. Remarkably, most of the newly developed vector constructs disclosed herein replicated, spread systemically in plants, and produced their foreign gene(s). The highest expressing vectors tested include the "add a gene" constructs having an insertion between the p13 and p20 genes or between the p23 gene and the 3'NTR. Similarly, the vectors with the inserted gene replacing the p13 gene effectively expressed different reporter genes. However, optimal expression of the reporter gene depended both on the size and location of the insertion. Optimal expression of smaller genes are from positions nearer the 3' terminus, whereas larger genes are optimally expressed from more internal positions.

Efficient expression of two genes simultaneously from the same vector has been accomplished in both *N. benthamiana* and *citrus*. The novel CTV constructs disclosed herein have genomes with unique elasticity capable of accommodating and expressing foreign gene/s by different strategies.

Engineering an effective vector requires a balance between different factors. The vector needs to be designed such that replication and systemic movement in the plant are reduced minimally while the level of expression of the foreign protein is maximal (Shivprasad et al., 1999). The final factor is the stability of the vector. In general, the vector's usefulness is directly correlated with its stability. Stability is a product of reduced recombination and increased competitiveness of the vector with the resulting recombinants that have lost part or all of the inserted sequences.

BRIEF DESCRIPTION OF DRAWINGS

FIG. 1. GFP replacement of p13 to produce CTV based expression vectors. (A) Schematic representation of CTV9RΔp33 (Boxes represent open reading frames with blue outline of boxes represent the replication gene block whereas the red outline represent the closterovirus conserved gene block (Karasev, 2000). The black circle and black boxes outline represent silencing suppressors (Lu et al., 2004). Gold box outline represent genes dispensible for the infection of some *citrus* genotypes (Tatineni et al., 2008). Filled black rectangle represents the deletion of the p33 controller elements and ORF (nts 10858-11660 Genebank Accession # AY170468) (Satyanarayana et al., 1999; 2000; 2003)). Arrows indicate the processing of the leader proteases of CTV, LP1 and LP2 are two tandem leader protease, MT (methyl transferase), Hel (Helicase), RdRp (RNA dependent RNA polymerase, 433 (deletion of the 33 kda protein sequence), p6 (6 kda protein), Hsp70h (heat shock protein 70 homologue), p61 (61 kda protein), CPm (minor coat protein), CP (major coat protein, inter cellular silencing suppressor), p18 (18 kda protein), p13 (13 kda protein), p20 (20 kda protein, inter/intra cellular silencing suppressor), p23 (23 kda protein, intracellular silencing suppressor) and modification to produce expression vectors CTV33-Δ13-BY-GFP-57 (C57), CTV33-Δ13-G-GFP-65 (C65), CTV33-Δ13-B-GFP-66 (C66) with the CP-CE of BYSV, GLRaV-2 and BYV driving GFP, respectively. (B) Northern blot analysis of wild type CTV (WT) and CTV based expression vector transfected to *N. benthamiana* protoplast (T) and passaged to a new set of protoplasts (P). (C) Representative sample of fluorescence in *N. benthamiana* infected with either of the three constructs CTV33-Δ13-BY-GFP-57, CTV33-Δ13-G-GFP-65, CTV33-Δ13-B-GFP-66 magnified under a fluorescent stereoscope. (D) Representative sample of fluorescence in the phloem of *citrus* bark pieces infected with constructs CTV33-Δ13-G-GFP-65 and CTV33-Δ13-B-GFP-66 with high (left) and low (right) magnification under a fluorescent stereoscope.

FIG. 2 GUS replacement of p13 to produce CTV based expression vectors. (A) Schematic representation of CTV9RΔp33 and its modification creating expression vector CTV33-Δ13-BY-GUS-61 in which the p13 and its controller element is replaced by GUS under the control of CP-CE of BYSV. (B) Northern blot hybridization analysis of wild type CTV (WT) and CTV based expression vector CTV33-Δ13-BY-GUS-61 (C61) transfected to *N. benthamiana* protoplast (T) and passaged to a new set of protoplasts (P). (C) Representative sample of GUS activity in the bark pieces of *citrus* trees infected with construct CTV33-Δ13-BY-GUS- 61 (right) and the GUS solution before fixing of the bark pieces (left) (A=Healthy control, B=infect).

FIG. 3 GFP insertion between p13 and p20 to produce CTV based expression vectors. (A) Schematic representation of CTV9RΔp33 and modification by inserting between p13 and p20 of GFP ORF under the control of BYSV creating expression vector CTV33-13-BY-GFP-69 (B) Northern blot hybridization analysis of transfected protoplast with the wild type virus (WT) and expression vector CTV33-13-BY-GFP-69 (C69) from transcripts (T) and their passages (P). Representative sample of fluorescence in *N. benthamiana* (C) and peeled bark phloem pieces of *C. macrophylla* (D) infected with CTV33-13-BY-GFP-69 magnified under a fluorescent stereoscope.

FIG. 4 GFP insertion between p20 and p23 to produce CTV based expression vectors. (A) Schematic representation of CTV9RΔp33 and its modification producing expression vector CTV33-20-B-GFP-49 and CTV33-20-BY-GFP-58, respectively. (B) Northern blot hybridization analysis of transfected protoplast with the wild type virus (WT) and expression vectors CTV33-20-B-GFP-49 (C49) and CTV33-20-BY-GFP-58 (C58) from transcripts (T) and their passages (P). (C) Flourescence under UV light of protoplast (right) and the leaf (left) showing lack of efficient movement of the vector. (D) Western blot analysis of the same gene inserted at different locations in the CTV genome. BCN5 (Folimonov et al., 2007) original CTV vector (contains GFP under BYV promoter between CPm and CP), constructs CTV33-23-BY-GFP-37 (C37, insertion of BYSV driving GFP behind p23), CTV33-20-BY-GFP-58 (C58, insertion of BYSV driving GFP between p20 and p23), CTV33-13-BY-GFP-69 (C69, insertion of BYSV driving GFP between p13 and p20), CTV33-Δ13-BY-GFP-57 (C57, replacement of p13 gene with BYSV CP-CE driving GFP) and CTV33-27-BY-GFP-63 (C63, Insertion of BYSV CP-CE driving GFP ORF between CPm and CP).

FIG. 5 GFP insertion between p23 and 3'NTR to produce CTV based expression vectors. (A) Schematic representation of CTV9RΔp33 and its modification by insertion of GFP behind p23 under control of CP-CE of BYSV, GLRaV-2 and BYV creating expression CTV33-23-BY-GFP-37 (C37), CTV33-23-G-GFP-40 (C40) and CTV33-23-B-GFP-42 (C42), respectively. (B) Northern blot hybridization analysis of transfected protoplast with the wild type virus (WT) and expression vectors CTV33-23-BY-GFP-37, CTV33-23-G-GFP-40 and CTV33-23-B-GFP-42 from transcripts (T) and their passages (P). (C) Representative sample of fluorescence in *N. benthamiana* infected with either of the three constructs CTV33-23-BY-GFP-37, CTV33-23-G-GFP-40 and CTV33-23-B-GFP-42 magnified under a fluorescent stereoscope. (D) Representative sample of fluorescence in the phloem tissue of *Citrus macropylla* infected with constructs CTV33-23-BY-GFP-37 and CTV33-23-G-GFP-40.

FIG. 6 GUS insertion between p23 and 3'NTR insertion between p23 and 3'NTR to produce CTV based expression vectors. (A) Schematic representation of CTV9RΔp33 and modification by insertion of GUS ORF under control of BYSV CP-CE between p23 and 3'NTR creating expression vector CTV33-23-BY-GUS-60 (C60). (B) Northern blot hybridization analysis of transfected protoplast with the wild type virus (WT) and expression vectors CTV33-23-BY-GUS-60 from transcripts (T). (C) Enzymatic activity of the GUS protein in *N. benthamiana* tissue and *citrus* phloem bark pieces (Blue color indicate infected plant and colorless tissue and solution indicate healthy control and GUS solution subject to the same treatment.

FIG. 7 GFP inserted behind IRES sequences to create CTV based expression vectors. (A) Schematic representation of CTV9RΔp33 and CTVΔCla 333R and their modification behind p23 creating expression vectors CTV33-23-ITEV-GFP-41; CTV33-23-I3×ARC-GFP-43 represent the TEV 5'NTR IRES and 3×ARC-1 IRES, respectively and CTVp333R-23-ITEV-GFP; CTVp333R-23-I3×ARC-GFP representing the TEV 5'NTR IRES and 3×ARC-1 IRES, respectively. (B) 1—Northern blot hybridization analysis from tranfected *N. benthamiana* protoplast with wild type virus (WT), CTV33-23-ITEV-GFP-41 (C41) and CTV33-23-I3×ARC-GFP-43 (C43); T=RNA isolated from transcript transfected protoplast and P=RNA isolated from virion transfected protoplast isolated from RNA transfected protoplast. 2-Northern blot hybridization analysis from protoplast transfected with CTVp333R-23-ITEV-GFP (Lane A); CTVp333R-23-I3×ARC-GFP (lane B), CTVp333R (lane C) and CTVp333R-23-B-GFP (BYV CP-CE driving the expression of GFP behind p23) (Lane D).

Figure 8:
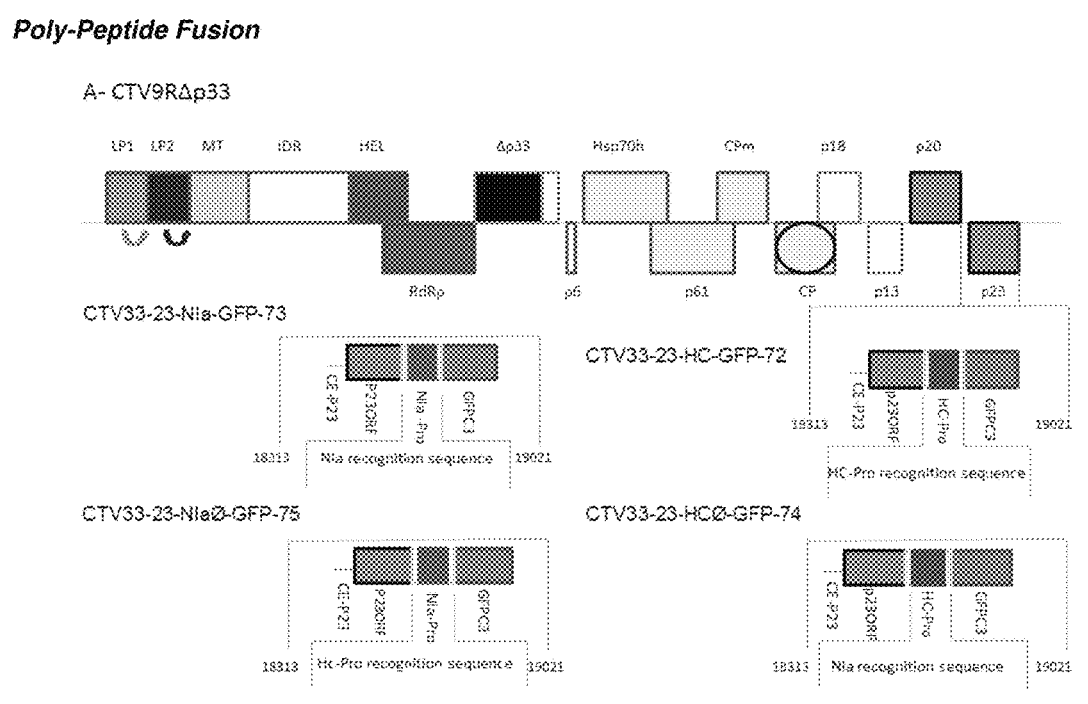

FIG. 8 GFP and a protease fused to p23 to create CTV based expression vectors. (A) Schematic representation of CTV9RΔp33 and the modifications by fusing two TEV proteases (NIa and HC-Pro) and their recognition sequences to create expression vectors CTV33-23-HC-GFP-72, CTV33-23-NIa-GFP-73, CTV33-23-HCØ-GFP-74 and CTV33-23-NIaØ-GFP-75.

FIG. 9 Comparison of Florescence in *N. benthamiana*. (A) Comparison of fluoresce in infiltrated leaves of representative samples of constructs CTV33-23-HC-GFP-72, CTV33-23-NIa-GFP-73, CTV33-23-HCØ-GFP-74 and CTV33-23-NIaØ-GFP-75 (GFP fused) and CTV33-23-BY-GFP-37, CTV33-23-G-GFP-40 and CTV33-23-B-GFP-42 (free GFP) under hand held UV light (Right) and the same leaves under white light (left). (B) Comparison on whole plant level between representative samples of constructs CTV33-23-HC-GFP-72 and CTV33-23-NIa-GFP-73 (fused GFP) and CTV33-23-BY-GFP-37, CTV33-23-G-GFP-40 and CTV33-23-B-GFP-42 (GFP under its own controller element behind p23 (Free GFP)) under hand held UV light (Right) and same plants under white light (Left). (C) Comparison between the abaxial (Lower) and adaxial (upper) leaf surfaces of the same representative leaf sample of constructs CTV33-23-HC-GFP-72 and CTV33-23-NIa-GFP-73 under hand held UV light (Right) and white light (Left).

FIG. 10 Western blot analysis of different expression vectors infiltrated into *N. benthamiana* leaves using GFP antibody. A=CTV9RΔp33GFP (GFP inserted under the BYV CP-CE controller element between CPm and CP (produces free GFP) (Tatineni et al., 2008)), B=CTV33-23-BY-GFP-HC-GUS-51, C=CTV33-23-G-GFP-NIa-GUS-54, D=Empty well; E=CTV33-Δ13-BY-GFP-NIa-GUS-78, F=CTV33-23-HC-GFP-72, G=CTV33-23-NIa-GFP-73.

FIG. 11 Hybrid gene (GFP/Protease/GUS fusion) replacement of p13 to create expression vectors. (A) Schematic representation of CTV9R Δ p33 and its modification to create expression vectors CTV33-Δ13-BYGFP-HC-GUS-77 and CTV33-Δ13-BYGFP-NIa-GUS-78 with the two fusion genes under the control of BYSV CP-CE with TEV HC-Pro and NIa spanned by their proteolysis recognition sequence separating GFP and GUS, respectively. (B) Activity of the reporter genes in *N. benthamiana* and *Citrus macrophylla*. (a.) Representative sample of *N. benthamiana* plant infected with either CTV33-Δ13-BYGFP-HC-GUS-77 or CTV33-Δ13-BYGFP-NIa-GUS-78 *N. benthamiana* under white light and (b.) the same plant under UV light (c.) Two pictures of peeled phloem bark pieces of *C. macro-*

*phylla* infected with construct CTV33-Δ13-BYGFP-NIa-GUS-78 under a flourescent stereoscope (d.) Representative sample of GUS activity in systemic *N. benthamiana* leaves, control leaf (Left) and infected leaf (right) (e.) Peeled bark phloem pieces and GUS solution of healthy *C. macrophylla* plant (f.) Peeled bark phloem pieces of *C. macrophylla* plant infected with construct CTV33-Δ13-BYGFP-NIa-GUS-78.

FIG. 12 Stability of Constructs in *N. benthamiana*. (A) Upper leaf from Agro-inoculated *N. benthamiana* plants carrying the binary vector CTV33-Δ13-BYGFP-HC-GUS-77 (GFP/HC-Pro/GUS) pictured under fluorescent microscope. (B) The same leaf was tested for GUS activity indicating almost perfect overlap between the two reporter genes.

FIG. 13 Hybrid gene (GFP/Protease/GUS fusion) between p23 and 3'NTR to create expression vectors. (A) Schematic representation of CTV9R Δ p33 and its modification to produce expression vectors CTV33-23-BY-GFP-HC-GUS-51 and CTV33-23-BY-GFP-NIa-GUS-52 has the BYSV CP-CE driving the hybrid genes that contain HC-Pro and NIa proteases respectively; CTV33-23-G-GFP-HC-GUS-53 (C53) and CTV33-23-G-GFP-NIa-GUS-54 (C54) are GLRaV-2 driven fusion genes that contain the HC-Pro and NIa proteases, respectively; CTV33-23-BY-GFP-HC-GUS-55 (C55) and CTV33-23-BY-GFP-NIa-GUS-56 (C56) are BYV driven fusion genes that contain HC-Pro and NIa proteases, respectively. (B) Northern blot hybridization analysis of transfected protoplast with wild type virus (WT), C53, C54, C55 and C56 constructs.

FIG. 14 Activity of reporter genes generated by insertion of the Hybrid gene (GFP/Protease/GUS fusion) behind p23. (A) Activity of the reporter genes in *N. benthamiana*. plants (a.) Representative sample of *N. benthamiana* plant infected with CTV33-23-BY-GFP-HC-GUS-51, CTV33-23-G-GFP-HC-GUS-53, CTV33-23-BY-GFP-NIa-GUS-52 or CTV33-23-G-GFP-NIa-GUS-54 under white light and (b.) the same plant under hand held UV light (c.) Representative sample of GUS activity in infected systemic *N. benthamiana* leaves and control leaves (tubes 1 &2 represent the solution before fixing and tissues in fixing solution, respectively from healthy leaves whereas 3&4 represent the solution and tissues from infected leaves, respectively, G tube is the GUS assay buffer (B.) Activity of reporter G genes in *C. macrophylla* (a.) Picture of peeled phloem bark pieces of *C. macrophylla* infected with construct CTV33-23-BY-GFP-HC-GUS-51 under a flourescent stereoscope (b.) Peeled bark phloem pieces GUS activity in infected and healthy *C. macrophylla* plants (tubes 1 &2 represent the solution and tissues in fixing solution from healthy leaves whereas 3&4 represent the solution and tissues from infected leaves, respectively.

FIG. 15 Bimolecular Flouresence complementation (BiFC) prove of concept. (A) Schematic representation of CTVΔ Cla 333R (Gowda et al., 2001, Satyanarayana et al., 2003) replicon and its modification to create expression replicons: (a.) Insertion of both BiFC genes between p23 and 3'NTR giving rise to CTVp333R-23-BYbJunN-GbFosC and the controls with one gene behind p23, CTVp333R-23-BYbJunN(b.) or CTVp333R-23-GbFosC(c.). (B) Northern blot hybridization analysis of transfected protoplast with CTVp333R-23-BYbJunN-GbFosC (Lane a.), CTVp333R-23-BYbJunN (Lane c.) and CTVp333R-23-GbFosC (Lane b.). (C) Flouresence of a transfected protoplast when pictured under a stereoscope (Upper) or a laser scanning confocal microscope (lower) indicating the flouresence from the nucleus.

FIG. 16 BiFC gene replacement of p13 to produce CTV based expression vectors. (A) Schematic representation of CTV9RΔp33 and modification to produce vector CTV33-Δ13-BYbJunN-GbFosC-76 and the control vectors CTV33-23-G-bFosC-98 and CTV33-23-BY-bJunN-97 (insertion behind p23 nts 19020-19021). (B) Representative sample of *N. benthamiana* fluorescence in systemically infected plants.

FIG. 17 CTV based expression vector built to simultaneously express two genes from two controller elements. (A) Schematic representation of CTV9RΔp33 and its modification to produce expression vectors CTV33-23-BYbJunN-GbFosC-59 and CTV33-Δ13-BYbJunN-23-GbFosC-67. (B) Northern blot hybridization analysis of the RNA transfected protoplast with the wild type virus (WT,T), two clones of CTV33-Δ13-BYbJunN-23-GbFosC-67 (C67,T1 and T2) and two clones of CTV33-23-BY-bJunN-Gb-FosC-59 (C59, T3 and T4) probed with 3'NTR+p23 (Satyanarayana et al., 1999). (C) Flourescence of *N. benthamiana* plant parts under a flourescent stereo microscope (CTV33-23-BY-bJunN-Gb-FosC-59=a., b., c. and d; CTV33-Δ13-BYbJunN-23-Gb-FosC-67=e.) (a.) bud (b.) Corolla, (c.) systemic leaves, (d.) peeled bark phloem pieces and (e.) infiltrated leaf FIG. 18 CTV based expression vector built to simultaneously express two genes from two controller elements. (A) Schematic representation of CTV9RΔp33 and its modification to produce expression vectors CTV33-Δ13-BYGUS-23-GGFP-71. (B) Northern blot hybridization analysis of the RNA transfected protoplast with the wild type virus (WT) and the CTV33-Δ13-BYGUS-23-GGFP-71 (C71) expression vector probed with 3'NTR+p23 (Satyanarayana et al., 1999). (C) Biological activity of reporter genes in *N. benthamiana* and *Citrus*. *N. benthamiana* plant under white light (a.) and hand held UV light (b.). (c.) GUS activity from healthy (tube 1 (assay solution) &2 (tissue) and infected *N. benthamiana* (tube 3 (assay solution) and tube 4 (tissue). (d.) Peeled bark phloem pieces under flourescent microscope and (e.) GUS assay activity in *citrus* similar to (c.)

FIG. 19 Western blot analysis of the different constructs in *citrus* to evaluate the expression of GFP and GUS. (A) GFP and CP antibody used to determine the level of expression of GFP relative to CP in *citrus* 708 plant infected with Δp33CTV9R (Tatineni et al., 2008), 1808 plant infected with BCN5 (Folimonov et al., 2007), 1916 plant infected with CTV33-23-G-GFP-40, 1874 plant infected with CTV33-23-BY-GFP-37, 1934, 1935, 1937 infected with CTV33-13-BY-GFP-69, 1931 and 1939 infected with construct CTV33-Δ13-G-GFP-65 and CTV33-Δ13-B-GFP-66, respectively. (B) GUS and CP antibody used to determine the level of expression of GUS relative to CP in *citrus* 2084, 2085, 2086, 2087 plants infected with construct CTV33-Δ13-BYGUS-61, 2132 plant infected with construct CTV33-23-BYGUS-60, 2096 plant infected with expression vector CTV33-Δ13-BYGFP-NIa-GUS-78, E=empty well and buffer=−iveC.

FIG. 20 CTV based expression vector built to simultaneously express four genes from four controller elements. (A) A schematic representation of CTV9R. (B) Modification of CTV9R to create expression vector CTVΔ13-BRFP-Gb-FosC-BYbJunN-CTMVCP-118 which expresses 4 genes from different locations within the CTV genome. The first gene is the red flourescent protein gene (tagRFP) expressed from between the minor and major coat proteins under the control of the Beet yellows virus (BYV) coat protein controller element (CP-CE), the second and third genes are the truncated mammalian transcription factors bFos and bJun fused to the C and N terminus of EYFP (Hu et al., 2002) under the control of Grape vine leaf roll associated virus-2 (GLRaV-2) and Beet yellow stunt virus (BYSV) CP-CE respectively replacing the p13 gene and the fourth gene is the CP of TMV expressed from behind p23 under the control of the duplicated major CP-CE of CTV.

FIG. 21 CTV based expression vector built to simultaneously express three genes from three controller elements. (A) A schematic representation of CTV9R. (B) Modification of CTV9R to create expression vector CTVΔ13-GbFosC-BYbJunN-CTMVCP-129 which expresses 3 genes from different locations within the CTV genome. The first and second genes are the truncated mammalian transcription factors bFos and bJun fused to the C and N terminus of EYFP (Hu et al., 2002) under the control of Grape vine leaf roll associated virus-2 (GLRaV-2) and Beet yellow stunt virus (BYSV) CP-CE respectively replacing the p13 gene and the fourth gene is the CP of TMV expressed from behind p23 under the control of the duplicated major CP-CE of CTV.

FIG. 22 CTV based expression vector built to simultaneously express three genes from three controller elements. (A) A schematic representation of CTV9R. (B) Modification of CTV9R to create expression vector CTV-BRFP-BYGFP-CTMVCP-117 which expresses 3 genes from different locations within the CTV genome. The first gene is the red flourescent protein gene (tagRFP) expressed from between the minor and major coat proteins under the control of the Beet yellows virus (BYV) coat protein controller element (CP-CE), the second gene is the Green fluorescent protein (GFPC3) under the control of Beet yellow stunt virus (BYSV) CP-CE inserted between p13-p20 gene and the third gene is the CP of TMV expressed from behind p23 under the control of the duplicated major CP-CE of CTV.

FIG. 23 CTV based expression vector built to simultaneously express three genes from three controller elements. (A) A schematic representation of CTV9R. (B) Modification of CTV9R to create expression vector CTV-BASL-BYPTA-CP7-119 which expresses 3 genes from different locations within the CTV genome. The first gene is a lectin from Allium sativum (ASL) expressed from between the minor and major coat proteins under the control of the Beet yellows virus (BYV) coat protein controller element (CP-CE), the second gene is an agglutinin from Pinellia ternata (PTA) under the control of Beet yellow stunt virus (BYSV) CP-CE inserted between p13-p20 gene and the third gene is an antimicrobial peptide from Tachypleus tridentatus (P7) expressed from behind p23 under the control of the duplicated major CP-CE of CTV.

FIG. 24 CTV based expression vector built to simultaneously express three genes from three controller elements. (A) A schematic representation of CTV9R. (B) Modification of CTV9R to create expression vector CTV-BASL-BYPTA-CP10-120 which expresses 3 genes from different locations within the CTV genome. The first gene is a lectin from Allium sativum (ASL) expressed from between the minor and major coat proteins under the control of the Beet yellows virus (BYV) coat protein controller element (CP-CE), the second gene is an agglutinin from Pinellia ternata (PTA) under the control of Beet yellow stunt virus (BYSV) CP-CE inserted between p13-p20 gene and the third gene is an antimicrobial peptide from Sus scorfa (P10) expressed from behind p23 under the control of the duplicated major CP-CE of CTV.

FIG. 25 CTV based expression vector built to simultaneously express three genes from three controller elements. (A) A schematic representation of CTV9R. (B) Modification of CTV9R to create expression vector CTV-BASL-BYP10-CP7-131 which expresses 3 genes from different locations within the CTV genome. The first gene is a lectin from Allium sativum (ASL) expressed from between the minor and major coat proteins under the control of the Beet yellows virus (BYV) coat protein controller element (CP-CE), the second gene is an antimicrobial peptide from Sus scorfa (P10) under the control of Beet yellow stunt virus (BYSV) CP-CE inserted between p13-p20 gene and the third gene is a second antimicrobial peptide from Tachypleus tridentatus (P7) expressed from behind p23 under the control of the duplicated major CP-CE of CTV.

FIG. 26 CTV based expression vector built to simultaneously express three genes from three controller elements. (A) A schematic representation of CTV9RΔp33. (B) Modification of CTV9R Δp33 to create expression vector CTV33-BGFP-BYGUS-GTMVCP-79 which expresses 3 genes from different locations within the CTV genome. The first gene is a green flourescent protein expressed from between the minor and major coat proteins under the control of the Beet yellows virus (BYV) coat protein controller element (CP-CE), the second gene is a β-Glucuronidase (GUS) gene from Eisherchia coli under the control of Beet yellow stunt virus (BYSV) CP-CE inserted between p13-p20 gene and the third gene is the CP of TMV expressed from behind p23 under the control of Grape vine leaf roll associated virus-2 (GLRaV-2) CP-CE.

FIG. 27 CTV based expression vector built to simultaneously express four genes from four controller elements. (A) A schematic representation of CTV9RΔp33. (B) Modification of CTV9RΔp33 to create expression vector CTV33-BGFP-GbFosC-BYbJunN-81 which expresses 3 genes from different locations within the CTV genome. The first gene is the green flourescent protein gene (GFPC3) expressed from between the minor and major coat proteins under the control of the Beet yellows virus (BYV) coat protein controller element (CP-CE), the second and third genes are the truncated mammalian transcription factors bFos and bJun fused to the C and N terminus of EYFP (Hu et al., 2002) under the control of Grape vine leaf roll associated virus-2 (GLRaV-2) and Beet yellow stunt virus (BYSV) CP-CE respectively. The bFosC gene is inserted behind p23 gene.

FIG. 28 CTV based expression vector built to simultaneously express four genes from four controller elements. (A) A schematic representation of CTV9RΔp33. (B) Modification of CTV9RΔp33 to create expression vector CTV33-Δ13-BGFP-BYbJunN-GbFosC-82 which expresses 3 genes from different locations within the CTV genome. The first gene is the green flourescent protein gene (GFPC3) expressed from between the minor and major coat proteins under the control of the Beet yellows virus (BYV) coat protein controller element (CP-CE), the second gene is the truncated mammalian transcription factor bJun to the N terminus of EYFP (bJunN) (Hu et al., 2002) under the control of Beet yellow stunt virus (BYSV) CP-Cereplacing the p13 gene of CTV and the third gene is the truncated mammalian transcription factor bFos fused to the C-terminus of EYFP (bFosC) under the control of Grape vine leaf roll associated virus-2 (GLRaV-2) CP-CE inserted behind p23.

FIG. 29 Negative staining Electron microscopy pictures from leaf dips of infiltrated N. benthamiana Leaves. (A) Leaf dips from infiltrated N. benthamiana leaves with construct CTV33-BGFP-BYGUS-GTMVCP-79 reveals the formation of CTV vector virions and TMV pseudo virions indicating the expression of the TMV coat protein gene. (B) Leaf dip from Infiltrated N. benthamiana leaves with construct CTV33-Δ13-BGFP-BYbJunN-GbFosC-82 reveals the formation of virions.

DETAILED DESCRIPTION

Figure 1:
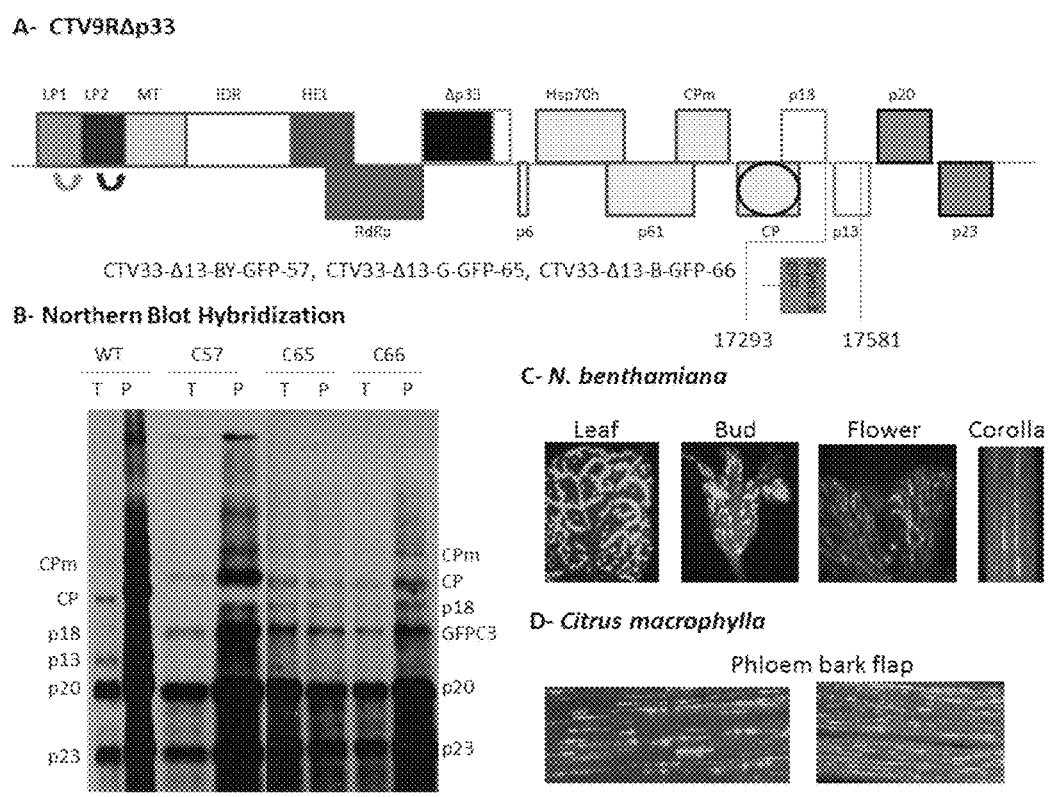

The early development of viral vectors was aimed at the inexpensive production of high levels of specialty proteins that could be scaled up in the field. The first attempt at a plant viral vector utilized Cauliflower mosaic virus, a dsDNA virus (Brisson et al., 1984; Gronenborn et al., 1981). However, this vector was too unstable to be useful (Fütterer et al., 1990). The development of reverse genetics systems amenable for manipulation of RNA viruses made many more viruses candidates for vector development (Ahlquist et al., 1984). There was considerable controversy concerning the value of RNA viruses for vectors (Siegel, 1983, 1985; Van Vluten-Dotting, 1983 Van Vluten-Dotting et al., 1985). It was argued that the lack of proof-reading of the RNA virus replicases would result in too rapid sequence drift to maintain foreign sequences during replication. However, subsequent development and use of RNA virus-based vectors demonstrated that this concern was overstated.

Ongoing efforts have been underway to create virus-based vectors for *citrus* trees based on *Citrus tristeza* virus (CTV). CTV has the largest reported RNA of a plant virus of approximately 20 kb (Karasev et al., 1995; Pappu et al., 1994). It has two conserved gene blocks associated with replication and virion formation (Karasev, 2000). The replication gene block occupies the 5' half of the genome. Its proteins are expressed from the genomic RNA via a poly protein strategy with a +1 ribosomal frame shift to occasionally express the RNA dependent RNA polymerase (Karasev et al., 1995). The filamentous virions of CTV are encapsidated by two coat proteins, with the major coat protein (CP) encapsidating about 97% of the virion and the 5' ~700 nts encapsidated by the minor coat protein (CPm) (Satyanarayana et al., 2004). Virion formation is a complex process requiring two proteins (Hsp70h and p61) in addition to the coat proteins (Satyanarayana et al., 2000, 2004; Tatineni et al., 2010). These four genes as well as the 6 remaining genes are differentially expressed via a nested set of 3' co-terminal sub genomic (sg) RNAs (Hilf et al., 1995). Upstream of each ORF there is a controller element (CE) that determines the transcription level (Gowda et al., 2001). Levels of transcription are also associated with the +1 transcription start site (Ayllón et al., 2003), the presence of a non-translated region upstream of the ORF (Gowda et al., 2001), and the closeness of the ORF to the 3' terminus (Satyanarayana et al., 1999).

The first generations of CTV vector examined three different strategies that were fusion of the CP gene, insertion of an extra gene, and replacement of the p13 ORF (Folimonov et al., 2007). Replacement of the p13 ORF and fusion to the coat protein ORF did not result in effective vectors, but the addition of an extra gene resulted in viable vectors that produce relative large amounts of foreign gene and were stable in *citrus* trees for years. However, the first efforts in designing vectors based on CTV examined only a few of the many possibilities for expressing foreign genes in this large virus. In this work, the inventors attempted to examine the limitations of CTV to be manipulated into a vector. The inventors examined whether the virus allowed insertions in different positions within the genome and which resulted in maximal expression with different sizes of inserts. The inventors also examined whether different fusion strategies with different viral genes are viable and whether multiple foreign genes can be expressed. The CTV constructs disclosed herein are amazingly tolerant to manipulation at several positions within the genome giving a multitude of different vector strategies that are viable.

Once *citrus* is infected with a CTV vector containing a foreign gene, it is easy to move the vector to other *citrus* trees by grafting. However, a limitation of the CTV vector system is the difficulty of initially getting *citrus* infected with new vector constructs. Directly inoculating *citrus* from the cDNA clones, either by agro-inoculation, particle bombardment, or mechanical inoculation with RNA transcripts is extremely difficult and unpredictable (Gowda et al., 2005; Satyanarayana et al., 2001). An alternative has been to inoculate with virions purified from *Nicotiana benthamiana* protoplasts (Folimonov et al., 2007; Robertson et al., 2005; Satyanarayana et al., 2001; Tatineni et al., 2008). However, infection of only approximately 0.01-0.1% of protoplasts with in vitro transcribed RNA has been achieved (Satyanarayana et al., 2001). Yet, since virions are much more infectious to the protoplasts than RNA (Navas-Castillo et al., 1997), the inventors were able to amplify the infection by sequential passage in protoplasts (Folimonov et al., 2007; Robertson et al., 2005; Satyanarayana et al., 2001; Tatineni et al., 2008). Although workable, this is an extremely difficult system. The inventors are now able to agro-inoculate *N. benthaminana* plants that result in systemic infection. This result allows analysis of the vector constructs more quickly in these plants and provides copious amounts of recombinant virus for inoculation of *citrus*. Thus, the inventors report the activity of the different vector constructs in *N. benthamina* and *Citrus*.

According to one embodiment, the invention pertains to a CTV viral vector engineered to comprise a gene cassette comprising a polynucleotide encoding a heterologous polypeptide. The gene cassette is located at a targeted position on the CTV genome. In a more specific embodiment, the CTV viral vector is engineered such that the gene cassette is positioned at CTV genome regions p13-p20, p20-p23 or p23-3'NTR. In other embodiments, the CTV viral vector is engineered to include multiple genes at one or multiple positions. It is shown herein that CTV viral vectors can successfully be engineered to include up to 3 or at least 4 genes that are expressible by the vector, while maintaining the proper function and infectivity of the vector.

In related embodiments, the invention pertains to a plant that includes at least one cell transfected with the CTV viral vector engineered to comprise a gene cassette comprising a polynucleotide encoding a heterologous polypeptide, the CTV viral vector engineered such that one or more gene cassettes are positioned at CTV genome regions p13-p20, p20-p23 or p23-3'NTR. Other related embodiments pertain to methods of expressing at least one heterologous polypeptide in a plant by infecting the plant with the specified vector.

In a further embodiment, the invention is directed to a CTV viral vector engineered to comprise at least one gene cassette that includes a polynucleotide encoding a heterologous polypeptide, wherein the CTV viral vector engineered such that the gene cassette is inserted in place of the CTV p13 gene. In related embodiments, the invention pertains to a plant that includes at least one cell transfected with the CTV viral vector or to methods of expressing the heterologous polypeptide in a plant by infecting the plant with the specified vector.

In another embodiment, the invention relates to a CTV viral vector engineered to comprise at least one gene cassette comprising a polynucleotide encoding heterologous polypeptide and IRES sequence conjugated thereto. In related embodiments, the invention pertains to a plant that includes at least one cell transfected with the CTV viral vector or to methods of expressing the heterologous polypeptide in a plant by infecting the plant with the specified vector.

In further embodiments, the invention relates to a CTV viral vector engineered to comprise a gene cassette comprising a polynucleotide sequence with continuous amino acid codons extending from the p23 ORF encoding a first heterologous polypeptide (protease) with cleavage sites on each side plus a second heterologous polypeptide. In related embodiments, the invention pertains to a plant that includes at least one cell transfected with the CTV viral vector or to methods of expressing the heterologous polypeptide in a plant by infecting the plant with the specified vector.

In further embodiments, the polynucleotide further comprises a sequence encoding a first control element upstream of said first heterologous polypeptide, a second sequence encoding a protease with cleavage sites engineered on each side, and a sequence encoding a second heterologous polypeptide.

According to another embodiment, the invention is directed to CTV viral vector engineered to comprise a first gene cassette comprising a polynucleotide sequence encoding a first heterologous polypeptide and a first controller element upstream of said first heterologous polypeptide encoding sequence; and a second gene cassette comprising a polynucleotide sequence encoding a second heterologous polypeptide and a second control element upstream of said second heterologous polypeptide encoding sequence. Optionally, the CTV viral vector further comprises a third gene cassette comprising a polynucleotide sequence encoding a third heterologous polypeptide and a third controller element upstream of said third heterologous polypeptide encoding sequence; and a fourth gene cassette comprising a polynucleotide sequence encoding a fourth heterologous polypeptide and a fourth controller element upstream of said fourth heterologous polypeptide encoding sequence. Those skilled in the art will appreciate that additional gene cassettes can be added to the vector so long as function and infectivity of the vector is maintained. In related embodiments, the invention pertains to a plant that includes at least one cell transfected with the CTV viral vector or to methods of expressing the heterologous polypeptide in a plant by infecting the plant with the specified vector.

Examples of controller elements (CE) useful in accordance with the teachings herein include but are not limited to controller elements homologous to CTV or heterologous control elements. Heterologous controller elements include, but are not limited to, coat protein controller elements (CP-CEs) of three closteroviruses: Beet yellows virus (BYV) (94 nts from 13547-13640 Genbank accession # AF190581) (Peremyslov et al., 1999), Beet yellow stunt virus (BYSV) (101 nts from 8516-8616 Genbank accession # U51931) (Karasev et al., 1996) and Grape vine leaf roll associated virus-2 (GLRaV-2) (198 nts from 9454-9651 Genbank accession # DQ286725). It will be evident to those skilled in the art, in view of the teachings herein, that other controller elements may be implemented, and in particular control elements having strong promoter like activity.

These and other embodiments are further described below and encompassed within the appended claims.

Materials and Methods for Examples 1-7 Below

Plasmids Construction pCTV9RΔp33 and pCTVΔCla 333R (Gowda et al., 2001; Satyanarayana et al., 1999, 2000, 2003; Tatineni et al., 2008) were used as base plasmids for developing all expression vectors that were used in the protoplast reverse genetics system. The numbering of the nucleotides (nts) is based on the full length T36 clone (Genbank Accession # AY170468) (Satyanarayana et al., 1999, 2003). CTVp333R-23-ITEV-GFP and CTVp333R-23-I3×ARC-GFP (FIG. 7A) were created by fusing 5' non translated region (NTR) of Tobacco etch virus (TEV) (nucleotides (nts) 2-144 Genbank accession # DQ986288) (Carrasco et al., 2007) and 3×ARC-1 (Active ribosome complementary sequence) (Akergenov et al., 2004) behind the p23 stop codon (between nts19020-19021 in full length T36 clone) using overlap extension polymerase chain reaction (PCR) (Horton et al., 1989). For creating expression vectors by gene addition and/or substitution at different locations, heterologous controller elements (CE) were selected from coat protein controller elements (CP-CEs) of three closteroviruses: Beet yellows virus (BYV) (94 nts from 13547-13640 Genbank accession # AF190581) (Peremyslov et al., 1999), Beet yellow stunt virus (BYSV) (101 nts from 8516-8616 Genbank accession # U51931) (Karasev et al., 1996) and Grape vine leaf roll associated virus-2 (GLRaV-2) (198 nts from 9454-9651 Genbank accession # DQ286725) to drive the ORFs for cycle 3 GFP (GFP) (Chalife et al., 1994; Crameri et al., 1996), β-Glucuronidase (GUS) ORF of Eisherchia coli, bFosYC155-238 (bFosC), bJunYN1-154 (bJunN). CTVp333R-23-BYbJunN-GbFosC, CTVp333R-23-BYb-JunN, CTVp333R-23-GbFosC (FIG. 15A) were created by overlap extension PCR from plasmids pBiFC-bFosYC155 and pBiFC-bJunYN155 (Hu et al., 2002) and CTV9R (Satyanarayana et al., 1999; 2003). Since two NotI sites exist within the bimolecular fluorescence genes (BiFC), the overlap extension PCR products were digested partially by NotI restriction endonuclease. The PCR products were introduced into a StuI and NotI digested pCTVΔCla 333R (FIGS. 7A & 3-15A).

The expression vectors created in pCTV9RΔp33 were introduced into the CTV genome by digesting the plasmid with PstI (nts 17208-17213) and NotI or StuI (introduced behind 19,293 the final CTV nucleotide). Overlap extension PCR (Horton et al., 1989) was used to introduce the appropriate genes at the different locations. Replacement of the p13 gene was done by deletion of nts 17293-17581 in the p13 ORF and (CE) by overlap extension PCR (FIGS. 3-1A, 3-2A, 3-11A, 3-16A, 3-17A & 3-18A). Similarly, insertion between p13 and p20 (nts #17685-17686) (FIG. 3A), p20-p23 (nts #18312-18313) (FIG. 4A) and p23-3'NTR (nts #19020-19021) (FIGS. 3-5A, 3-6A, 3-13A, 3-16A, 3-17A & 3-18A) were done by overlap extension PCR. A hybrid gene created by fusing the GFP ORF (Chalife et al., 1994; Crameri et al., 1996) and GUS ORF separated by the HC-Pro protease motif (nts 1966-2411 Genbank accession # M11458)(Allison et al., 1985; Carrington et al., 1989) and its recognition sequence fused to the N terminus of GUS (ATGAAAACTTACAATGTTGGAGGGATG (SEQ ID NO: 1) (nts 2412-2438 Genbank accession # M11458) (Allison et al., 1985; Carrington et al., 1989) (Amino acid sequence (A.A.) MKTYNVG,GM) (SEQ ID NO: 2) (arrow indicate processing site) and C terminus of GFP (ATGAAGACCTATAACGTAGGTGGCATG) (SEQ ID NO: 3) was created and inserted behind p23 (FIG. 13A) or as replacement of p13 (FIG. 3-11A) under different controller elements. A similar hybrid gene was created by using the NIa protease motif of TEV (nts 6270-6980 Genbank accession # M11458) (Allison et al., 1985) and its recognition sequence (GAGAATCTTTATTTTCAGAGT (SEQ ID NO: 4) (nts 8499-8519 Genbank accession # M11458) (A.A. ENLY-FQ↓S) (SEQ ID NO: 5) (arrow indicate processing site) (Carrington and Dougherty, 1988) at C terminus of GFP and GAAAACCTATACTTCCAATCG (SEQ ID NO: 6) at N terminus of GUS). The redundancy of the amino acid genetic code was used to eliminate complete duplication of the nucleotide sequences of the recognition motifs. A similar strategy was used to create a hybrid gene between p23 ORF and GFP ORF in construct CTV33-23-HC-GFP-72 and CTV33-23-Nla-GFP-73 (FIG. 8). Switching the recognition motif of the proteases generated control vectors CTV33-23-HCØ-GFP-74 and CTV33-23-NlaØ-GFP-75 (FIG. 8).

The binary plasmid pCAMBIACTV9R (Gowda et al., 2005) was modified to eliminate the p33 gene by deleting nts 10858-11660 (Satyanarayana et al., 2000; Tatineni et al., 2008) and introducing a SwaI site behind the ribozyme engineered based on subterranean clover mottle virusoid (Turpen et al., 1993). PCR products amplified from the expression vectors in the pCTV9RΔp33 back-bone were introduced into the modified binary plasmid pCAMBIACTV9RΔp33 digested with PstI (Forward primer C-749) and SwaI (Reverse primer C-1894). When introducing the bimolecular fluorescence complementation (BiFC) genes into constructs CTV33-23-BYbJunN-GbFosC-59 (FIG. 17), CTV33-Δ13-BYbJunN-23-GbFosC-67 (FIG. 17), CTV33-Δ13-BYbJunN-GbFosC-76 (FIG. 16), CTV33-23-GbFosC-98 (FIG. 16) and CTV33-23-BYbJunN-97 (FIG. 16) a primer was used switching the PstI to the compatible NsiI (primer C-2085) for ease of cloning (the bFosC gene sequence contains one PstI site while the bJunN gene sequence contains two PstI sites). Preliminary screening for the right inserts in the different expression vectors was done by restriction digestion using the appropriate enzymes. The junctions where the foreign genes were introduced into the expression vectors were confirmed by sequencing at the Interdisciplinary Center for Biotechnology Research (ICBR) (University of Florida, Gainesville, Fla.). All primers are listed in Table 1-1.

TABLE 1-1

List of primers used in building expression vector

| Primer name | Sequence 5'-3'* | SEQ ID NO: | Description* |
|---|---|---|---|
| C-749 | AGT CCT CGA GAA CCA CTT AGT TGT TTA GCT ATC | 7 | 3'end of p18 (CTV T36 clones nts # 17121-17145) with an added XhoI site before nt #17121) (downstream of this primer there exist within CTV genome a PstI site (nts 17208-17213 of CTV T36) used for cloning) (F.P.) |
| C-1358 | TTA TGC GGC CGC AGG CCT TGG ACC TAT GTT GGC CCC CCA TAG | 8 | 3'end of 3'NTR (nts 19,270-19,293 of CTV T36 clone) contain (StuI and NotI sites) (R.P.) |
| C-1568 | TAA TCG TAC TTG AGT TCT AAT ATG GCT AGC AAA GGA GAA GAA | 9 | 5'end of GFP (nts 1-21) with extension into 3' end of BYV CP IR (nts # 13620-13640 Genbank Accession # AF190581) (F.P.) |
| C-1894 | GCC GCA CTA GTA TTT AAA TCC CGT TTC GTC CTT TAG GGA CTC GTC AGT GTA CTG ATATAA GTA CAG ACT GGA CCT ATG TTG GCC CCC CAT AGG GAC AGT G | 10 | 3'end of 3'NTR (nts 19,262-19,293 of CTV T36 clone) with extensions that include a ribozyme of subterranean clover virusoid (underlined) (Turpen et al., 1993) and SwaI and SpeI restriction sites (R.P.) |
| C-1973 | ATG GAT GAG CTC TAC AAA TGA TTG AAGTGG ACG GAATAA GTT CC | 11 | 5'end of 3'NTR (nts 19021-19043 of CTV T36 clone) with extension into GFP 3'end (nts 700-720) (F.P.) |
| C-1974 | GGA ACT TAT TCC GTC CACTTC AAT CAT TTG TAG AGCTCA TCC AT | 12 | 3'end of GFP (nts 700-720) with extension into 5'end of 3'NTR (nts 19021-19043 of CTV T36 clone) (R.P.) |
| C-1975 | GCA CGT TGT GCT ATA GTA CGT GCC ATA ATA GTG AGT GCT AGC AAA GTATAA ACG CTG GTGTTT AGC GCA TAT TAA ATA CTA ACG | 13 | GLRaV-2 intergenic region of CP (nts 9568-9651 Genbank Accession number DQ286725) (F.P.) |

TABLE 1-1-continued

List of primers used in building expression vector

| Primer name | Sequence 5'-3'* | SEQ ID NO: | Description* |
|---|---|---|---|
| C-1976 | CAG CTT GCT TCT ACCTGA CAC AGT TAA GAA GCG GCATAA ATC GAA GCC AAA CCCTAA ATT TTG CAA CTC GAT CAATTG TAA CCT AGA GCG AAGTGC AAT CA | 14 | BYSV CP intergenic region of (nts 8516-8616 Genbank accesion # U51931) (F.P.) |
| C-1977 | TTT AGC GCA TAT TAA ATA CTA ACG ATG GCT AGC AAA GGA GAA GAA | 15 | 5'end of GFP (nts 1-21) with extension into the 3'end of GLRaV-2 CP intergenic region (nts 9628-9651 Genbank Accession number DQ286725) (F.P.) |
| C-1979 | ACT GTG TCA GGT AGA AGC AAG CTG TCA GAT GAA GTG GTGTTC ACG | 16 | 3'end of p23 (nts 19,000-19,020 of CTV T36 clone) with extension into 5'end of BYSV CP IR (nts 8516-8539 Genbank accesion # U51931) (R.P.) |
| C-1982 | TTG G*AT TTA GGT GAC ACT ATA G*TG GAC CTATGTTGG CCC CCC ATA | 17 | Sp6 promoter (underlined and Italics) with 3' end of 3'NTR (nts 19271-19293 of CTV T36 clone) used to develop dig labeled probe (R.P.) |
| C-1983 | GTA ACCTAG AGC GAA GTG CAA TCA ATG GCT AGC AAA GGA GAA GAA | 18 | 5'end of GFP (nts 1-23) with extension into 3'end of BYSV IR of CP (nts 8593-8616 Genbank Accession # U51931) (F.P.) |
| C-1984 | GCC TAA GCT TAC AAA TAC TCC CCC ACA ACA GCT TAC AAT ACT CCC CCA CAC AGC TTA CAA ATA CTC CCC CAC AAC AGCTTG TCG AC | 19 | 3X active ribosome complementary sequence (3XARC-1 nts 1-86) (Akbergenov et al., 2004) (F.P.) |
| C-1985 | CTC CGT GAA CAC CACTTC ATC TGA AAA TAA CAA ATC TCA ACA CAA | 20 | 5' end of TEV 5'NTR (nts 1-21 Genbank Accession # M11458) with extension into 3' end of p23 (nts 18997-19020 of CTV T36 clone) (F.P.) |
| C-1986 | TTG TGT TGA GAT TTG TTA TTT TCA GAT GAA GTG GTG TTC ACG GAG | 21 | 3'end of p23 (nts 18997-19020 of CTV T36 clone) with extension into 5' end of TEV 5'NTR (nts 1-21 Genbank Accession # M11458) (R.P.) |
| C-1989 | GGA GTATTT GTA AGCTTA GGC TCA GAT GAA GTG GTGTTC ACG GAG | | 3'end of p23 (nts 18997-19020 of CTV T36 clone) with extension into 5'end of 3XARC-1 (nts 1-21) (R.P.) |
| C-1990 | CCC CAC AAC AGCTTG TCG ACA TGG CTA GCA AAG GAG AAG AAC TTT | 23 | 5'end of GFP (nts 1-25) with extension into 3'end of 3XARC-1 (nts 66-86) (F.P.) |

TABLE 1-1-continued

List of primers used in building expression vector

| Primer name | Sequence 5'-3'* | SEQ ID NO: | Description* |
|---|---|---|---|
| C-2007 | CGT GAA CAC CACTTC ATC TGA TTC GAC CTC GGT CGT CTT AGT TAA | 24 | BYV 3'end of CPm and the intergenic region of CP (nts 13547-13570 Genbank Accession # AF190581) with extension into p23 3'end (nts 19,000-19,020 of CTV T36 clone) (F.P.) |
| C-2008 | TTA ACT AAG ACG ACC GAG GTC GAA TCA GAT GAA GTG GTG TTC ACG | 25 | 3'end of p23 (nts 19,000-19,020 of CTV T36 clone) with extension into the 3'end of CPm and CP intergenic region of BYV (nts 13,547-13,570 Genbank Accession # AF190581) (R.P.) |
| C-2009 | GGC GAT CAC GAC AGA GCC GTGTCA ATT GTC GCG GCT AAG AAT GCT GTG GAT CGC AGC GCT TTC ACT GGA GGG GAG AGA AAA ATA GTT AGT TTG TAT GCCTTA GGA AGG AACTAA GCA CGT TGT GCT ATA GTA CGT GC | 26 | GLRaV-2 3'end of CPm and 5'end of CP intergenic region (nts 9454-9590 Genbank Accession number DQ286725) (F.P.) |
| C-2010 | TGA CAC GGC TCT GTC GTG ATC GCC TCA GAT GAA GTG GTGTTC ACG | 27 | 3'end of p23 (nts 19,000-19,020 of CTV T36 clone) with extension into the 3'end of GLRaV-2 CPm coding sequence (nts 9454-9477 Genbank Accession # DQ286725) (R.P.) |
| C-2011 | GCC ACC TAC GTT ATA GGT CTT CAT TTT GTA GAG CTC ATC CAT GCC | 28 | 3'end of GFP (nts 697-717) with extension into the TEV HC-Pro protease recognition sequence (nts 2412-2435 (genetic code redundancy used to eliminate duplication Genbank Accession # M11458) (R.P.) |
| C-2012 | AAG ACC TAT AAC GTA GGT GGC ATG AAG GCT CAATAT TCG GAT CTA | 29 | 5' end of TEV HC Pro protease motif (nts 1959-1979 Genbank Accession # M11458) with extension into the HC-Pro recognition sequence (nts 2415-2438 genetic code redundancy used to eliminate duplication Genbank Accession # M11458) (F.P.) |
| C-2013 | ATG AAA ACT TAC AAT GTT GGA GGG ATG TTA CGT CCT GTA GAA ACC | 30 | 5'end of GUS (nts 4-21) with extension into the TEV HC-Pro recognition sequence and 3' end of TEV HC-Pro protease motif (nts 2412-2438 Genbank Accession # M11458) (F.P.) |

TABLE 1-1-continued

List of primers used in building expression vector

| Primer name | Sequence 5'-3'* | SEQ ID NO: | Description* |
|---|---|---|---|
| C-2014 | GGT TTC TAC AGG ACG TAA CAT CCC TCC AAC ATT GTA AGT TTT CAT | 31 | TEV HC-Pro recognition sequence (nts 2412-2438 Genbank Accession # M11458) with extension into the 5' end of GUS ORF sequence (nts 4-21) (R.P.) |
| C-2015 | CCG CAG CAG GGA GGC AAA CAA TGA TTG AAGTGG ACG GAA TAA GTT | 32 | 5' end of 3'NTR (nts 19021-19041 of CTV T36 clone) with extension into the 3' end of GUS ORF (nts 1789-1812) (F.P.) |
| C-2016 | AAC TTA TTC CGT CCA CTT CAA TCA TTG TTT GCCTCC CTG CTG CGG | 33 | 3' end of GUS (nts 1789-1812) with extension into the 5'end of 3'NTR (NTs 19021-19041 of CTV T36 clone) (R.P.) |
| C-2017 | CTT ACT CTG AAA ATA AAG ATT CTC TTT GTA GAG CTC ATC CAT GCC | 34 | 3'end of GFP (nts 697-717) with extension into the 5'end of TEV-NIa protease recognition sequence (nts 8499-8519 Genbank Accession # M11458) and 5' end of TEV NIa protease motif (nts 6270-6272 Genbank Accession # M11458) (R.P.) |
| C-2018 | AAA GAG AAT CTT TAT TTT CAG AGT AAG GGA CCA CGT GAT TAC AAC | 35 | 5' end of TEV NIa protease motif (nts 6270-6290 Genbank Accession # M11458) with extension into its recognition sequence (nts 8499-8519 Genbank Accession # M11458) and 3' end of GFP (nts 715-717) (F.P.) |
| C-2019 | CGA TTG GAA GTA TAG GTT TTC TTG CGA GTA CAC CAA TTC ACT CAT | 36 | 3'end of TEV NIa motif (nts 6961-6980 Genbank Accession # M11458) with extension into NIa recognition sequence (nts 8499-8519 Genbank Accession # M11458 genetic code redundancy used to eliminate duplication) (R.P.) |
| C-2020 | CAA GAA AAC CTA TAC TTC CAA TCG ATG TTA CGT CCT GTA GAA ACC | 37 | 5'end of GUS with extension into the TEV NIa recognition sequence (nts 8499-8519 Genbank Accession # M11458 genetic code redundancy used to eliminate duplication) and 3' end of TEV NIa protease motif (nts 6978-6980 Genbank Accession # M11458) (F.P.) |
| C-2021 | GTC ACT TTG TTT AGC GTG ACT TAG CAG CTT GCT TCT | 38 | 5'end of BYSV CP IR (nts 8516-8536 Genbank Accession # U51931) |

TABLE 1-1-continued

List of primers used in building expression vector

| Primer name | Sequence 5'-3'* | SEQ ID NO: | Description* |
|---|---|---|---|
| | ACC TGA CAC | | with extension into 3'end of p18 (nts 17269-17292 of CTV T36 clone) (F.P.) |
| C-2022 | GTG TCA GGT AGA AGC AAG CTG CTA AGT CAC GCT AAA CAA AGT GAC | 30 | 3' end of p18 (nts 17289-17292 of CTV T36 clone) with extension into 5' end BYSV CP IR (nts 8516-8536 Genbank Accession # U51931) (R.P.) |
| C-2023 | TTA GTC TCT CCA TCT TGC GTG TAG CAG CTT GCT TCT ACC TGA CAC | 40 | 5'end of BYSV CP IR (nts 8516-8536 Genbank Accession # U51931) with extension into the 3'end of p20 (nts 18286-18309 of CTV T36 clone) (F.P.) |
| C-2024 | GTG TCA GGT AGA AGC AAG CTG CTA CAC GCA AGATGG AGA GAC TAA | 41 | 3'end of p20 (nts 18286-18309 of CTV T36 clone) with extension into the 5' end of BYSV CP IR (nts 8516-8536 Genbank Accession # U51931) (R.P.) |
| C-2025 | ATG GAT GAG CTC TAC AAA TGA--GTT TCA GAA ATT GTC GAATCG CAT | 42 | 3'end of p13 ORF (nts 17581-17604 of CTV T36 clone) with extension into the 3'end of GFP ORF (nts 700-720) (F.P.) |
| C-2026 | ATG CGA TTC GAC AAT TTC TGA AAC TCA TTT GTA GAG CTC ATC CAT | 43 | 3'end of GFP ORF (nts 700-720) with extension into the 3'end of p13 ORF (nts 17581-17604 of CTV T36 clone) (R.P.) |
| C-2027 | ATG GAT GAG CTC TAC AAA TGA GTT AAT ACG CTT CTC AGA ACG TGT | 44 | 5'end of p23 IR (nts 18,310-18,330 of CTV T36 clone) with extension into 3' end of GFP (nts 700-720) (F.P.) |
| C-2028 | ACA CGT TCT GAG AAG CGT ATT AAC TCA TTT GTA GAG CTC ATC CAT | 45 | 3'end of GFP (nts 700-720) with extension into p23 IR (nts 18310-18330 of CTV T36 clone) (R.P.) |
| C-2029 | TTT AGC GCATAT TAA ATA CTA ACG ATG TAC CCATAC GAT GTT CCA | 46 | 5' end of HA TAG (21 nts) in pHA-CMV carrying bFos (AA 118-210)-YC (AA 155-238) (Hu et al., 2002) with extension into the GLRaV-2 CP IR 3' end (nts 9628-9551 Genbank Accession number DQ286725) (F.P.) |
| C-2030 | TCG AAC ATC GTATGG GTA CAT CGT TAGTAT TTA ATATGC GCT AAA | 47 | 3' end of CPm GLRaV-2 (nts 9628-9651 Genbank Accession number DQ286725) with extension into 5' end of HA tag (21 nts) in pHA-CMV carrying bFos (AA 118-210)-YC (AA 155-238) (Hu et al., 2002) (R.P.) |

TABLE 1-1-continued

List of primers used in building expression vector

| Primer name | Sequence 5'-3'* | SEQ ID NO: | Description* |
|---|---|---|---|
| C-2031 | ACT GTGTCA GGT AGA AGC AAG CTG TTA CTT GTA CAG CTC GTC CAT | 48 | 3'end EYFP-YC (AA 232-238) (Hu et al., 2002) with extension into the BYSV CP 5'IR (nts 8516-8539 Genbank Accession # U51931) (R.P.) |
| C-2032 | GTA ACCTAG AGC GAA GTG CAATCA ATG GACTAC AAA GAC GAT GAC | 49 | 5'end of FLAG tag (21 nts) from pFLAG-CMV2 carrying bJunN (Hu et al., 2002) with extension into the 3'end of BYSV CP IR (nts 8593-8616 Genbank Accession # U51931) (F.P.) |
| C-2051 | GTC ACT TTG TTT AGC GTG ACT TAG GGC GAT CAC GAC AGA GCC GTG | 50 | 3'end of GLRaV-2 CPm (nts 9454-9474 Genbank Accession # DQ286725) with extension into 3'end of p18 (nts 17269-17292 of CTV T36 clone) (F.P.) |
| C-2052 | CAC GGC TCT GTC GTG ATC GCC CTA AGT CAC GCT AAA CAA AGT GAC | 51 | 3'end of p23 (nts 19,000-19,020) with extension into the 3'end of GLRaV-2 CPm coding sequence (nts 9454-9474 Genbank Accession # DQ286725) (R.P.) |
| C-2053 | GTC ACT TTG TTT AGC GTG ACT TAG TTC GAC CTC GGT CGT CTT AGT | 52 | BYV 3'end of CPm and the intergenic region of CP (nts 13547-13567 Genbank Accession AF190581) with extension into 3'end of p18 (nts 17269-17292 of CTV T36 clone) (F.P.) |
| C-2054 | ACT AAG ACG ACC GAG GTC GAA CTA AGT CAC GCT AAA CAA AGT GAC | 53 | 3'end of p18 (nts 1729-17292 of T36 CTV clone) with extension into BYV 3'end of CPm and the intergenic region of CP (nts 13547-13667 Genbank Accession # AF190581) (R.P.) |
| C-2055 | CAC AAC GTC TAT ATC ATG GCC TAG GTT TCA GAA ATT GTC GAA TCG | 54 | 3'end of p13 ORF (nts 17581-17601 of CTV T36 clone) with extension into the 3'end of EYFP-YN (AA 147-154) from pFlag-CMV2 carrying bJun-YN (Hu et al., 2002) |
| C-2056 | CGA TTC GAC AAT TTC TGA AAC CTA GGC CAT GAT ATA GAC GTT GTG | 55 | 3'end of EYFP-YN (AA 147-154) from pFlag-CMV2 carrying bJun-YN (Hu et al., 2002) with extension into the 3'end of p13 (nts 17581-17601 of CTV T36 clone) |
| C-2057 | GGC ATG GAC GAG CTG TAC AAGTAA TTG AAGTGG ACG GAATAA GTT | 56 | 3'end EYFP-YC (AA 231-238) (Hu et al., 2002) with extension into 5'end of 3'NTR (nts 19021-19041 of CTV T36 clone) |

TABLE 1-1-continued

List of primers used in building expression vector

| Primer name | Sequence 5'-3'* | SEQ ID NO: | Description* |
|---|---|---|---|
| C-2058 | AAC TTA TTC CGT CCA CTT CAA TTA CTT GTA CAG CTC GTC CAT GCC | 57 | 5'end of 3'NTR (nts 19021-19041 of CTV T36 clone) with extension into 3'end EYFP-YC (AA 231-238) (Hu et al., 2002) |
| C-2059 | TCG CTC TTA CCT TGC GAT AAC TAG CAG CTT GCT TCT ACCTGA CAC | 58 | BYSV CP 5'IR (nts 8516-8536 Genbank Accession # U51931) with extension into the 3'end of p13 (nts 17,662-17,685 of CTV T36 clone) (F.P.) |
| C-2063 | GTA ACCTAG AGC GAA GTG CAA TCA ATG TTA CGT CCT GTA GAA ACC | 59 | 5'end of GUS ORF (nts 1-21) with extension into the 3' end of BYSV CP IR (with extension into the 3'end of BYSV CP IR (nts 8593-8616 Genbank Accession # U51931) (F.P.) |
| C-2064 | GGT TTC TAC AGG ACG TAA CAT TGA TTG CACTTC GCT CTA GGTTAC AA | 60 | 3'end of BYSV CP IR (nts 8591-8618 Genbank Accession # U51931) with extension into the 5' end of GUS ORF (nts 1-21) (R.P) |
| C-2067 | CCG CAG CAG GGA GGC AAA CAA TGA GTT TCA GAA ATT GTC GAATCG | 61 | 3'end of p13 (nts 17581-17601 of CTV T36 clone) with extension into the 3'end of GUS (nts 1789-1812) (F.P.) |
| C-2068 | CGA TTC GAC AAT TTC TGA AAC TCA TTG TTT GCCTCC CTG CTG CGG | 62 | 3'end of GUS (nts 1789-1812) with extension into the 3'end of p13 (nts 17581-17601 of CTV T36 clone) |
| C-2069 | GTG TCA GGT AGA AGC AAG CTG CTA GTT ATC GCA AGG TAA GAG CGA | 63 | 3'end of p13 (nts 17662-17685 of CTV T36 clone) with extension into 5'end of BYSV IR CP 5'IR (nts 8516-8536 Genbank Accession # U51931) (R.P.) |
| C-2070 | ATG GAT GAG CTC TAC AAATGA AGT CTA CTC AGT AGT ACG TCT ATT | 64 | 5'IR of p20 (nts 17686-17709 of CTV T36 clone) with extension into the 3'end of GFP (nts 700-720) (F.P.) |
| C-2071 | AAT AGA CGT ACT ACT GAGTAG ACT TCA TTT GTA GAG CTC ATC CAT | 66 | 3'end of GFP (nts 700-720) with extension into the 5'IR of p20 (nts 17686-17709 of CTV T36 clone) (R.P.) |
| C-2085 | GCG G ATGCAT TATTT GGTTTT ACA ACA ACG GTA CGT TTC AAA ATG | 66 | 3'end of p18 (nts 17201-17245 of CTV T36 clone) with two point mutations (C-A(17205) and G-T(17210)) creating NstI site to replace the PstI site (F.P.) |
| C-2087 | AAG ACC TAT AAC GTA GGT GGC ATG AAG GCT CAA TAT | 20 | 5' end of TEV HC-Pro protease motif (nts 1959-1979 Genbank |

TABLE 1-1-continued

List of primers used in building expression vector

| Primer name | Sequence 5'-3'* | SEQ ID NO: | Description* |
|---|---|---|---|
| | TCG GAT CTA | | Accession # M11458) with extension into the HC-Pro recognition sequence (nts 2415-2438 genetic code sequence redundancy was used to eliminate duplication Genbank Accession # M11458) (F.P.) |
| C-2088 | ATG AAA ACT TAC AAT GTT GGA GGG ATG GCT AGC AAA GGA GAA GAA | 67 | 5'end of GFP ORF (nt 4-21) with extension into the TEV HC-Pro recognition sequence (nts 2412-2433 Genbank Accession # M11458) (F.P.) |
| C-2089 | TTC TTC TCC TTT GCT AGC CAT CCC TCC AAC ATT GTA AGT TTT CAT | 68 | TEV HC-Pro recognition sequence (nts 2412-2438 Genbank Accession # M11458) with extension into the 5' end of GFP ORF sequence (nts 4-21) (R.P.) |
| C-2091 | GAG AAT CTT TAT TTT CAG AGT AAG GGA CCA CGT GAT | 69 | 5' end of TEV NIa protease motif (nts 6270-6291 Genbank Accession # M11458) with extension into its recognition sequence (nts 8499-8519 Genbank Accession # M11458) (F.P.) |
| C-2092 | GAA AAC CTA TACTTC CAATCG ATG GCT AGC AAA GGA GAA GAA CT | 70 | 5'end of GFP ORF (nts 1-23) with extension into the TEV-NIa protease recognition sequence (nts 8499-8519 genetic code sequence redundancy used to eliminate duplication Genbank Accession # M11458) (F.P.) |
| C-2093 | AGT TCT TCT CCT TTG CTA GC CAT CGA TTG GAA GTA TAG GTT TTC | 71 | TEV NIa protease recognition sequence (nts 8499-8519 genetic code sequence redundancy used to eliminate duplication Genbank Accession # M11458) with extension into the GFP ORF sequence (nts 1-23) (R.P.) |
| C-2094 | AAG ACCTAT AAC GTA GGT GGC ATG AAG GGA CCA CGT GAT TAC AAC | 72 | 5' end of TEV-NIa protease motif sequence nts 6270-6291 Genbank Accession # M11458) with extension into the HC-Pro recognition sequence (nts 2415-2438 genetic code sequence redundancy used to eliminate duplication Genbank Accession # M11458) (F.P.) |

TABLE 1-1-continued

List of primers used in building expression vector

| Primer name | Sequence 5'-3'* | SEQ ID NO: | Description* |
|---|---|---|---|
| C-2095 | CCC TCC AAC ATT GTA AGT TTT CAT TTG CGA GTA CAC CAATTC ACT | 73 | 3'end of TEV NIa protease motif (nts 6959-6981 Genbank accession # DQ986288) with extension into the TEV HC-Pro protease motif (nts 2415-2438 Genbank accession # M11453) (R.P.) |
| C-2096 | GAG ATT CTT TAT TTT CAG AGT AAG GCT CAATAT TCG GAT CTA AAG | 74 | 5'end of TEV HC-Pro protease motif (nts 1959-1979 Genbank Accession # M11458) with extension into the TEV NIa protease recognition sequence (nts 8499-8519 Genbank accession # M11458) (F.P.) |
| C-2097 | CGA TTG GAA GTATAG GTT TCC TTC GGATTC CAA ACCTGA ATG AAC | 75 | 3'end of HC-Pro protease motif (nts 2388-2411 Genbank accession # M11458) with extension into the TEV NIa protease recognition sequence (nts 8499-8519 Genbank accession # M11458) (R.P.) |
| C-2098 | GCC ACCTAC GTT ATA GGT CTT CAT GAT GAA GTG GTGTTC ACG GAG | 76 | 33'end of p23 (nts 18997-19017 of CTV T36 clone) with extension into the 5'end of TEV HC-Pro protease recognition sequence nts 2412-2435 (genetic code sequence redundancy used to eliminate duplication) Genbank Accession # M11458)(R.P.) |
| C-2099 | ACT CTG AAA ATA AAG ATT CTC GAT GAA GTG GTGTTC ACG GAG AAC | 77 | 3'end of p23 (nts 18994-19017 of CTV T36 clone) with extension into the 5'end of TEV NIa protease recognition sequence (nts 8499-8519 Genbank Accession # M11458) (R.P.) |
| M-804 | CAT TTA CGA ACG ATA GCC ATG GCT AGC AAA GGA GAA GAA | 78 | 5'end of GFP (nts 1-20) with 3'end of TEV 5'NTR (nts 126-143 Genbank Accession # M11458) (F.P.) |

Polymerase Chain Reaction (PCR)

PCR was performed using diluted plasmids (1:50) as templates using Vent DNA polymerase (New England Biolabs, Ipswich, Ma.) according to the manufacturer recommendations.

Agro-Injection/Infiltration

Agro-inoculation of *Nicotiana benthamiana* was performed according to the procedure developed by Gowda et al., (2005) with minor modifications. *Agrobacterium tumefaciens* EHA 105 was transformed with the binary plasmid containing CTV, variants (expression vectors) and silencing suppressors (p19 of Tomato bushy stunt virus (Gowda et al., 2005); p24 of GLRaV-2 (Chiba et al., 2007), P1/HC-Pro of Turnip mosaic virus (Kasschau et al., 2003) and p22 of Tomato chlorosis virus (Cañizares et al., 2008) by heat shock method (37° C. for 5 minutes) and subsequently were grown at 28° C. for 48 hours (hrs) on luria burtani (LB) (Sigma-Aldrich, St Louis, Mo.) plates supplemented with antibiotics (kanamycin (50 microgram (µg)/milliliter (ml)) and Rifampicilin ((50 µg/ml)). The colonies (two individual colonies per construct) were grown overnight as seed cultures in LB medium supplemented with antibiotics. On the next day 0.5 ml of the seed culture was used to inoculate 35 ml of LB medium supplemented with antibiotics for overnight growth. The bacterial culture was centrifuged at 6,000 rotation per minute (rpm) and resuspended in 10 milli molar (mM) $MgCL_2$ and 10 mM MES. The pellet was washed with 10 mM $MgCL_2$ and 10 mM MES and suspended in induction medium; 10 mM $MgCL_2$ and 10 mM MES containing acetosyringone at a final concentration of 150 µM. The suspension was incubated in the induction medium for at least 5 hrs before injection into the stem or infiltration into the abaxial (lower) surface of N. benthamiana leaves.

Plant Growth Conditions

N. benthmaiana plants maintained in a growth-room (21° C. with 16 hrs of light in a 24 hr period) were used for agro-injection/agro-infiltration four weeks after transplanting.

Infection of Citrus Plants

Recombinant virions of CTV for infection of citrus plants were obtained from infiltrated and/or systemic leaves of N. benthamiana. The virions were partially purified and enriched by concentration over a sucrose cushion in a TL 100 or SW41 rotor (Robertson et al., 2005). Virions of constructs expressing two foreign proteins were concentrated two times over a step gradient followed by a cushion gradient in SW28 and SW41 rotors, respectively (Garnsey and Henderson, 1982). Inoculation of citrus plants was carried out by bark flap inoculation into 1-1.5 year old Citrus macrophylla seedlings (Robertson et al., 2005) which were grown in a greenhouse with temperatures ranging between approximately 25-32° C.

Protoplast Preparation, Transfection, RNA Isolation and Northern Blot Analysis

N. benthamiana leaf mesopyhll protoplasts were prepared according to the procedure previously developed by Nava-Castillo et al., (1997). Surface sterilized leaves from three week old N. benthamiana plants were gently slashed on the lower side with a sterile blade and incubated overnight in the dark (16-20 hrs) in 0.7M MMC (0.7M mannitol, 5 mM MES, 10 mM $CaCl_2$) supplemented with the 1% cellulose (Yakult Honsh, Tokyo, Japan) and 0.5% macerase pectinase enzymes (Calbiochem, La Jolla, Calif.).

Capped in vitro RNA transcripts from NotI or StuI linearized plasmid DNA were generated (Satyanarayana et al., 1999) using Sp6 RNA polymerase (Epicentre Technologies, WI) and were transfected into the protoplasts using PEG (poly ethylene glycol) as described by Satyanarayana et al., (1999). Four days after transfection, protoplasts were used for preparation of total RNA for northern blot hybridization analysis and isolation of virions. Protoplasts were pelleted in equal amounts in two 1.5 ml eppendorf tubes. The first tube was flash frozen in liquid nitrogen and stored at −80° C. for isolation of virions to subsequently inoculate a new batch of protoplasts to amplify virions (Satyanarayana et al., 2000). The second tube was used for RNA isolation by the buffard buffer disruption of protoplasts followed by phenol:chloroform:isoamyl alcohol (25:24:1) extraction and ethanol precipitation as previously described by Navas-Castillo et al., (1997) and Robertson et al., (2005). Total RNA was resuspended in 20 µl DNAse/RNAase free water and used in Northern blot hybridization analysis as previously described by Lewandowski and Dawson (1998). In brief, isolated RNA was heat denatured in denaturing buffer (8.6% formaldehyde, 67% formamide in 1×MOPS (5 mM sodium acetate, 1 mM EDTA, 0.02M MOPS pH=7.0) separated in a 0.9% agarose gel in 1×MOPS containing 1.9% formaldehyde, and transferred onto a nylon membrane (Boehringer Mannheim, Germany) by electroblotting. Pre-hybridization (at least 1 hr) and hybridization (overnight) were carried out in a hybridization oven (Sigma-Aldrich, St. Louis, Mo.) at 68° C. A 900 nts digoxigenin labeled RNA probe corresponding to the 3' end of the CTV genome (plus strand specific CTV RNA probe) (Satyanarayana et al., 1999) was used for hybridization except when the insertion of the foreign genetic material was behind p23 in which case a digoxigenin labeled RNA probe was produced from PCR amplified DNA (reverse primer contain 3'NTR of CTV and SP6 phage promoter (C-1982) according to the manufacturer recommendation (Boehringer Mannheim, Germany) that is complimentary to the sequence inserted behind p23 in addition to the 3'NTR sequence of CTV.

Western Blots

After powdering the plant tissue in liquid nitrogen via grinding in a mortar and pestle, laemmli buffer (50 mM Tris-Cl, pH 6.8, 2.5% 2-mercaptoethanol, 2% SDS, 0.1% bromophenol blue, 10% glycerol) was added (100 µl per 100 mg tissue). The sample was transferred to a 1.5 ml centrifuge tube and boiled in a water bath for 3 minutes followed by centrifugation at maximum speed for 2 minutes. The supernatant was transferred to a new tube and stored at −20° C. until further use. The electrophoresis was carried out in a 12% SDS-Polyacrylamide gel (Bio-Rad, Hercules, Calif.) followed by two hours of semi-dry blotting to transfer the protein onto a nitrocellulose membrane (Bio-Rad, Hercules, Calif.). The membrane was blocked for 1 hr at room temperature followed by incubation with the primary antibody of either CP (1:5000), GFP (1:100) (Clontech Laboratories, Palo Alto, Calif.) or GUS (1:1000) (Molecular probes, Eugene, Or.) for an hour followed incubation for 1 hr in horseradish peroxidase conjugated donkey anti-rabbit secondary antibody (1:10,000) (Amersham, Buckinghamshire, United Kingdom). Finally, the chemiluminescent system for western blot (Amersham, Buckinghamshire, United Kingdom) development on an X-ray film (Kodak, Rochester, N.Y.) was used according to the manufacturer recommendations.

Plant and Protoplast Photos

Plant pictures under UV or white light were taken with a Canon Camera (Canon EOS Digital Rebel XTi 400D, Lake Success, New York). Close up fluorescent pictures of plant parts or protoplast were taken using a fluorescent dissecting microscope (Zeiss Stemi SV 11 UV-fluorescence dissecting microscope, Carl Zeiss Jena, GmbH., Jena, Germany). High resolution protoplast pictures were taken using a confocal scanning microscope (Leica TCS SL, Leica Microsystems, Inc., Exton, Pa.).

Enzyme Linked Immunosorbent Assay (ELISA)

Double antibody sandwiched ELISA was used according to the procedure developed by Garnsey and Cambra (1991). A rabbit polyclonal antibody (1 µg/ml) was used for coating the ELISA plate. The plant tissue sample was diluted at a 1:20 in PBS-T (phosphate buffer saline-1% Tween 20)

extraction buffer. The detection antibody used was Mab ECTV 172 (1:100K dilution).

GUS Assay

Citrus bark pieces or systemic leaves from Agro-inoculated N. benthamiana plants that were surface sterilized in alcohol (70% ethanol) followed by Sodium hypo chloride (10% solution) and washing three times in sterile distilled water before staining for GUS. The samples were incubated overnight in an EDTA-phosphate buffer (0.1M $Na_2HPO_4$, 1 mM $Na_2EDTA$) containing 1 mg/ml X-gluc (cyclohexylammounium salt: Gold Biotechnology, St Louis, Mo.). Fixing of the tissue was done in 95% ethanol:glacial acetic acid solution (3:1.

Example 1: Systems Used to Examine CTV-Based Expression Vectors

CTV-based expression vectors were examined in three systems, N. benthamiana mesophyll protoplasts as well as whole plants of N. benthaminia and Citrus macropylla. The full-length cDNA clone of CTV (pCTV9R) and a mutant with most of the p33 gene deleted (pCTV9RΔp33), which has a PstI restriction site removed making cloning easier and still retaining the ability to infect most citrus varieties (Tatineni et al., 2008), was used for building constructs to infect whole plants. Relatively quick assays were done in N. benthamiana protoplasts, which require constructs to be built in the SP6 transcription plasmid (Satyanarayana et al., 1999). A mini-replicon pCTVΔCla 333R (Gowda et al., 2001), with most of the 3' genes removed, was convenient to use in protoplasts. The ultimate goal to obtain citrus trees infected with the different CTV expression vectors was much more difficult and time consuming. So far, agro-inoculate citrus trees has proven difficult. Thus, to avoid this difficulty virions are amplified and concentrated for inoculation of citrus trees by stem-slashing or bark-flap inoculation (Robertson et al., 2005; Satyanarayana et al., 2001). N. benthamiana protoplasts can be inoculated with in vitro produced transcripts of recombinant CTV constructs and the virus amplified by successively passaging virions in crude sap through a series of protoplasts (Folimonov et al., 2007; Satyanarayana et al., 2001; Tatineni et al., 2008). Also, recombinant CTV can be amplified in N. benthamiana plants after agro-inoculation (Gowda et al., 2005). The virus can infect mesophyll cells of agro-inoculated areas of leaves, but as the virus moves systemically into upper non-inoculated leaves, it is limited to vascular tissues and usually induces vein clearing and later vein necrosis. All of the vector constructs were examined during systemic infection of N. benthamiana plants. Since CTV virions do not resuspend after centrifugation to a pellet, virions have to be concentrated by centrifugation through a sucrose step gradient (Garnsey et al., 1977; Robertson et al., 2005). After inoculation, the tops of citrus plants were removed, and viral systemic infections were monitored in new growth after 2-3 months. Once trees were infected, inoculum (buds, leaf pieces, or shoots) from the first infected plants was then used to propagate new plants for experimentation. The whole process takes approximately one year. For this reason, the inventors chose to examine only the most promising vector constructs in citrus trees. Some of the later developed constructs are not yet in citrus.

Example 2: Addition of an Extra Gene at Different Locations within the CTV Genome Insertions at the p13 Gene Site The effective CTV vector developed previously (Folimonov et al., 2007) has the additional gene inserted between the two coat protein genes, positioning the foreign gene as the sixth gene from the 3' terminus. Yet, the most highly expressed genes of CTV tend to be closer to the 3' terminus. Thus, it appeared that positioning an inserted gene closer to the 3' terminus could result in higher levels of expression. P13, the third gene from the 3' terminus, is a relatively highly expressed gene that is not necessary for the infection of most of the CTV host range (Tatineni et al., 2008; Tatineni et al., in preparation). Yet, replacement of the p13 ORF with the GFP ORF was not successful in previous attempts (Folimonov et al., 2007). There were possible reasons for the failure. The previous construct was designed with the assumption that translation initiated at the first start codon, but the p13 ORF has a second in-frame AUG. Translation might normally start at the second AUG. However, fusion of the GFP ORF behind the second in frame AUG also did not express the reporter gene (Gowda et al., unpublished result). A second possibility is that the p13 controller element (CE) might extend into the p13 ORF or that ribosome recruitment is directed from within the ORF. Here, the inventors deleted the p13 CE and ORF and inserted a new ORF behind a heterologous CE in the p13 position. The GFP ORF controlled by the CP-CE from BYSV (101 nts from 8516-8616 accession # U51931), GLRaV-2 (198 nts from 9454-9651 accession # DQ286725) or BYV were engineered into pCTV9RΔp33 as a replacement for nts 17293-17581 (CTV33-Δ13-BY-GFP-57, CTV33-Δ13-G-GFP-65, CTV33-Δ13-B-GFP-66 respectively) (FIG. 1 A). RNA transcripts were used to inoculate a series of protoplasts to determine whether the constructs could replicate and whether virions formed sufficiently for passage in crude sap to a new batch of protoplasts. The fluorescence of infected protoplasts (data not presented) and northern blot hybridization analysis demonstrated the successive passage of the expression vectors through the protoplast transfers (FIG. 1B). Furthermore, the level of the GFP mRNA was similar to that of CP. Vectors sequences CTV33-Δ13-BY-GFP-57, CTV33-Δ13-G-GFP-65 and CTV33-Δ13-B-GFP-66 then were transferred into the *Agrobacterium* binary plasmid for agro-inoculation of *N. benthamiana* plants. All three vectors infected and moved systemically in vascular tissue of the *N. benthamiana* plants as indicated by fluorescence in leaves, buds, flowers and corolla (FIG. 1C), vein clearing phenotype in early stages, as well as confirmed by ELISA (Data not presented).

CTV33-Δ13-G-GFP-65 and CTV33-Δ13-B-GFP-66 were amplified and used to inoculate *Citrus macrophylla* plants. The initially infected plants exhibited bright fluorescence in vascular tissue (FIG. 1D). Fluorescence continued in these plants 2 years after inoculation.

The GFP ORF (720 nts) was replaced with the GUS ORF (1812 nts) in the same position to examine the expression of a larger foreign gene. The BYSV CP-CE was selected to drive the GUS ORF in expression vector CTV33-Δ13-BY-GUS-61 (FIG. 2A). RNA transcripts of this construct were transfected into protoplast where the virus replicated and passaged efficiently from one protoplast batch to another as indicated by northern blot hybridization analysis (FIG. 2B). In addition, it revealed that the level of accumulation of GUS mRNA was identical to the CP mRNA, and the CP and CPm mRNAs of vector were similar to that of the wild type virus. Agro-inoculation of *N. benthamiana* plants revealed that the construct infected and spread throughout the vascular tissue of the plants based on GUS staining and confirmed by ELISA (Data not presented) and the vein clearing phenotype.

Virions isolated from infiltrated leaves of *N. benthamiana* plants of CTV33-Δ13-BY-GUS-61 infected *Citrus macrophylla* plants as confirmed by ELISA (Data not presented) and the bioactivity of the GUS protein (FIG. 2C). The GUS gene was still biologically active in *citrus* 1.5 year after inoculation.

Technically, the above constructs replaced a gene (p13) rather than added an extra gene. To examine a vector with an extra gene between p13 and p20, the CP-CE of BYSV controlling the GFP ORF was inserted between nts 17685-17686 to yield CTV33-13-BY-GFP-69 (FIG. 3A). This vector should produce an extra subgenomic RNA between the subgenomic RNAs of p13 and p20. Vector CTV33-13-BY-GFP-69 was examined in *N. benthamiana* protoplasts and plants. In the protoplast system, CTV33-13-BY-GFP-69 replicated efficiently and was successfully passaged from one protoplast batch to another demonstrating efficient replication and virion formation as indicated by fluorescence (Data not presented) and northern blot hybridization analysis (FIG. 3B). The foreign mRNA accumulated at a relatively high level but the CP mRNA was reduced. Similar to the replacement of p13 constructs, agro-inoculation of the expression vector CTV33-13-BY-GFP-69 into *N. benthamiana* plants enabled the new vector to infect and spread throughout the vascular tissue (FIG. 3C).

Construct CTV33-13-BY-GFP-69 infected *C. macrophylla* plants as indicated by strong fluorescence throughout the vascular tissue (FIG. 3C) and confirmed by ELISA (Data not presented). The plants were still fluorescencing 2 years after inoculation.

Insertion Between p20 and p23

Figure 3:
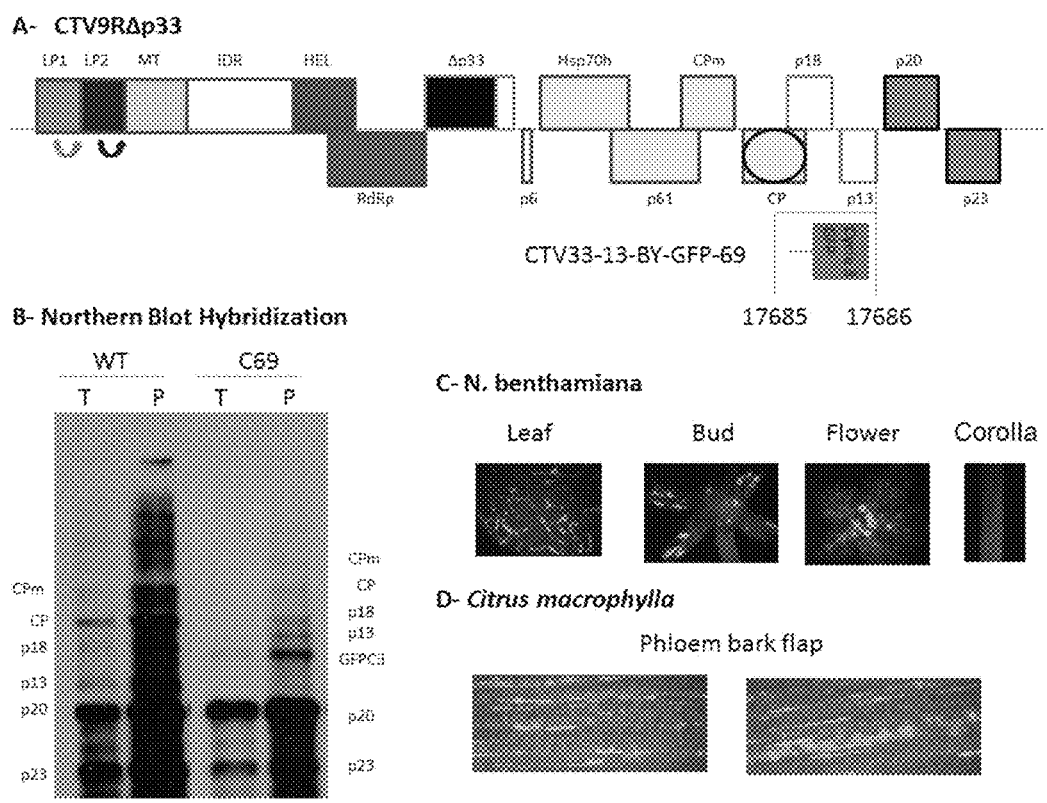
Figure 4:
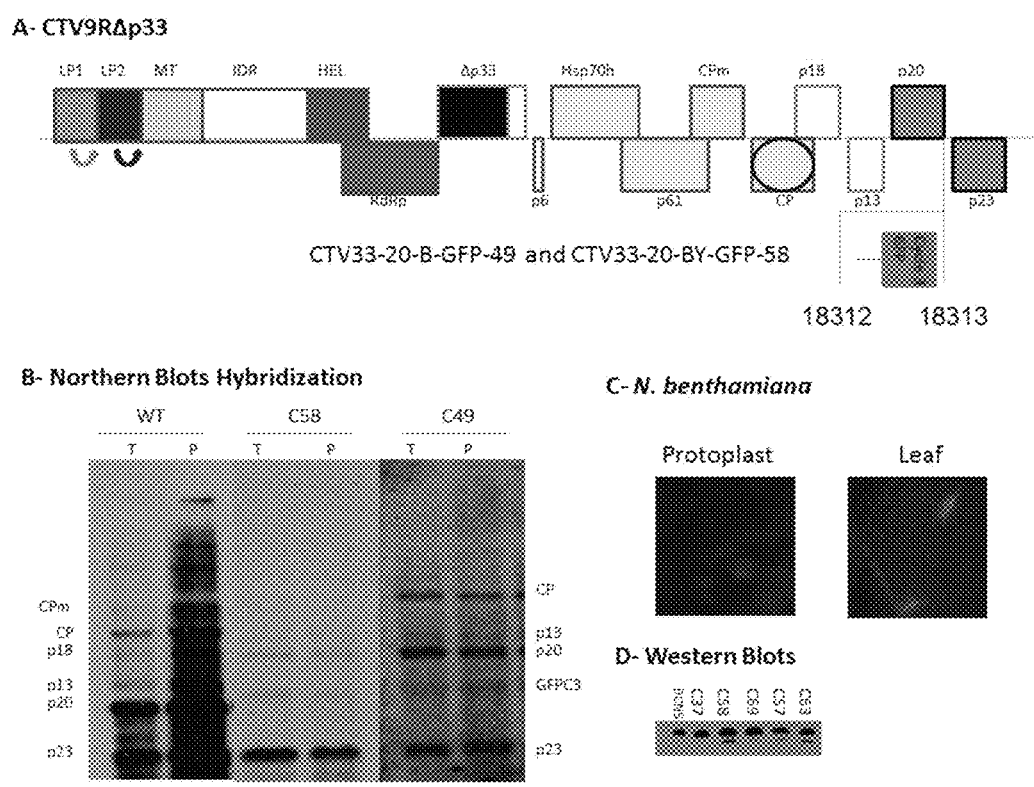

To examine expression of a foreign gene closer to the 3' NTR of CTV, an extra gene was inserted between the p20 and p23 genes (nts 18312-18313). The BYV or BYSV CP-CE was used to drive the GFP mRNA in two vectors based on T36 CTV9RΔp33 (CTV33-20-B-GFP-49 and CTV33-20-BY-GFP-58) (FIG. 3-4A). The new vectors produced an extra sgRNA mRNA between the p20 and p23 sgRNAs (FIG. 4B). However, the accumulation of the p20 sg mRNA was substantially reduced. Both vectors replicated and were passaged in protoplasts, but the protoplast passage was reduced as demonstrated by reduced numbers of cells with GFP fluorescence and northern blot hybridization (FIGS. 4B & C). When both CTV33-20-B-GFP-49 or CTV33-20-BY-GFP-58 vectors were infiltrated into *N. benthamiana* leaves for transient expression, the vectors replicated and produced abundant amounts of GFP as indicated by fluorescence (Data not presented) and western blot analysis (FIG. 4D). However, when agro-inoculated into *N. benthamiana* plants, the constructs replicated but movement into upper non-inoculated leaves was random and often unsuccessful. Since systemic infection of *N. benthamiana* plants was marginal, no attempt was made to inoculate *citrus*.

Insertion Between p23 and 3'NTR

The next position to be examined was to make the inserted gene the 3'-most gene. Since CTV gene expression tends to be highest for genes positions nearer the 3' terminus, this position could be expected to result in the highest level of expression of a foreign gene (Navas-Castillo et al., 1997; Hilf et al., 1995). Although the 3' NTR has been analyzed (Satyanarayana et al., 2002a), it was not known what effect an extra gene in this area would have on the efficiency of replication. The insertion of an extra gene between the CP gene and the 3'NTR in Tobacco mosaic virus (TMV) and Alfalfa mosaic virus (AMV) failed to produce viable vectors (Dawson et al., 1989; Sánchez-Navarro et al., 2001). The CP-CE of BYSV, GLRaV-2 or BYV in front of the GFP ORF was inserted between nucleotides 19020 and 19021 creating vectors CTV33-23-BY-GFP-37, CTV33-23-G-GFP-40 and CTV33-23-B-GFP-42, respectively (FIG. 5A). All of the constructs when transfected into the protoplast replicated and were passaged efficiently as indicated by northern blot hybridization analysis (FIG. 5B) and GFP fluorescence (Data not presented). The GFP mRNA was the highest accumulating mRNA, with only slight decreases to the other mRNAs compared to that of the wild type virus (FIG. 5B). Furthermore, the constructs with a GFP insertion 3' of the p23 ORF had the highest accumulation of the foreign gene mRNA among the constructs examined. CTV33-23-BY-GFP-37, CTV33-23-G-GFP-40 and CTV33-23-B-GFP-42 constructs were agro-inoculated into *N. benthamiana* plants. The infections spread systemically throughout the vascular tissue as demonstrated by the fluorescence (FIG. 5C), phenotype (vein clearing followed by necrosis), and ELISA (Data not presented). The fluorescence in the vascular tissue of *N. benthamiana* plants was extremely bright and continued for the life of the infected plants (FIG. 5C)

Figure 5:
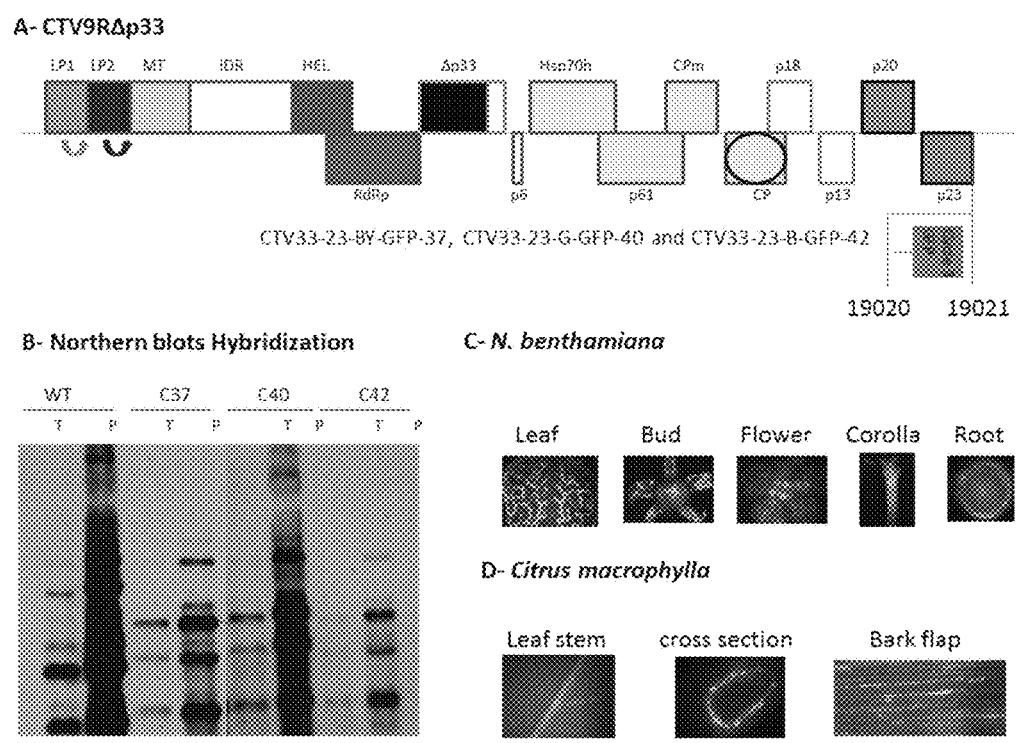
Figure 9:
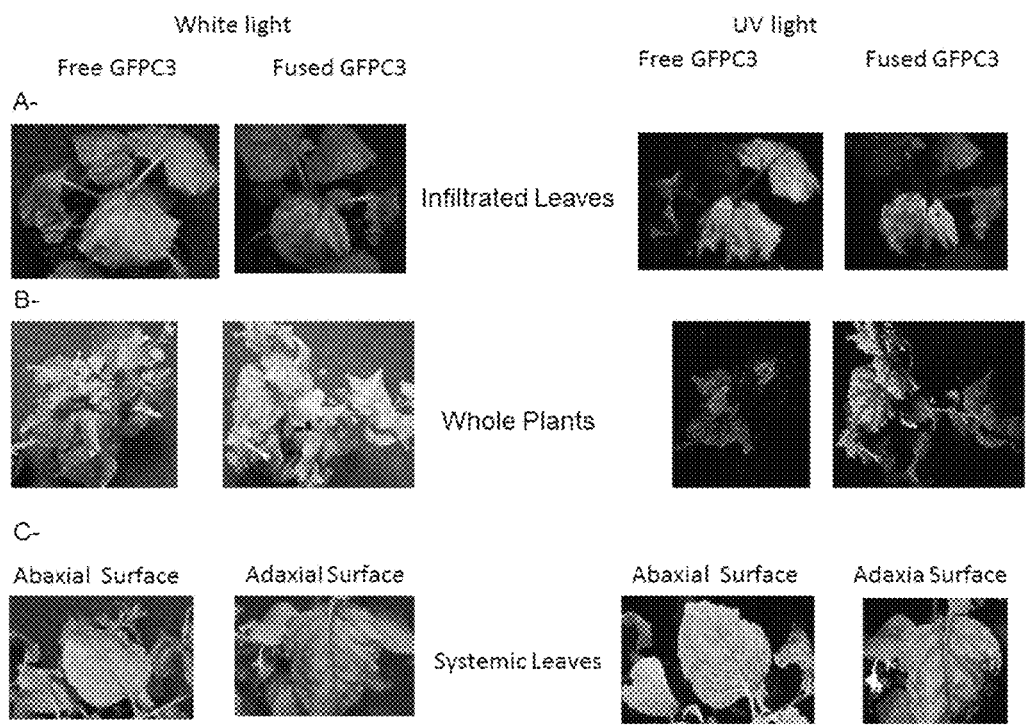

Construct CTV33-23-BY-GFP-37 was amplified by passage through 12 protoplast sets before *citrus* inoculation. C *macrophylla* plants that were bark-flap inoculated with the concentrated virions became infected. The infection of *citrus* was confirmed by fluorescence of GFP (FIGS. 3-5D) and ELISA (Data not presented). Inoculation of *citrus* with constructs CTV33-23-G-GFP-40 was done via amplification in agro-inoculated *N. benthamiana* plants. The infection rate was in 1 of 4 *C. macrophylla* plants as indicated by fluorescence (FIG. 5D) and confirmed by ELISA (Data not presented). Similar to *N. benthamiana*, *citrus* plants expressed bright fluorescence in the vascular tissue 12 weeks after inoculation and were still fluorescing 2.5 years later (FIG. 5D).

To examine the ability of the vector to express a larger gene at this position, the GUS ORF behind the BYSV CP-CE was inserted 3' of the p23 gene resulting in construct CTV33-23-BY-GUS-60 (FIG. 6A). The construct replicated in successfully transfected protoplasts. However, the accumulation levels of all the CTV subgenomic RNAs were decreased profoundly compared to the wild type virus as demonstrated by northern blot hybridization analysis (FIG. 6B). Also, the CTV33-23-BY-GUS-60 construct passaged poorly in protoplasts (Data not presented). Yet, after agro-inoculation of *N. benthamiana* plants, the vector replicated and moved systemically as demonstrated by the systemic symptoms (vein clearing followed by necrosis), ELISA (Data not presented) and GUS assays. The activity of GUS in the *N. benthamiana* plants was continuously produced in old and new leaves until the death of the plant (FIG. 7C). Similar to CTV33-Δ13-BY-GUS-61, the location between p23 and 3'NTR was able to accommodate moderately to long genes albeit with a differential effect on sg RNA levels of upstream genes (FIG. 5B & FIG. 6B)

Figure 19:
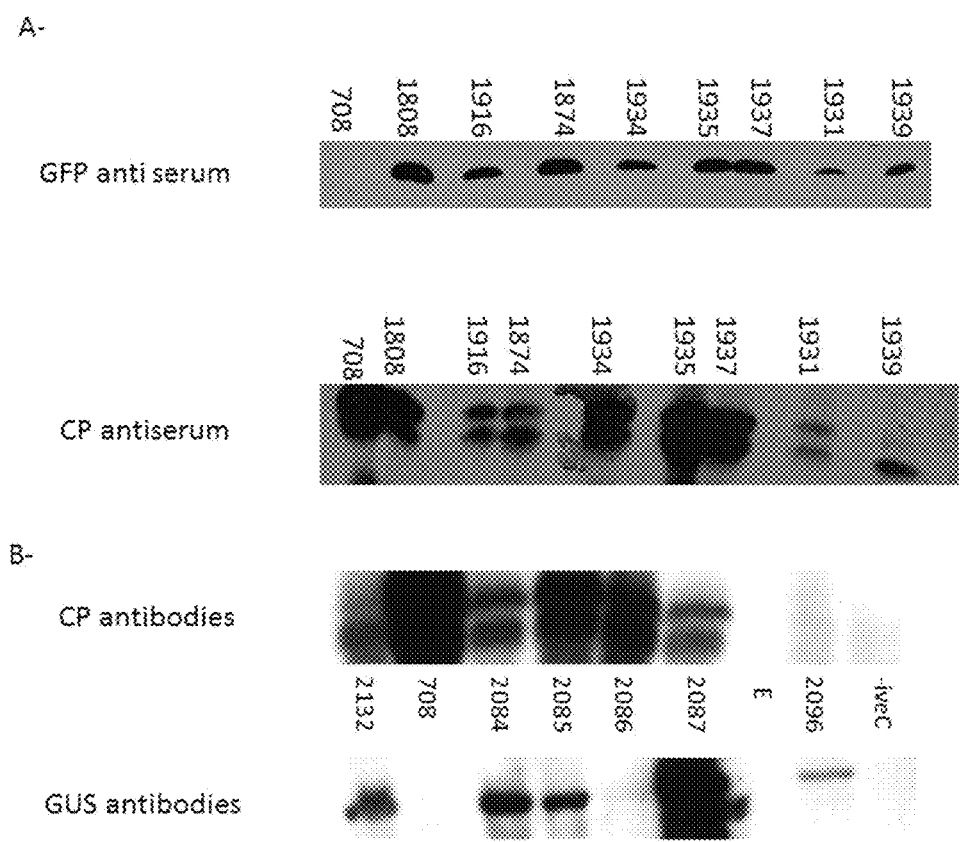
Figure 29:
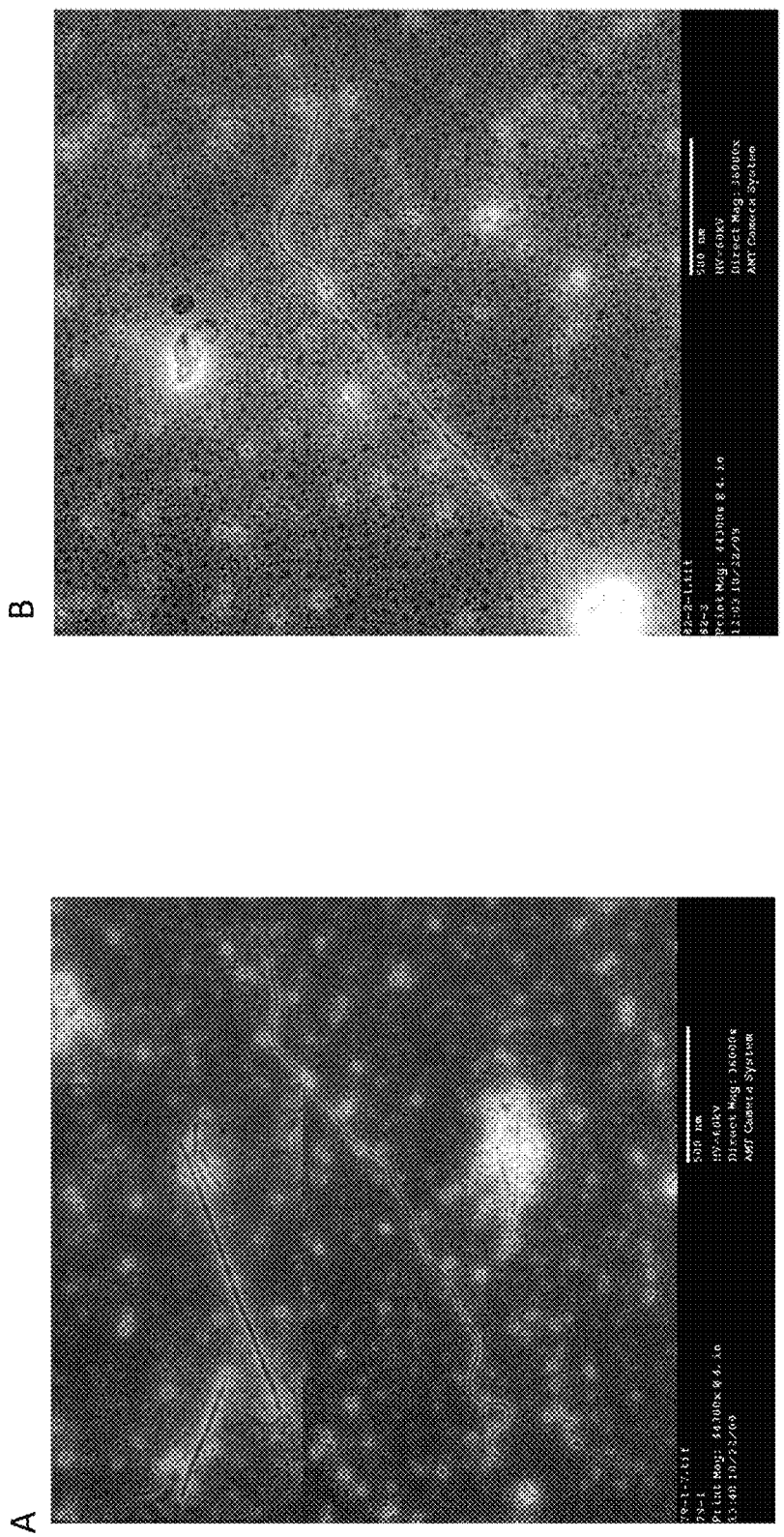

Concentrated virions from Construct CTV33-23-GUS-60 were used to inoculate *C. macropyhlla* plants, which became infected as confirmed by ELISA (Data not presented) and activity of the GUS gene (FIG. 6C). Furthermore, GUS activity and western blot analysis revealed the presence of the GUS gene in *citrus* 1.3 years after inoculation (FIG. 6C, FIG. 19).

Example 3: Production of an Extra Polypeptide without Producing an Extra Subgenomic mRNA Internal Ribosome Entry Site Strategy (IRES)
The Tobacco Etch Virus (TEV) IRES The 5'NTR of TEV mediates cap independent translation of the viral mRNA. Studies on the 5'NTR of TEV demonstrate its ability to initiate translation at an internal ORF in a bi-cistronic mRNA (Gallie, 2001; Niepel and Gallie, 1999). The 5'NTR of TEV (nts 2-144 Genbank accession # DQ986288) was inserted into a CTV mini-replicon behind the p23 ORF (between nts 19020-19021) followed by the GFP ORF (CTVp333R-23-ITEV-GFP) (FIG. 7A) to examine whether a bicistronic subgenomic mRNA would work with this virus. Although northern blot hybridization analysis demonstrated that the mini-replicon replicated and produced abundant amounts of the bicistronic mRNA in transfected N. benthamiana protoplasts (FIG. 7C), GFP fluorescence was not observed, suggesting a lack of translation of the second ORF in the bicistronic mRNA. The inventors also examined the 5'NTR TEV IRES construct in full length CTV in N. benthamiana protoplasts and plants. Construct CTV33-23-ITEV-GFP-41 was passaged efficiently from protoplast to the next protoplast sets (FIG. 7B), indicating the good replication and formation of virions, but no fluorescing protoplasts were observed demonstrating that this IRES did not work well in CTV (data not presented). This construct infected and moved systemically in N. benthamiana plants based on the systemic symptoms of vein clearing followed by necrosis and ELISA (Data not presented), but no GFP fluorescence was observed under UV light (Data not presented).

Active ribosome complementary sequence (ARC) IRES

Insertion of an IRES consensus sequence obtained from analysis of host and viral mRNAs (the engineered 3×ARC-1 (86 nts) IRES (Akbergenov et al., 2004)) was next examined for activity in CTV. This IRES was fused behind the p23 ORF (nts 19020-19021) in both the CTV mini-replicon (CTVp333R-23-I3×ARC-GFP) and Δp33CTV9R (CTV33-23-I3×ARC-GFP-43) as described above (FIG. 7 A). However, after infection of protoplasts and plants, no GFP fluorescence was observed even though the virus replicated well in both (FIGS. 7B&C).

Poly-Peptide Fusion

Figure 10:
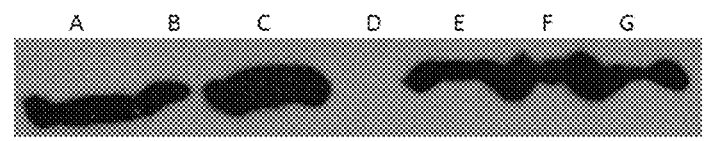
Figure 14:
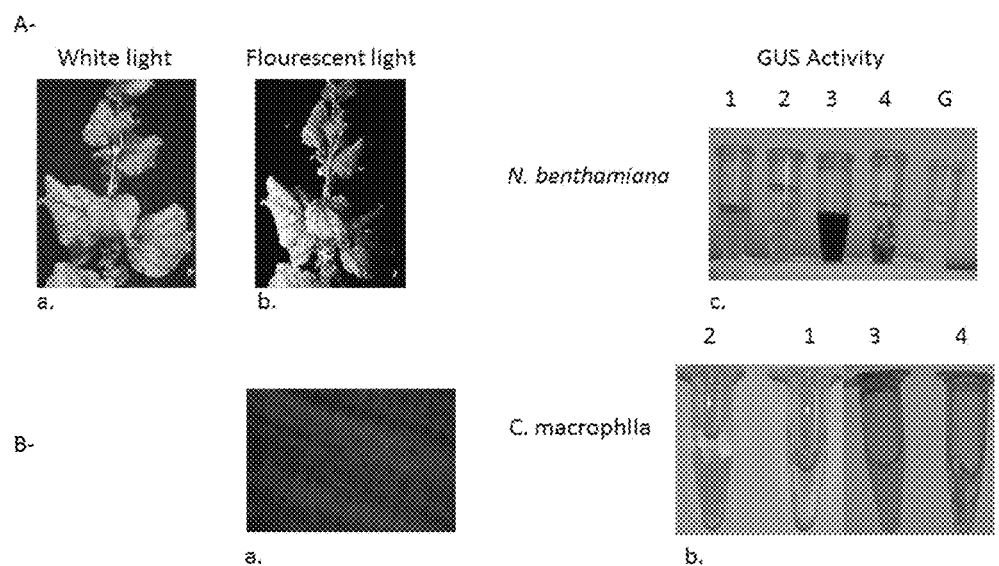

P23, the highest expressed gene of CTV, is a multifunctional protein that is essential for citrus infection. P23 is a silencing suppressor and controls plus to minus RNA ratio in infected cells via an RNA binding domain constituted of positive charged amino acid residues and Zn finger domain present between amino acid 50-86 (Lopez et al., 2000; Satyanarayana et al., 2002b; Lu et al., 2004). In order to create a gene fusion the HC-Pro or NIa protease motifs of TEV were selected to be fused at the C-terminus of p23 (between nts 19017 and 19018) (FIG. 8). The protease recognition sequence of the HC-Pro and NIa was duplicated between p23 and the protease and between the protease and GFP creating vectors CTV33-23-HC-GFP-72 and CTV33-23-NIa-GFP-73, respectively (FIG. 8). The processing of the protease motif from p23 should release the p23 with 7 extra amino acids at its C-terminus in the case of HC-Pro and 6 amino acids in the case of NIa. The GFP protein should have two extra and one extra amino acid after being cleaved from HC-Pro and NIa, respectively. The recognition sequences were switched between HC-Pro and NIa creating vectors CTV33-23-HCØ-GFP-74 and CTV33-23-NIaØ-GFP-75 as controls that are unable to be cleaved (FIG. 8). All the polypeptide fusion vectors were created in CTV binary vectors for infection of plants because in protoplast it was shown that p23 fusion did not affect the ability to replicate and pass between protoplast sets (Tatineni and Dawson, unpublished result). In N. benthamiana infiltrated leaves, all constructs fluoresced similarly to each other and to the free GFP constructs behind p23 (FIG. 9A). Furthermore, western immune-blot analysis from infiltrated leaves indicated a near-perfect processing of the reporter gene from the polypeptide fusion (FIG. 10). The GFP protein did not localize to the nucleus unlike the fusion to p23 without a protease processing releasing the reporter gene. Upon agro-inoculation of plants, only constructs with the protease and its homologous processing sites were able to move systemically into upper non-inoculated leaves. The fluorescence in upper non-inoculated leaves was weaker than those for the expression vectors CTV33-23-BY-GFP-37, CTV33-23-G-GFP-40 and CTV33-23-B-GFP-42 carrying GFP under its own controller element (FIG. 9B). Furthermore, it was easier to visualize fluorescence on the abaxial rather than the adaxial leaf surface (FIG. 9C). Upon inoculation of citrus with construct CTV33-23-HC-GFP-72, one plant became positive with relatively low ELISA value compared to others (Data not presented). The reporter gene activity was not detected.

Example 4: Production of More than One Extra Foreign Protein from CTV Vectors

Use of Single Controller Elements to Express Multiple Proteins

In order to exploit the polypeptide strategy to express multiple genes driven by the same controller element in a CTV based vector, a fusion polypeptide was created consisting of GFP/Protease (Pro)/GUS. Two different protease motifs were used in the different constructs, HC-Pro and NIa, with their proteolytic motifs and recognition sequences separating GFP ORF from the GUS ORF (FIGS. 14A & 3-16) (Carrington and Dougherty, 1988; Carrington et al., 1989). Theoretically, in case the NIa was the protease motif in the fusion, six extra amino acids are coupled with the N-terminal protein (GFP) at its C-terminus whereas only one extra amino acid is added to the N-terminus of GUS. Similarly, where HC-Pro was the protease within the fusion poly-peptide, 7 extra amino acids are added to the C-terminus of GFP and two extra amino acids added to the N-terminus of GUS. The fusion genes ranged in size between 3127 and 3480 nts.

Replacement of p13 Gene

The two fusions of GFP/Pro/GUS described above were engineered into the p13 site of CTV in the agro-inoculation binary vector under the control of the BYSV CP-CE (CTV33-Δ13-BYGFP-HC-GUS-77 with HC-Pro protease motif and CTV33-Δ13-BYGFP-NIa-GUS-78 with NIa protease motif) (FIG. 11A). The constructs were agro-inoculated to N. benthamiana for monitoring the ability to systemically infect the plant and produce GUS and GFP. Both genes were produced based on their assays (FIG. 11B). Western immune-blot analysis indicated the efficient processing of the GFP protein from the polypeptide fusion (FIG. 10). The virus multiplied and spread to high titers in N. benthamiana plants as indicated by symptom development in the upper leaves (FIG. 11B) and ELISA. However, the level of GFP fluorescence was less than that of vectors CTV33-Δ13-BY-GFP-57, CTV33-Δ13-G-GFP-65 and CTV33-Δ13-B-GFP-66 expressing the GFP alone and spread more slowly into the upper non-inoculated leaves than those vectors (Data not presented). In N. benthamiana plants, overlapping fluorescence and enzymatic activity of GUS were demonstrated 7 months after the injection of the construct revealing their stability (FIG. 12).

Insertion Between p23 and 3'NTR

In an attempt to improve the expression level of GFP and GUS, the fusion polypeptide was moved closer to the 3'NTR. The fusion gene with either BYSV, GLRaV-2 or BYV CP-CE with the protease of HC-Pro was inserted between p23 and 3'NTR referred to as CTV33-23-BY-GFP-HC-GUS-51, CTV33-23-G-GFP-HC-GUS-53 and CTV33-23-BY-GFP-HC-GUS-55 whereas with the NIa protease constructs were named, CTV33-23-BY-GFP-NIa-GUS-52, CTV33-23-G-GFP-NIa-GUS-54 and CTV33-23-BY-GFP-NIa-GUS-56, respectively (FIG. 13). After N. benthamiana plants were agro-inoculated, all the constructs multiplied and spread into the upper non-inoculated leaves as indicated by GFP fluorescence (FIG. 14A) and GUS activity (FIG. 14A). Similar to constructs CTV33-$\Delta$13-BYGFP-HC-GUS-77 and CTV33-$\Delta$13-BYGFP-NIa-GUS-78, fluorescence overlapping with GUS enzymatic activity was demonstrated 7 months after injection indicating the stability of the fusion. However, C. macrophylla plants infected with construct CTV33-23-BY-GFP-HC-GUS-51 revealed only faint fluorescence and almost no GUS activity (FIG. 14B) and high ELISA values.

Example 5: Use of Multiple Promoters to Express Foreign Genes Simultaneously

Bimolecular Fluorescence Complementation (BiFC) in CTV.

For examination of the insertion of two CP-CE controlling different ORFs, the BiFC system, which produces visible fluorescence only when the two proteins accumulate in the same cell, was used. This system was developed using the bJun fused to N-terminus of EYFP (A.A. 1-154) (referred to as bJunN) and bFos ORF fused to C-terminus of EYFP (A.A. 155-238) (referred to as bFosC) (Hu et al., 2002).

Figure 15:
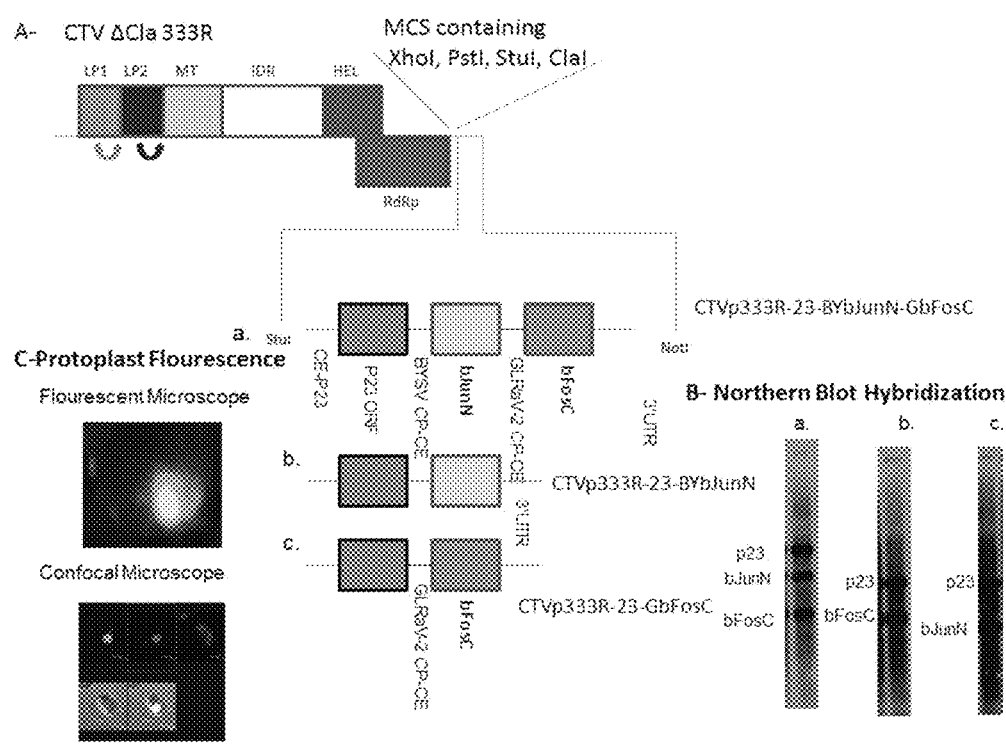

Both proteins are transported to the nucleus where they directly interact enabling the EYFP protein to regain its wild type folding pattern and results in emission of fluorescence upon activation by a blue light source (Excitation wave length is 525 nm and emission wavelength is 575 nm) (Hu et al., 2002). One or both components of BiFC were introduced into the CTV mini-replicon 3' of the p23 ORF (between nts #19020 and 19021 Genbank Accession # AY170468) referred to as CTVp333R-23-BYbJunN, CTVp333R-23-GbFosC and CTVp333R-23-BYbJunN-GbFosC (FIG. 15 A). Northern blot hybridization analysis demonstrates the successful transfection of all three constructs into N. benthamiana protoplast (FIG. 15B). The two transcription factors interacted in the plant cell as demonstrated by nuclear fluorescence observed only in protoplasts infected with CTVp333R-23-BYbJunN-GBFosC (FIG. 15C). It is worth noting that the size of the two inserted genes is approximately identical to that of the GUS ORF.

As a control for the BiFC experiments, the inventors also introduced the genes individually into $\Delta$p33CTV9R behind p23 creating vectors CTV33-23-BYbJunN-97 and CTV33-23-GbFosC-98 so that only one component would be produced (FIG. 16B). Neither construct exhibited fluorescence in the nucleus.

Expression of Multiple Foreign Genes Simultaneously at the Same Location

P13 Replacement.

Both genes were introduced into a $\Delta$p33CTV9R (Satyanarayana et al., 1999, 2000, 2003; Tatineni et al., 2008) as a replacement of the p13 gene (replacement of the nucleotides deleted between 17292 and 17581), resulting in CTV33-$\Delta$13-BYbJunN-GbFosC-76 (FIG. 16A). Transfection of protoplasts with the RNA transcripts of CTV33-$\Delta$13-BYbJunN-GbFosC-76 resulted in the nuclear fluorescence of infected protoplasts (Data not presented). Similarly, infiltrated leaves of N. benthamiana plants with full length CTV33-$\Delta$13-BYbJunN-GbFosC-76 emitted nuclear fluorescence (FIG. 16B). On the contrary, infiltrated leaves with constructs CTV33-23-BYbJunN-97 and CTV33-23-GbFosC-98 did not show any nuclear fluorescence (Data not presented). Monitoring stem phloem and leaf veins of N. benthamiana plants infiltrated with CTV33-$\Delta$13-BYbJunN-GbFosC-76 seven weeks after infiltration revealed fluorescence of the vascular tissue indicating the ability of this construct to systemically infect upper leaves of N. benthamiana (FIG. 16B).

Insertion Between p23 and 3'NTR.

Figure 16:
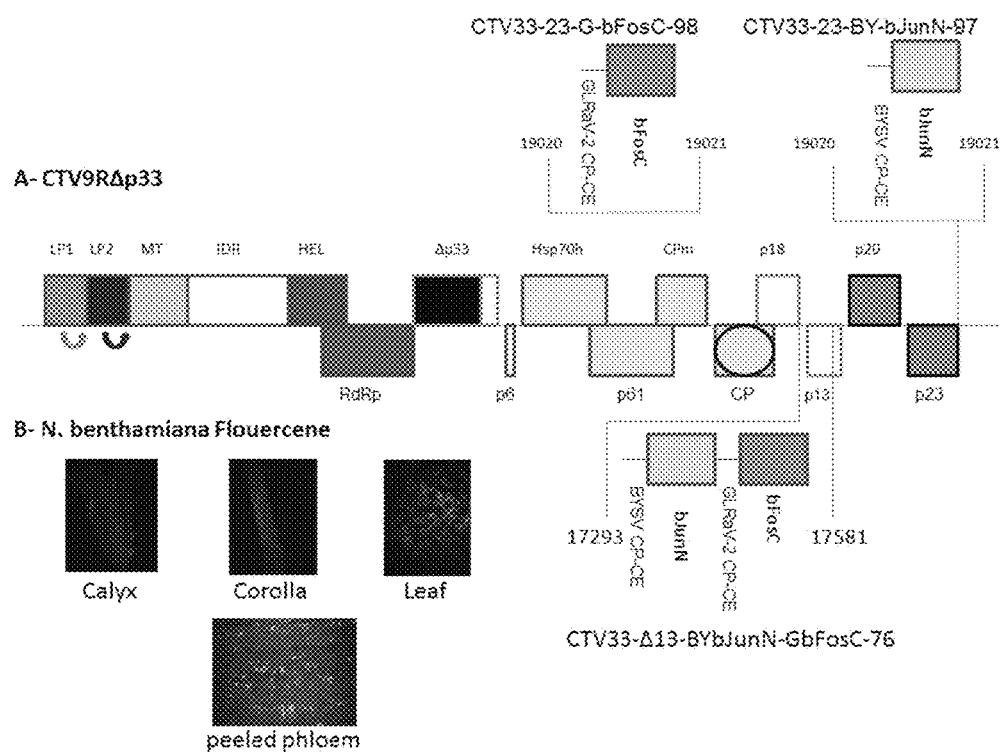
Figure 17:
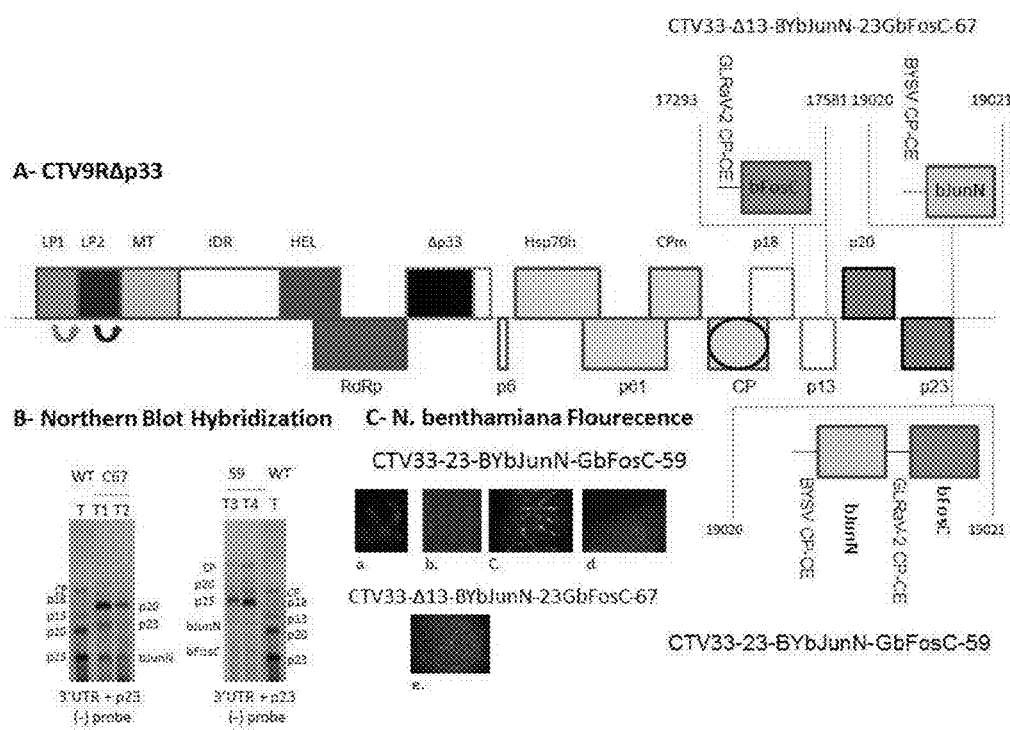

The next step was to examine expression of the two genes when positioned closer to the 3' terminus. The two gene components of the BiFC system were introduced into CTV$\Delta$p33 behind p23 (between nts #19020 and 19021), CTV33-23-BYbJunN-GbFosC-59 (FIG. 3-17A). Upon RNA transfection of construct CTV33-23-BYbJunN-GbFosC-59, nuclear flourescence of infected protoplast was observed under the fluorescent microscope. However, it was difficult to pass the new construct from one protoplast batch to another, similar to GUS and the GFP/Pro/GUS fusion genes inserted at the same location. Upon agro-infiltration of N. benthamiana plants with CTV33-23-BYbJun-GbFosC-59 in full length CTV, fluorescence was observed in infiltrated areas. Systemic symptoms similar to that expected for infection of N. benthamiana by CTV was extremely delayed. However, monitoring upper non-inoculated leaves and phloem tissue of the stem at seven weeks after agro-infiltration of leaves revealed fluorescence of nuclei of the vascular tissue, demonstrating systemic infection by the vector (FIG. 17C). These results confirmed by ELISA, indicate that the position between p23 and 3'NTR can accommodate two extra genes without affecting the ability of CTV to systemically invade the plants. Similar to both genes replacing p13 in construct CTV33-$\Delta$13-BYbJunN-GbFosC-76 there was a delay in the time frame of colonizing the upper vascular tissues by construct CTV33-23-BYbJunN-GbFosC-59. Nuclear fluorescence of systemic stem phloem tissue indicates that CTV33-$\Delta$13-BYbJunN-GbFosC-76 infected more cells than construct CTV33-23-BYbJunN-GbFosC-59 (FIG. 16B & FIG. 17C). This difference in the number of cells infected indicates the better ability of CTV33-$\Delta$13-BYbJunN-GbFosC-76 to move in N. benthamiana as compared to CTV33-23-BYbJunN-GbFosC-59.

Example 6: Expression of Multiple Foreign Genes Simultaneously from Different Locations To express multiple foreign genes from two different positions, the inventors elected to replace the p13 gene and insert a second gene behind p23. CTV33-$\Delta$13-BYbJunN-23-GbFosC-67 (FIG. 17A) was created via replacement of the p13 gene with the BYSV CP-CE driving the bJunN ORF and the GLRaV-2 CP-CE controlling the bFosC ORF inserted between the p23 ORF and the 3'NTR. CTV33-Δ3-BYbJunN-23-GbFosC-67 was transfected into protoplasts and Northern blot analysis revealed the replication of the virus (FIG. 17B). However, accumulation of the p23 mRNA was greatly reduced. CTV33-Δ13-BYbJunN-23-GbFosC-67 was agro-inoculated into *N. benthamiana*. The infiltration into the leaves indicated nuclear fluorescence of infected cells (FIG. 17C) which were much fewer in number compared to constructs CTV33-Δ13-BYbJunN-GbFosC-76 and CTV33-23-BYbJunN-GbFosC-59. Isolation of virions from leaves and transfection of protoplast was carried out resulting in nuclear fluorescence of infected protoplast indicating the successful formation of biologically active virions. However, systemic infection was not achieved in *N. benthamiana* as indicated by the lack of nuclear fluorescence in the stem and upper non-inoculated leaves of *N. benthamiana* and confirmed by ELISA.

Figure 18:
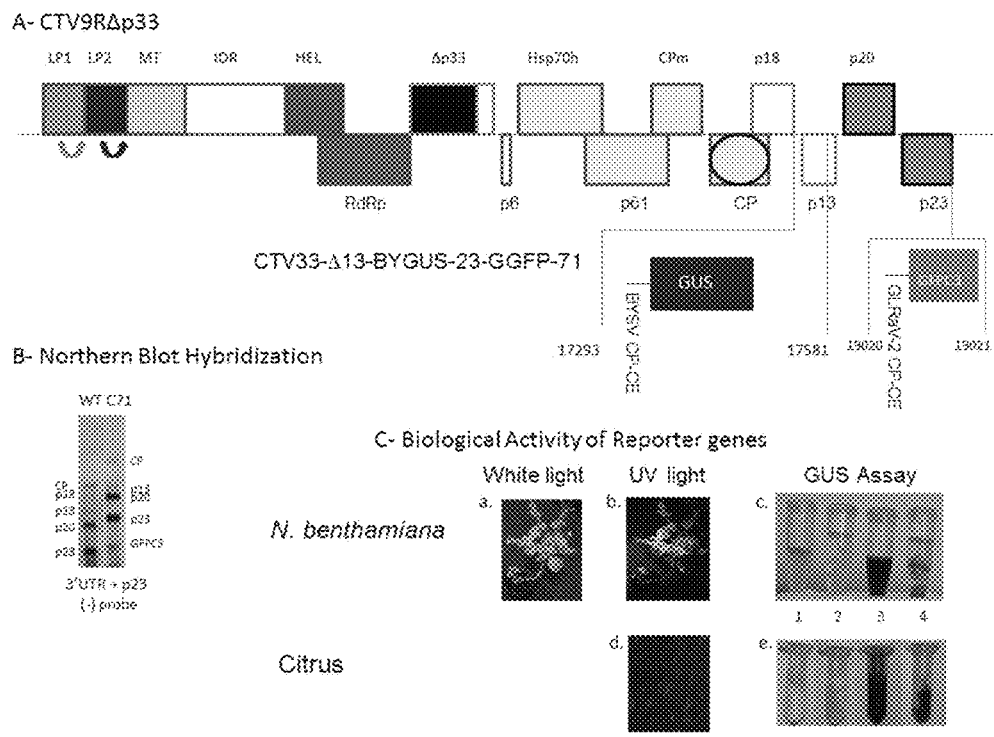

In order to further study simultaneous multiple gene expression from the different locations as above, CTV33-Δ13-BYGUS-23-GGFP-71 was engineered such that the GUS ORF under the control of the BYSV CP-CE replaced the p13 gene(nts 17292-17582) and the GFP ORF under the control of the GLRaV-2 CP-CE was inserted between the p23 and 3'NTR (nts 19020 and 19021) (FIG. 18A). RNA transcripts of CTV33-Δp13-BYGUS-23-GGFP-71 were transfected into *N. benthamiana* protoplasts and northern blot analysis indicated efficient replication of the construct in protoplasts (FIG. 18B). Leaf infiltration of *N. benthamiana* plants with construct CTV33-Δp13-BYGUS-23-GGFP-71 resulted in replication of the virus as indicated by visible fluorescence under a UV light and by GUS activity (Data not presented). The agro-inoculated plants began to exhibit GUS activity and fluorescence in the upper non-inoculated leaves 6 weeks after infiltration (FIG. 3-18C). The systemic infection of upper leaves was slightly slower than constructs with only GFP alone. Also, the phenotype of vein clearing followed by necrosis associated with CTV infection of *N. benthamiana* vascular tissue occurred later than that of single gene vectors. The level of fluorescence when observed UV light appeared to be slightly less than that of the single gene constructs. However, the GFP fluorescence was more in plants infected with construct CTV33-Δp13BYGUS-23GGFP-71, which was controlled by its own CE, compared to that of the fusion in constructs (CTV33-23-BY-GFP-HC-GUS-51, CTV33-23-BY-GFP-NIa-GUS-52, CTV33-23-G-GFP-HC-GUS-53, CTV33-23-G-GFP-NIa-GUS-54, CTV33-Δ13-BYGFP-HC-GUS-77 and CTV33-Δ13-BYGFP-NIa-GUS-78). The activity of both genes continued until the death of the *N. benthamiana* plants. Similarly, in *citrus* the expression of both genes were better than the same genes in constructs CTV33-Δ13-BYGFP-NIa-GUS-78 and CTV33-23-BY-GFP-HC-GUS-51.

Example 7: Level of Foreign Gene Expression of the Different Constructs in *Citrus*

It is difficult to directly compare foreign gene expression from the different vectors in *citrus* due to the differences in the times of infection, the ages of the tissue and the effects of the inserted foreign gene cassette on the replication of the virus. Yet, protein presence in *citrus* is the best measure of expression level. Thus, western blot analysis was used to compare the relative level of expression of the different GFP and GUS constructs in *citrus* to that of CP protein, a house keeping gene to determine the replication levels. Western blots using the GFP antibodies and the CP antibody revealed a trend which confirms the relative higher expression levels near the 3' end of the genome and a lower expression level when the inserted gene is moved further away from the 3' end with the exception for the insertion between p13 and p20 (FIG. 19A). In contrary, the GUS expression in *citrus* revealed a higher relative expression level as replacement of p13 rather than insertion behind p23 (FIG. 19B).

Example 8: Multiple Gene Vectors

Plasmid Construction:

Three and four gene vectors were developed by introducing different combination of gene cassettes into the CTV genome at different locations. Three of the vectors were developed in CTV9RΔp33 in the pCAMBIA 1380 background (CTV33-BGFP-BYGUS-GTMVCP-79, CTV33-BGFP-GbFosC-BYbJunN-81 and CTV33-Δ13-BGFP-BYbJunN-GbFosC-82). The other three gene vectors (CTV-BASL-BYPTA-CP7-119, CTV-BASL-BYP10-CP7-131, CTV-BASL-BYPTA-CP10-120 and CTV-BRFP-BYGFP-CTMVCP-117) and one four gene vector (CTVΔ13-BRFP-GbFosC-BYbJunN-CTMVCP-118) were developed by modifying CTV9R in the background of pCAMBIA1380 altered by replacing the hygromycin ORF with the p22 ORF of Tomato chlorosis virus. For the ease of cloning the PstI restriction site in p33 ORF in full length CTV9R was eliminated by introducing a silent mutation using overlap extension PCR using primers 1749 and 1750 in combination with primer C-1436 and C-253 followed by digestion of both the overlap PCR product and CTV9R with XmaI and PmeI. Most of the gene cassettes were introduced into their locations by overlap extension PCR using the primers listed in table 1. The only exception was the insertion of green fluorescent protein cycle 3 in between the CPm and CP gene. Introducing the GFPC3 gene cassette into that location was done by restriction digestion of 9-47RGFP plasmid and point mutated CTV9R in pCAMBIA1380 with PmeI and PstI.

Expression of Three and Four Foreign Genes Simultaneously

After successfully expressing two genes in *N. benthamiana* and *citrus* with one and two different controller elements we are building vectors to express three and four foreign genes from three and four different controller elements, respectively. The reporter genes used in different combinations were the green fluorescent protein (cycle 3 GFP, GFPC3), red fluorescent protein (tag red fluorescent protein, RFP), Bimolecular fluorescence complementation using the bFos and bJun mammalian transcription factors (Hu et al., 2002), β-glucuronidase (GUS) gene from *Escherichia coli* and the Tobacco mosaic virus (TMV) coat protein gene (CP). Similarly, three gene vectors were built in different combinations to express two antimicrobial peptides (AMPs) from *Tachypleus tridentatus* and *Sus scorfa*, *Allium sativum* lectin (ASL) and *Pinellia ternata* agglutinin (PTA). The three gene vectors were either expressed from two or three locations within the CTV genome Expression of Three Foreign Genes from Three Different Locations Simultaneously:

Six vectors were built to express three foreign genes from three different locations. The vectors were built to express the genes either from CTV9RΔp33 or full length CTV9R.

Vectors Built to Express Three Genes from Three Different Locations in CTV9RΔp33

Two vectors were built by inserting the three extra gene cassettes into CTV9RΔp33 creating expression vectors CTV33-BGFP-BYGUS-GTMVCP-79 (FIG. 26) and CTV33-Δ13-BGFP-BYbJunN-GbFosC-82 (FIG. 28). CTV33-BGFP-BYGUS-GTMVCP-79 expresses the three ORFs of GFP (insertion between CPm and CP), GUS (insertion between p13 and p20) and the coat protein of TMV (insertion between p23 and 3'UTR) under the CP-CE of BYV, BYSV and GLRaV-2, respectively. CTV33-Δ13-BGFP-BYbJunN-GbFosC-82 expresses the three ORFs of GFP (insertion between CPm and CP), bJunN ORF (replacement of p13) and bFosC (insertion between p23 and 3'UTR) under the CP-CE of BYV, BYSV and GLRaV-2, respectively. The two vectors were infiltrated into *N. benthamiana* leaves in combination with silencing suppressors and inoculated into *citrus* using the procedure of Gowda et al., 2005. As leaves were cut and grinded to isolate virions over 70% sucrose cushion gradient just 5 days after infiltration into the *N. benthamiana* leaves it was not likely that these plants will get systemically infected, thus they were discarded. The fluorescence of infiltrated leaves under hand held UV indicated the expression of the GFP protein in both CTV33-BGFP-BYGUS-GTMVCP-79 and CTV33-Δ13-BGFP-BYbJunN-GbFosC-82 indicating the ability of the created vector to replicate in the *N. benthamiana* leaves. Electron microscope grids prepared from leaf dips of infiltrated *N. benthamiana* leaves for construct CTV33-BGFP-BYGUS-GTMVCP-79 and CTV33-Δ13-BGFP-BYbJunN-GbFosC-82 indicated the formation of virions a prerequisite for the successful mechanical inoculation of *citrus* seedlings with CTV. Furthermore, in the case of CTV33-BGFP-BYGUS-GTMVCP-79 and not CTV33-Δ13-BGFP-BYbJunN-GbFosC-82 there was the formation of rod-shaped structures referred to as TMV pseudo-virions a characteristic of the expression of the TMV coat protein.

Vectors Built to Express Three Genes from Three Different Locations in CTV9R

Four vectors were built to express three foreign genes from the same three different locations within the CTV genome. The three locations selected were insertion between CPm and CP, p13 and p20 and p23 and 3'UTR. For the ease of cloning into the full length CTV infectious clone a the PstI site within the p33 ORF was eliminated by introducing a silent point mutation by overlap extension PCR. Three of the four vectors were created by using different combinations of the two AMPs, ASL and PTA resulting in expression vectors CTV-BASL-BYPTA-CP7-119, CTV-BASL-BYP10-CP7-131 and CTV-BASL-BYPTA-CP10-120. The fourth vector named CTV-BRFP-BYGFP-CTMVCP-117 was created by inserting the ORFs of GFP, RFP and TMV CP under the control of BYV, BYSV and duplicated CP-CE of CTV. All the vectors were infiltrated into *N. benthamiana* to monitor the development of systemic infection. CTV-BASL-BYPTA-CP7-119 developed efficient systemic infection in 1 *N. benthamiana* plant. Plants infiltrated with vector CTV-BRFP-BYGFP-CTMVCP-117 revealed fluorescence in systemic leaves under hand held UV. Upon development of pronounced systemic infection, virions from CTV-BRFP-BYGFP-CTMVCP-117 will be concentrated over a sucrose step gradient and a sucrose cushion in order to inoculate *citrus* plants similar to the procedure recently followed for vector CTV-BASL-BYPTA-CP7-119

Expression of Three Foreign Genes from Two Different Locations Simultaneously:

Two vectors were created for the simultaneous expression of three genes from two different locations within the CTV genome. One vector was built in CTV9RΔp33 creating expression vector CTV33-BGFP-GbFosC-BYbJunN-81 whereas the other vector was built in full length CTV9R named CTVΔ13-GbFosC-BYbJunN-CTMVCP-129.

Vector Built to Express Three genes from Two different locations in CTV9RΔp33:

CTV33-BGFP-GbFosC-BYbJunN-81 (FIG. 27) was engineered through modifying CTV9RΔp33 by inserting a single gene cassette between CPm and CP (GFP ORF under the control of BYV CP-CE) and a double gene cassette (bFosC ORF followed by bJunN ORF under the control of GLRaV-2 and BYSV CP-CE, respectively) as an insertion between p23 and 3'UTR. A 1:1 mixture of 4 different silencing suppressors and CTV33-BGFP-GbFosC-BYbJunN-81 were infiltrated into *N. benthamiana* leaves. Electron microscopy from grids of leaf dips revealed the formation of virions similar to constructs CTV33-BGFP-BYGUS-GTMVCP-79 and CTV33-Δ13-BGFP-BYbJunN-GbFosC-82. In addition, the infiltrated leaves revealed strong fluorescence under hand held UV light. Infiltrated leaves were used to concentrate virions on a 70% sucrose cushion in an attempt to infect *citrus* seedlings.

Vector Built to Express Three genes from Two different locations in CTV9R:

CTV9R was modified by inserting a double gene cassette (bFosC ORF followed by bJunN ORF under the control of GLRaV-2 and BYSV CP-CE, respectively) as replacement of p13 and a gene cassette (TMV CP ORF under the control of the duplicated CP-CE) as an insertion between p23 and 3'UTR creating expression vector CTVΔ13-GbFosC-BYbJunN-CTMVCP-129 (FIG. 21). This vector is recently infiltrated into *N. benthamiana* leaves. After systemic infection of *N. benthamiana* the virions will be concentrated to enable the inoculation of *citrus* plants.

Expression of Four Foreign Genes from Three Different Locations Simultaneously:

In order to build the four gene vector we used four gene cassettes located at three different locations within the CTV genome. The RFP ORF was introduced between CPm and CP under the control of the BYV CP-CE, the two BiFC components bFosC and bJunN under the control of GLRaV-2 and BYSV respectively were introduced as a replacement of the p13 gene and the TMV ORF under the control of the duplicated CP-CE of CTV was introduced behind p23. The four gene vector named CTVΔ13-BRFP-GbFosC-BYbJunN-CTMVCP-118 was infiltrated into the *N. benthamiana* leaves for the development of systemic infection. Upon systemic infection virion concentration will be carried out over a sucrose step gradient and cushion for the infection of the *citrus* trees.

Discussion Related to Examples 1-8

In this work, CTV constructs that are extraordinarily permissive in allowing insertion of foreign sequences at different places in the 3' portion of the genome are disclosed. Numerous different potential vector constructs to express foreign genes via additional subgenomic RNAs, di-cistronic mRNAs, or protease processing of fusion proteins were created and examined. Remarkably, most of these constructs functioned as vectors. Additionally, that the CTV constructs disclosed herein are capable of simultaneously producing large amounts of multiple foreign proteins or peptides.

The ultimate goal was to develop high expressing and stable vectors for the natural CTV host, *citrus*. Thus, virions were concentrated from *N. benthamiana* plants infected with 12 different constructs that spread and expressed moderate to high levels of the foreign protein(s) and used to inoculate *citrus*. *C macrophylla* plants became positive for infection between 6-60 weeks after inoculation depending on the insert length in the virus and the amount of virions concentrated from the *N. benthamiana* leaves that were used for inoculation. Most of the constructs that infected *citrus* produced moderate levels of the reporter gene/s.

Several approaches were examined for expression of foreign genes from CTV. The first approach was the "add-a-gene" strategy that involved the addition or duplication of a controller element and an additional ORF, which resulted in an additional subgenomic RNA. The "add-a-gene" approach was developed initially in TMV via duplicating the CP subgenomic promoter controlling a foreign gene (Dawson et al., 1989; Donson et al., 1991; Shivprasad et al., 1999). An advantage of this strategy is that it expresses the exact protein with no additional amino acids added to the N or/and C terminus which could affect its biological activity, at relatively high levels. However, there are limitations of this strategy that should be considered. Duplication of the controller element can lead to homologous recombination resulting in the loss of the gene of interest (Chapman et al., 1992; Dawson et al., 1989). Although this made the TMV insert unstable, it appeared to have little effect on the stability in CTV (Folimonov et al., 2007). The use of a heterologous controller element from related viruses stabilized the TMV insertions. However, heterologous controller elements usually are differentially recognized by the replicase complex of the virus (Folimonov et al., 2007; Shivprasad et al., 1999). This observation can be utilized to regulate the levels of desired gene expression (Shivprasad et al., 1999). An important consideration is that there can be competition between the different subgenomic RNAs of a virus. With TMV, the extra gene competed with the coat protein gene and the movement gene. There appeared to be a maximal capacity for production of subgenomic RNAs that was divided among the three RNAs. Manipulations that resulted in increases in one resulted in decreases in the others. One solution was to reduce coat protein production to allow optimal foreign gene and movement gene expression (Shivprasad et al., 1999; Girdishivelli et al., 2000). Yet, CTV subgenomic mRNAs appeared to be much less competitive (Folimonov et al., 2007; Ayllón et al., 2003).

In previous work, a CTV vector was created that expressed an extra gene between the CP and CPm genes that was an effective and stable vector in *citrus* trees. The foreign gene was in position 6 from the 3' terminus (Folimonov et al., 2007). The position of the extra gene was chosen arbitrarily. Here the inventors continued vector design in an attempt to define the limits of manipulation of the CTV genome in producing extra proteins or peptides. The virus expresses its ten 3' genes via sg mRNAs (Hilf et al., 1995). One rule of CTV gene expression is that genes nearer the 3' terminus are transcribed higher than internal genes. For example, transcription of the p33 gene, which is at position 10 from the 3' terminus, is very low in its native position, but transcription became very high when the p33 gene was moved near the 3' terminus (Satyanarayana et al., 1999). Thus, expression of foreign genes from positions nearer the 3' terminus might result in higher levels than from the position 6 arbitrarily chosen in the first vector (Folimonov et al., 2007). Yet, based on results from other viruses, only certain positions within the viral genome are likely to tolerate extra gene insertions. For example, with TMV or Alfalfa mosaic virus the location between CP and 3'NTR did not accommodate an insert (Dawson et al., 1989; Lehto and Dawson, 1990; Sanchez-Navarro et al., 2001). Remarkably, almost all of the constructs with insertions in CTV within the p13 deletion, between p13 and p20, and between p23 and the 3' NTR were viable. In contrast, it was found that the only position the virus did not tolerate insertions was between the p20 and p23 genes. It is possible that these insertions interfered with the transcription of either of the adjacent genes.

Another strategy to express foreign genes in a viral vector consists of in-frame fusion of an ORF of interest to a viral ORF at either the N or C terminus. The two proteins can be released by engineering a protease and processing sites between the two proteins (Dolja et al., 1997; Gopinath et al., 2000). It was first adapted in the potyviridae, tobacco etch virus (Dolja et al., 1992). The major advantage of polyprotein fusion strategy is that the foreign protein is expressed in 1:1 ratio with the viral protein. A major limitation is that this process adds extra amino acids at the N and/or C termini of both proteins, which may affect their biological activities.

A series of constructs utilizing the HC-Pro or NIa proteases from potyviruses to enable post translational processing of the engineered polyprotein to release free GFP, protease, and the p23 protein were created. These vectors were able to systemically infect *N. benthamiana*. The systemic movement of these constructs was slower than the expression vector constructs containing only the GFP ORF as an extra gene. The slower systemic movement and the lower levels of GFP expression in the systemic leaves partially could be attributed to the extra C-terminal amino acids of p23 reduced its activity in RNA silencing suppression or amplification of viral RNAs or the protease processing delayed its activity. Although these constructs did not produce the maximal levels of foreign protein, they were viable vectors expressing substantial amounts of GFP.

Upon identifying the locations within the CTV genome that could accommodate foreign gene inserts, strategies were designed to construct viral vectors that express multiple genes. The first strategy depended on the use of a single controller element driving the transcription of a polypeptide gene. The fusion gene that consisted of GFP/Pro/GUS, ranged in size from 3127 nts to 3480 nts. Other strategies utilized two extra CEs to produce two extra sg RNAs simultaneously. This strategy gave the flexibility to insert the two genes in tandem in the same location or in two different locations. Both strategies worked.

Heterologous protein expression in whole plant is usually accomplished by development of transgenic plants by insertion of foreign DNA into the plastid or nuclear genome. Plastid transformation has been successful for only a few annual crops. Time and success of nuclear transformation varies among the different crops. Certain plants are more recalcitrant to transformation and subsequent regeneration than others. There are other disadvantages, particularly in perennial crops. For example, *citrus* has a long juvenile stage after regeneration that prolongs the time necessary to evaluate the horticultural characteristics and delays the time to commercial use. Another major disadvantage is that transformation is limited to the next generation of plants.

The inventors have now developed a series of different CTV vectors, each with different characteristics that are more effective under specific conditions. For example, with the "add-a-gene" vectors, the inventors would advocate the expression of a small gene in 3' of the p23 gene in CTV for maximal expression. A medium gene could be more efficiently expressed from within the p13 area. A large gene probably would be better accommodated as an insertion between CP and CPm where it would disrupt the viral subgenomic RNAs less and result in better systemic invasion of the plant. For expression of smaller proteins, peptides, or RNAs to target RNA silencing, it is possible that the virus could accommodate 3 or 4 different genes. Different combinations of extra sg RNAs and protease processing can be chosen. Although two foreign proteins have been produced from other viruses, CTV is unique in usefulness because of its stability. The original vector has been continuously producing GFP for 8 years.

The uses of the CTV based expression vector have evolved since its inception. It was initially developed as a laboratory tool for *citrus* improvement. The vector was designed to express potential genes for transformation of *citrus*. Results of the effect of the heterologous gene in *citrus*, particularly if the effect was expected in mature tissue or fruit, could be obtained by the virus years before results would come from direct transformation. However, conditions and needs of the *citrus* industry have changed due to the invasion of a new bacterial disease referred to as Huanglongbing (HLB). This disease has spread so rapidly and is so damaging that the survival of the *citrus* industry is threatened. Initially, the CTV vector was used to identify antimicrobial peptides with activity against the HLB bacterium for transformation into *citrus*. However, the disease is spreading so rapidly that transgenic plants may not be available in time to save the industry. Due to the remarkable stability, the CTV vector now is being considered for use in the field to protect *citrus* trees and to treat infected trees until resistant transgenic plants become available. The CTV vector as a tool in the field to fight an invading disease of *citrus* is only one example of what viral vectors can do for agriculture. The possibilities are many for very stable vectors like those of CTV and perennial crops, particularly trees. Many trees are productive for 100 years or more. During the lifespan of the trees technologies changes and disease and pest pressures change. To improve trees by traditional transformation methods requires removing all of the present trees from the field and replanting. The use of a viral vector could add new genes to the existing trees.

LIST OF REFERENCES

Ahlquist, P., French, R., Janda, M., Loesch-Fries, L. S., 1984. Multi component RNA plant virus infection derived from cloned viral cDNA. Proc. Natl. Acad. Sci. USA 8, 7066-7070.

Akbergenov, R, Zhanybekova, S., Kryldakov, R. V., Zhigailov, A., Polimbetova, N. S., Hohn, T., Iskakov, B. K., 2004. ARC-1, a sequence element complementary to an internal 18S rRNA segment, enhances translation efficiency in plants when present in the leader or intercistronic region of mRNAs. Nucleic Acids Res. 32, 239-247.

Allison, R. F., Dougherty, W. G., Parks, T. D., Willis, L., Johnston, R. E., Kelly, M., Armstrong, F. B., 1985. Biochemical analysis of the capsid protein gene and capsid protein of tobacco etch virus: N-terminal amino acids are located on the virion's surface. J. Virol. 147, 309-316.

Andrade, M., Sato, M., Uyeda, I., 2007. Two resistance modes to Clover yellow vein virus in pea characterized by a green fluorescent protein-tagged virus. Phytopathology 97, 544-550.

Ayllón, M. A., Gowda, S., Satyanarayana, T., Karasev, A. V., Adkins, S., Mawassi, M., Guerri, J., Moreno, P., Dawson, W. O., 2003. Effects of modification of the transcription initiation site context on *citrus tristeza* virus subgenomic RNA synthesis. J. Virol. 77, 9232-9243.

Balvay, L., Soto Rifo, R., Ricci, E. P., Decimo, D., Ohlmann, T., 2009. Structural and functional diversity of viral IRESes. Biochim. Biophys. Acta 1789, 542-557.

Baulcombe, D. C., Chapman, S., Santa Cruz, S., 1995. Jellyfish green fluorescent protein as a reporter for virus infections. Plant J. 7, 1045-1053.

Beauchemin, C., Bougie, V., Laliberte, J. F., 2005. Simultaneous production of two foreign proteins from a potyvirus-based vector. Virus Res. 112, 1-8.

Brisson, N., Paszkowski, J., Penswick, J. R., Gronenborn, B., Potrykus, I., Hohn, T., 1984. Expression of a bacterial gene in plants by using a viral vector. Nature 310, 511-514.

Canizares, C. M., Navas-Castillo, J., Moriones, E., 2008. Multiple suppressors of RNA silencing encoded by both genomic RNAs of the crinivirus, Tomato chlorosis virus. Virology 379, 168-174.

Canizares, M. C., Nicholson, L., Lomonossoff, G. P., 2005 Use of viral vectors for vaccine production in plants. Immunol. Cell Biol. 83, 263-270.

Canto, T., Prior, D. A. M., Hellwald, K.-H., Oparka, K. J., Palukaitis, P., 1997. Characterization of cucumber mosaic virus IV. Movement protein and coat protein are both essential for cell-to-cell movement of cucumber mosaic virus. Virology 237, 237-248.

Carrasco, P., Daros, J. A., Agudelo-Romero, P., Elena, S. F., 2007. A real-time RT-PCR assay for quantifying the fitness of tobacco etch virus in competition experiments. J. Virol. Methods 139, 181-188.

Carrington, J. C., Cary, S. M., Parks, T. D. and Dougherty, W. G., 1989. A second proteinase encoded by a plant potyviral genome. EMBO J. 8, 365-370.

Carrington, J. C., Dougherty, W. G., 1988. A viral cleavage site cassette: Identification of amino acid sequences required for tobacco etch virus polyprotein processing. Proc. Natl. Acad. Sci. USA 85, 3391-3395.

Chalfie, M., Tu, Y., Euskirchen, G., Ward, W. W., Prasher, D. C., 1994. Green fluorescent protein as a marker for gene expression. Science 263, 802-805.

Chapman, S., Kavanagh, T., Baulcombe, D., 1992. Potato virus X as a vector for gene expression in plants. Plant J. 2, 549-557.

Chiba, M., Reed, J. C., Prokhnevsky, A. I., Chapman, E. J., Mawassi, M., Koonin, E. V., Carrington, J. C., Dolja, V. V., 2006. Diverse suppressors of RNA silencing enhance agroinfection by a viral replicon. Virology 346, 7-14.

Crameri, A., Whitehorn, E. A., Tate, E., Stemmer, W. P., 1996. Improved green fluorescent protein by molecular evolution using DNA shuffling. Nat. BioTechniques 14, 315-319.

Dawson, W. O., Bubrick, P., Grantham, G. L. 1988. Modifications of the tobacco mosaic virus coat protein gene affect replication, movement, and symptomatology. Phytopathology 78, 783-789.

Dawson, W. O., Lewandowski, D. J., Hilf, M. E., Bubrick, P., Raffo, A. J., Shaw, J. J., Grantham, G. L. Desjardins, P. R., 1989. A tobacco mosaic virus-hybrid expresses and loses an added gene. Virology 172, 285-292.

Deleris, A., Gallego-Bartolome, J., Bao, J., Kasschau, K. D., Carrington, J. C., Voinnet, O., 2006. Hierarchical action and inhibition of plant Dicer-like proteins in antiviral defense. Science 313, 68-71.

Dietrich, C., Maiss, E., 2003. Fluorescent labeling reveals spatial separation of potyvirus populations in mixed infected *Nicotiana benthamiana* plants. J. Gen. Virol. 84, 2871-2876.

Dolja, V. V., Hong, J., Keller, K. E., Martin, R. R., Peremyslov, V. V., 1997. Suppression of potyvirus infection by co-expressed closterovirus protein. Virology 234, 243-252.

Dolja, V. V., McBride, H. J., Carrington, J. C., 1992. Tagging of plant potyvirus replication and movement by insertion of beta-glucuronidase into the viral polyprotein. Proc. Natl. Acad. Sci. USA 89, 10208-10212.

Donson, J., Kearney, C. M., Hilf, M. E., Dawson, W. O. 1991. Systemic expression of a bacterial gene by a tobacco mosaic virus-based vector. Proc. Natl. Acad. Sci. USA. 88, 7204-7208.

Dorokhov, Y. L., Skulachev, M. V., Ivanov, P. A., Zvereva, S. D., Tjulkina, L. G., Merits, A., Gleba, Y. Y., Hohn, T., Atabekov, J. G., 2002. Polypurine (A)-rich sequences promote cross-kingdom conservation of internal ribosome entry. Proc. Natl. Acad. Sci. USA. 99, 5301-5306.

Edelstein, M. L., Abedi, M. R. Wixon, J., 2007. Gene therapy clinical trials worldwide to 2007—an update. J. Gene Med. 9, 833-842.

Fernandez-Miragall, O., Lopez de Quinto, S., Martinez-Salas, E., 2009. Relevance of RNA structure for the activity of picornavirus IRES elements. Virus Res. 139, 172-182.

Fitzgerald, K. D., Semler, B. L., 2009. Bridging IRES elements in mRNAs to the eukaryotic translation apparatus. Biochim. Biophys. Acta 1789, 518-528.

Folimonov, A. S., Folimonova, S. Y., Bar-Joseph, M., Dawson, W. O., 2007. A stable RNA virus-based vector for citrus trees. Virology 368, 205-216.

Folimonova, S. Y., Folimonov, A. S., Tatineni, S., Dawson, W. O., 2008. Citrus tristeza virus: survival at the edge of the movement continuum. J. Virol. 82, 6546-6556.

Folimonova, S. Y., Robertson, C. J., Shilts, T., Folimonov, A. S., Hilf, M. E., Garnsey, S. M. Dawson, W. O., 2010. Infection with strains of Citrus tristeza virus does not exclude super infection by other strains of the virus. J. Virol. 84, 1314-1325.

French, R., Janda, M., Ahlquist, P., 1986. Bacterial gene inserted in an engineered RNA virus: efficient expression in monocotyledonous plant cells. Science 231, 1294-97

Fütterer, J., Bonneville, J. M., Hohn, T., 1990. Cauliflower mosaic virus as a gene expression vector for plants. Physiol. Plant. 79, 154-157.

Gallie, D. R., 2001. Cap-independent translation conferred by the 5' leader of tobacco etch virus is eukaryotic initiation factor 4G dependent. J. Virol. 75, 12141-12152.

Gallie, D. R., Tanguay, R. L., Leathers, V., 1995. The tobacco etch viral 5' leader and poly(A) tail are functionally synergistic regulators of translation. Gene 165, 233-238.

Garnsey, S. M., Gonsalves, D., Purcifull, D. E., 1977. Mechanical transmission of citrus tristeza virus. Phytopathology 67, 965-968.

Garnsey, S. M., Cambra, M., 1991. Enzyme-linked immunosorbent assay (ELISA) for citrus pathogens. In: Roistacher, C. N. (Ed.), Graft-Transmissible Diseases of Citrus, Handbook for Detection and Diagnosis. FAO, Rome, pp. 193-216.

Garnsey, S. M., Henderson C. T., 1982. Extraction, centrifugation, and assay techniques for purification of intact citrus tristeza virus. Workshop on Plant Virus Detection, Agric. Exp. Stn., University of Puerto Rico, Rio Piedras, Mar. 29-Apr. 2, 1982, 106-112.

Giritch, A., Marillonnet, S., Engler, C., van Eldik, G., Botterman, J., Klimyuk, V., Gleba, Y., 2006. Rapid high-yield expression of full-size IgG antibodies in plants coinfected with noncompeting viral vectors. Proc. Natl. Acad. Sci. USA 103, 14701-14706.

Gleba, Y., Klimyuk, V., Marillonnet, S., 2007. Viral vectors for the expression of proteins in plants. Curr. Opin. Biotechnol. 18, 134-141.

Gopinath, K., Wellink, J., Porta, C., Taylor, K. M., Lomonossoff, G. P., van Kammen, A., 2000. Engineering cowpea mosaic virus RNA-2 into a vector to express heterologous proteins in plants. Virology 267, 159-173.

Gowda, S., Satyanarayana, T., Ayllón, M. A., Albiach-Marti, M. R., Mawassi, M., Rabindran, S., Garnsey, S. M., Dawson, W. O., 2001. Characterization of the cis-acting elements controlling subgenomic mRNAs of citrus tristeza virus: production of positive- and negative-stranded 3'-terminal and positive-stranded 5'-terminal RNAs. Virology 286 1, 134-151.

Gowda, S., Satyanarayana, T., Davis, C. L., Navas-Castillo, J., Albiach-Marti, M. R., Mawassi, M., Valkov, N., Bar-Joseph, M., Moreno, P., Dawson, W. O., 2000. The p20 gene product of Citrus tristeza virus accumulates in the amorphous inclusion bodies. Virology 274, 246-254.

Gowda, S., Satyanarayana, T., Robertson, C. J., Garnsey, S. M., Dawson, W. O., 2005. Infection of citrus plants with virions generated in Nicotiana benthamiana plants agroinfiltrated with a binary vector based Citrus tristeza virus, p. 23-33. In M. E. Hilf, N. Duran-Vila, and M. A. Rocha-Pěna (eds.), Proceedings of the 16th Conference of the International Organization of Citrus Virologists. IOCV, Riverside, Calif., 728 USA.

Grdzelishvili, V. Z., Chapman, S. N., Dawson, W. O., Lewandowski, D. J., 2000. Mapping of the Tobacco mosaic virus movement protein and coat protein subgenomic RNA promoters in vivo. Virology 275, 177-192.

Gronenborn, B., Gardner, R. C., Schaefer, S., Shepherd, R. J., 1981. Propagation of foreign DNA in plants using cauliflower mosaic virus as vector. Nature 294, 773-76.

Hagiwara, Y., Peremyslov, V. V., Dolja, V. V., 1999. Regulation of closterovirus gene expression examined by insertion of a self-processing reporter and by northern hybridization. J. Virol. 73, 7988-7993.

Hilf, M. E., Karasev, A. V., Pappu, H. R., Gumpf, D. J., Niblett, C. L., Garnsey, S. M., 1995. Characterization of citrus tristeza virus subgenomic RNAs in infected tissue. Virology 208, 576-582.

Horton, R. M., Hunt, H. D., Ho, S. N., Pullen, J. R., Pease, L. B., 1989. Engineering hybrid genes without the use of restriction enzymes: gene splicing by overlap extension. Gene 77, 61-68.

Hu, C. D., Chinenov, Y., Kerppola, T. K., 2002. Visualization of interactions among bZIP and Rd family proteins in living cells using bimolecular fluorescence complementation. Molecular Cell 9, 789-798.

Ion-Nagy, L., Lansac, M., Eyquard, J. P., Salvador, B., Garcia, J. A., Le Gall, O., Hernould, M., Schurdi-Levraud, V., Decroocq, V., 2006. PPV long-distance movement is occasionally permitted in resistant apricot hosts. Virus Res. 120, 70-78.

Ivanov, P. A., Karpova, O. V., Skulachev, M. V., Tomashevskaya, O. L., Rodionova, N. P., Dorokhov, Y. L., Atabekov, J. G., 1997. A tobamovirus genome that contains an internal ribosome entry site functional in vitro. Virology 232, 32-43.

Karasev, A. V., 2000. Genetic diversity and evolution of closteroviruses. Annu. Rev. Phytopathol. 38, 293-324.

Karasev, A. V., Boyko, V. P., Gowda, S., Nikolaeva, O. V., Hilf, M. E., Koonin, E. V., Niblett, C. L., Cline, K., Gumpf, D. J., Lee, R. F., Garnsey, S. M., Lewandowski, D. J., Dawson, W. O., 1995. Complete sequence of the citrus tristeza virus RNA genome. Virology 208, 511-520.

Karasev, A. V., Nikolaeva, O. V., Mushegian, A. R., Lee, R. F. Dawson, W. O., 1996. Organization of the 3'-terminal half of beet yellow stunt virus genome and implications for the evolution of closteroviruses. J. Virol. 221, 199-207.

Kasschau, K. D., Xie, Z., Allen, E., Llave, C., Chapman, E. J., Krizan, K. A., and Carrington, J. C., 2003. P1/HC-Pro, a viral suppressor of RNA silencing, interferes with *Arabidopsis* development and miRNA function. Dev. Cell 4, 205-217.

Kawakami, S., Watanabe, Y., Beachy, R. N., 2004. Tobacco mosaic virus infection spreads cell to cell as intact replication complexes. Proc. Natl. Acad. Sci. USA 101, 6291-6296.

Kelloniemi, J., Makinen, K., Valkonen, J. P. T., 2008. Three heterologous proteins simultaneously expressed from a chimeric potyvirus: infectivity, stability and the correlation of genome and virion lengths. Virus Res. 135, 282-291.

Kneller, E. L., Rakotondrafara, A. M., Miller, W. A., 2006. Cap independent translation of plant viral RNAs. Virus Res. 119, 63-75.

Koh, D. C., Wong, S. M., Liu, D. X., 2003. Synergism of the 3'-untranslated region and an internal ribosome entry site differentially enhances the translation of a plant virus coat protein. J. Biol. Chem. 278, 20565-20573.

Lehto, K., and Dawson, W. O., 1990. Replication, stability, and gene expression of tobacco mosaic virus mutants with a second 30K ORF. Virology 175, 30-40.

Lewandowski, D. J. and Dawson, W. O., 1998. Deletion of internal sequences results in Tobacco mosaic virus defective RNAs that accumulate to high levels without interfering with replication of the helper virus. Virology 251, 427-437.

Lico, C., Chen, Q., Santi, L., 2008. Viral vectors for production of recombinant proteins in plants. J. Cell Physiol. 216, 366-377.

Liu, Y. P., Peremyslov, V. V., Medina, V., Dolja, V. V. 2009. Tandem leader proteases of Grapevine leafroll-associated virus 2: host-specific functions in the infection cycle. Virology 383, 291-299.

López, C., Navas-Castillo, J., Gowda, S., Moreno, P., Flores R., 2000. The 23-kDa protein coded by the 3'-terminal gene of *citrus tristeza* virus is an RNA-binding protein. Virology 269, 462-470.

Lu, R., Folimonov, A., Shintaku, M., Li, W. X., Falk, B. W., Dawson, W. O., Ding, S. W., 2004. Three distinct suppressors of RNA silencing encoded by a 20-kb viral RNA genome. Proc. Natl. Acad. Sci. USA 101, 15742-15747.

Lucy, A. P., Guo, H. S., $L_1$, W. X., Ding, S. W., 2000. Suppression of post-transcriptional gene silencing by a plant viral protein localized in the nucleus. EMBO J. 19, 1672-1680.

Marton, I., Zuker, A., Shklarman, E., Zeevi, V., Tovkach, A., Roffe, S., Ovadis, M., Tzfira, T., Vainstein, A., 2010. Nontransgenic genome modification in plant cells. Plant Physiol. 154, 1079-1087.

Masoumi, A., Hanzlik, T. N., Christian, P. D., 2003. Functionality of the 59- and intergenic IRES elements of cricket paralysis virus in a range of insect cell lines, and its relationship with viral activities. Virus Res. 94, 113-120.

Masuta, C., Yamana, T., Tacahashi, Y., Uyeda, I., Sato, M., Ueda, S., Matsumura, T., 2000. Development of clover yellow vein virus as an efficient, stable gene-expression system for legume species. Plant J. 23, 539-546.

Navas-Castillo, J., Albiach-MartôÂ, M. R., Gowda, S., Hilf, M. E., Garnsey, S. M., Dawson, W. O., 1997. Kinetics of accumulation of *citrus tristeza* virus RNAs. Virology 228, 92-97.

Niepel, M., Gallie, D. R., 1999. Identification and characterization of the functional elements within the tobacco etch virus 5' leader required for cap-independent translation. J. Virol. 73, 9080-9088.

Padgett, H. S., Epel, B. L., Heinlein, M. H., Watanabe, Y., Beachy, R. N. 1996. Distribution of tobamovirus movement protein in infected cells and implications for cell-to-cell spread of infection. Plant J. 10, 1079-1099.

Pappu, H. R., Karasev, A. V., Anderson, E. J., Pappu, S. S., Hilf, M. E., Febres, V. J., Eckloff, R. M. G., McCaffery, M., Boyko, V., Gowda, S., Dolia, V. V., Koonin, E. V., Gumpf, D. J., Cline, K. C., Garnsey, S. M., Dawson, W. O., Lee, R. F., Niblett, C. L., 1994. Nucleotide sequence and organization of eight 3' open reading frames of the *Citrus tristeza* closterovirus genome. Virology 199, 35-46.

Peremyslov, V. V., Hagiwara, Y., Dolja, V. V., 1999. HSP70 homolog functions in cell-to-cell movement of a plant virus. Proc. Natl. Acad. Sci. U.S.A. 96, 14771-14776.

Prokhnevsky, A. I., V. V. Peremyslov, V. V., Napuli, A. J., Dolja, V. V., 2002. Interaction between long-distance transport factor and Hsp70-related movement protein of beet yellows virus. J. Virol. 76, 11003-11011.

Ratcliff, F., MacFarlane, S., Baulcombe, D. C., 1999. Gene silencing without DNA: RNA-mediated cross protection between viruses. Plant Cell, 11, 1207-1215.

Roberts, A. G., Santa Cruz, S., Roberts, I. M., Prior, D. A. M., Turgeon, R., Oparka, K. J., 1997. Phloem unloading in sink leaves of *Nicotiana benthamiana*: comparison of a fluorescent solute with a fluorescent virus. Plant Cell 9, 1381-1396.

Roberts, L. O., Groppelli, E., 2009. An atypical IRES within the 50 UTR of a dicistrovirus genome. Virus Res. 139, 157-165.

Robertson, C. J., Garnsey, S. M., Satyanarayana, T., Folimonova, S., Dawson, W. O., 2005. Efficient infection of *citrus* plants with different cloned constructs of *Citrus tristeza* virus amplified in *Nicotiana benthamiana* protoplasts. Proc. 16th Conf. IOCV. IOCV, Riverside, Calif., pp. 187-195.

Roy, G., Weisburg, S., Rabindran, S., Yusibov, V., 2010. A novel two-component Tobacco mosaic virus-based vector system for high-level expression of multiple therapeutic proteins including a human monoclonal antibody in plants. Virology 405, 93-99.

Sánchez-Navarro, J. A., Miglino, R., Ragozzino, A., and Bol, J. F., 2001. Engineering of Alfalfa mosaic virus RNA 3 into an expression vector. Arch. Virol. 146, 923-939.

Sato, M., Masuta, C., Uyeda, I., 2003. Natural resistance to Clover yellow vein virus in beans controlled by a single recessive locus. Mol. Plant. Microbe Interact. 16, 994-1002.

Satyanarayana, T., Bar-Joseph, M., Mawassi, M., Albiach-Marti, M. R., Ayllón, M. A., Gowda, S., Hilf, M. E., Moreno, P., Garnsey, S. M., Dawson, W. O., 2001. Amplification of *Citrus tristeza* virus from a cDNA clone and infection of *citrus* trees. Virology 280, 87-96.

Satyanarayana, T., Gowda, S., Ayllón, M. A., Albiach-Martí, M. R., Dawson, W. O., 2002a. Mutational analysis of the replication signals in the 3'-non translated region of *Citrus tristeza* virus. Virology 300, 140-152.

Satyanarayana, T., Gowda, S., Ayllón, M. A., Albiach-Martí, M. R., Rabindram, R., Dawson, W. O. 2002b. The p23 protein of *Citrus tristeza* virus controls asymmetrical RNA accumulation. J. Virol. 76, 473-483.

Satyanarayana, T., Gowda, S., Ayllón, M. A., Dawson, W. O., 2003. Frame shift mutations in infectious cDNA clones of *Citrus tristeza* virus: a strategy to minimize the toxicity of viral sequences to *Escherichia coli*. Virology 313, 481-491.

Satyanarayana, T., Gowda, S., Ayllón, M. A., Dawson, W. O., 2004. Closterovirus bipolar virion: evidence for initiation of assembly by minor coat protein and its restriction to the genomic RNA 5' region. Proc. Natl. Acad. Sci. USA 101, 799-804.

Satyanarayana, T., Gowda, S., Boyko, V. P., Albiach-Marti, M. R., Mawassi, M., Navas-Castillo, J., Karasev, A. V., Dolja, V., Hilf, M. E., Lewandowski, D. J., Moreno, P., Bar-Joseph, M., Garnsey, S. M., Dawson, W. O., 1999. An engineered closterovirus RNA replicon and analysis of heterologous terminal sequences for replication. Proc. Natl. Acad. Sci. USA 96, 7433-7438.

Satyanarayana, T., Gowda, S., Mawassi, M., Albiach-Marti, M. R., Ayllón, M. A., Robertson, C., Garnsey, S. M., Dawson, W. O., 2000. Closterovirus encoded HSP70 homolog and p61 in addition to both coat proteins function in efficient virion assembly. Virology 278, 253-265.

Shivprasad, S., Pogue, G. P., Lewandowski, D. J., Hidalgo, J., Donson, J., Grill, L. K., Dawson, W. O., 1999. Heterologous sequences greatly affect foreign gene expression in tobacco mosaic virus-based vectors. Virology 255, 312-323.

Siegel, A., 1983. RNA viruses as cloning vehicles. Phytopathology 73,775.

Siegel, A., 1985. Plant-virus-based vectors for gene transfer may be of considerable use despite a presumed high error frequency during RNA synthesis. Plant Mol. Biol. 4, 327-29.

Takahashi, T., Sugawara, T., Yamatsuta, T., Isogai, M., Natsuaki, T., Yoshikawa, N., 2007. Analysis of the spatial distribution of identical and two distinct virus populations differently labeled with cyan and yellow fluorescent proteins in coinfected plants. Phytopathology 97, 1200-1206

Takamatsu, N., Ishikawa, M., Meshi, T., Okada, Y., 1987. Expression of bacterial chloramphenicol acetyl transferase gene in tobacco plants mediated by TMV-RNA. EMBO J. 6, 307-311.

Tatineni, S., Gowda, S., Dawson W. O., 2010. Heterologous minor coat proteins of *Citrus tristeza* virus strains affect encapsidation, but the coexpression of HSP70h and p61 restores encapsidation to wild-type levels. Virology 402, 262-270.

Tatineni, S., McMechan A. J., Hein G. L., French R., 2011. Efficient and stable expression of GFP through Wheat streak mosaic virus-based vectors in cereal hosts using a range of cleavage sites: Formation of dense fluorescent aggregates for sensitive virus tracking. Virology 410, 268-281.

Tatineni, S., Robertson, C. J., Garnsey, S. M., Bar-Joseph, M., Gowda, S., Dawson, W. O., 2008. Three genes of *Citrus tristeza* virus are dispensable for infection and movement throughout some varieties of *citrus* trees. Virology 376, 297-307.

Toth, R. L., Chapman, S., Carr, F., Santa Cruz, S., 2001. A novel strategy for the expression of foreign genes from plant virus vectors. FEBS Lett. 489, 215-219.

Turpen, T. H., Turpen, A. M., Weinzettl, N., Kumagai, M. H., Dawson, W. O., 1993. Transfection of whole plants from wounds inoculated with *Agrobacterium tumefaciens* containing cDNA of tobacco mosaic virus. J. Virol. Meth. 42, 227-239.

Van Vloten-Doting, L., 1983. Advantages of multiple partite genomes of single-stranded RNA plant viruses in nature, for research and genetic engineering. Plant Mol. Biol. 1, 55-60.

Van Vloten-Doting, L., Bol, J. F., Cornelissen, B., 1985. Plant virus-based vectors for gene transfer will be of limited use because of the high error frequency during viral RNA synthesis. Plant Mol. Biol. 4, 323-326.

Verch, T., Yusibov, V., Koprowski, H., 1998. Expression and assembly of a full-length monoclonal antibody in plants using a plant virus vector. J. Immunol. Methods 220, 69-75.

Verver, J., Wellink, J., Van Lent, J., Gopinath, K., and Van Kammen, A., 1998. Studies on the movement of cowpea mosaic virus using the jellyfish green fluorescent protein. Virology 242, 22-27.

Woolaway, K. E., Lazaridis, K., Belsham, G. J., Carter, M. J., Robert, L. O., 2001. The 5' untranslated region of rhopalosiphum padi virus contains an internal ribosome entry site which functions efficiently in mammalian, plant, and insect translation system. J. Virol. 75, 10244-10249.

While various disclosed embodiments have been described above, it should be understood that they have been presented by way of example only, and not limitation. Numerous changes to the subject matter disclosed herein can be made in accordance with this Disclosure without departing from the spirit or scope of this Disclosure. In addition, while a particular feature may have been disclosed with respect to only one of several implementations, such feature may be combined with one or more other features of the other implementations as may be desired and advantageous for any given or particular application.

Thus, the breadth and scope of the subject matter provided in this Disclosure should not be limited by any of the above explicitly described embodiments. Rather, the scope of this Disclosure should be defined in accordance with the following claims and their equivalents.

The terminology used herein is for the purpose of describing particular embodiments only and is not intended to be limiting. As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which embodiments belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The teachings of any patents, patent applications, technical or scientific articles or other references are incorporated herein in their entirety to the extent not inconsistent with the teachings herein.

What is claimed is:

1. A method of transfecting a *citrus* tree with a gene of interest having a 5' end and a 3' end, said method comprising inoculating said *citrus* tree with a sample comprising at least one *Citrus tristeza* virus (CTV) vector to produce an inoculated tree, said CTV vector engineered to comprise a construct comprising a heterologous gene of interest and a subgenomic RNA (sgRNA) heterologous controller element (CE) positioned upstream of the 5' end of said heterologous gene of interest so as to control expression of said heterologous gene of interest; and growing said inoculated tree under conditions to allow a systemic infection of said tree with said at least one CTV vector; wherein expression of said heterologous gene of interest occurs for two months or more in the tree with a majority of virus in the systemic infection comprising said CTV vector.

\* \* \* \* \*

SEQUENCE LISTING

<160> NUMBER OF SEQ ID NOS: 78

<210> SEQ ID NO 1
<211> LENGTH: 27
<212> TYPE: DNA
<213> ORGANISM: Tobacco etch virus

<400> SEQUENCE: 1
atgaaaactt acaatgttgg agggatg                                    27

<210> SEQ ID NO 2
<211> LENGTH: 9
<212> TYPE: PRT
<213> ORGANISM: Tobacco etch virus

<400> SEQUENCE: 2

Met Lys Thr Tyr Asn Val Gly Gly Met
1               5

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
atgaagacct ataacgtagg tggcatg                                    27

<210> SEQ ID NO 4
<211> LENGTH: 21
<212> TYPE: DNA
<213> ORGANISM: Tobacco etch virus

<400> SEQUENCE: 4
gagaatcttt attttcagag t                                          21

<210> SEQ ID NO 5
<211> LENGTH: 7
<212> TYPE: PRT
<213> ORGANISM: Tobacco etch virus

<400> SEQUENCE: 5

Glu Asn Leu Tyr Phe Gln Ser
1               5

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gaaaacctat acttccaatc g                                          21

<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
agtcctcgag aaccacttag ttgtttagct atc                                      33

<210> SEQ ID NO 8
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ttatgcggcc gcaggccttg gacctatgtt ggccccccat ag                            42

<210> SEQ ID NO 9
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
taatcgtact tgagttctaa tatggctagc aaaggagaag aa                            42

<210> SEQ ID NO 10
<211> LENGTH: 100
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gccgcactag tatttaaatc ccgtttcgtc ctttagggac tcgtcagtgt actgatataa         60
gtacagactg gacctatgtt ggccccccat agggacagtg                              100

<210> SEQ ID NO 11
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
atggatgagc tctacaaatg attgaagtgg acggaataag ttcc                          44

<210> SEQ ID NO 12
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ggaacttatt ccgtccactt caatcatttg tagagctcat ccat                          44

<210> SEQ ID NO 13
<211> LENGTH: 84
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gcacgttgtg ctatagtacg tgccataata gtgagtgcta gcaaagtata aacgctggtg    60
tttagcgcat attaaatact aacg                                          84

<210> SEQ ID NO 14
<211> LENGTH: 101
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cagcttgctt ctacctgaca cagttaagaa gcggcataaa tcgaagccaa accctaaatt    60
ttgcaactcg atcaattgta acctagagcg aagtgcaatc a                      101

<210> SEQ ID NO 15
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tttagcgcat attaaatact aacgatggct agcaaaggag aagaa                    45

<210> SEQ ID NO 16
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
actgtgtcag gtagaagcaa gctgtcagat gaagtggtgt tcacg                    45

<210> SEQ ID NO 17
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ttggatttag gtgacactat agtggaccta tgttggcccc ccata                    45

<210> SEQ ID NO 18
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gtaacctaga gcgaagtgca atcaatggct agcaaaggag aagaa                    45

<210> SEQ ID NO 19
<211> LENGTH: 86
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 19
gcctaagctt acaaatactc ccccacaaca gcttacaata ctcccccaca cagcttacaa    60
atactccccc acaacagctt gtcgac                                        86

<210> SEQ ID NO 20
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ctccgtgaac accacttcat ctgaaaataa caaatctcaa cacaa                   45

<210> SEQ ID NO 21
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ttgtgttgag atttgttatt ttcagatgaa gtggtgttca cggag                   45

<210> SEQ ID NO 22
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ggagtatttg taagcttagg ctcagatgaa gtggtgttca cggag                   45

<210> SEQ ID NO 23
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ccccacaaca gcttgtcgac atggctagca aaggagaaga acttt                   45

<210> SEQ ID NO 24
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
cgtgaacacc acttcatctg attcgacctc ggtcgtctta gttaa                   45

<210> SEQ ID NO 25
<211> LENGTH: 45
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 25
ttaactaaga cgaccgaggt cgaatcagat gaagtggtgt tcacg          45

<210> SEQ ID NO 26
<211> LENGTH: 137
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ggcgatcacg acagagccgt gtcaattgtc gcggctaaga atgctgtgga tcgcagcgct    60
ttcactggag gggagagaaa aatagttagt ttgtatgcct taggaaggaa ctaagcacgt   120
tgtgctatag tacgtgc                                                 137

<210> SEQ ID NO 27
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tgacacggct ctgtcgtgat cgcctcagat gaagtggtgt tcacg          45

<210> SEQ ID NO 28
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gccacctacg ttataggtct tcattttgta gagctcatcc atgcc          45

<210> SEQ ID NO 29
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
aagacctata acgtaggtgg catgaaggct caatattcgg atcta          45

<210> SEQ ID NO 30
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
atgaaaactt acaatgttgg agggatgtta cgtcctgtag aaacc          45
```

<210> SEQ ID NO 31
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ggtttctaca ggacgtaaca tccctccaac attgtaagtt ttcat            45

<210> SEQ ID NO 32
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ccgcagcagg gaggcaaaca atgattgaag tggacggaat aagtt            45

<210> SEQ ID NO 33
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
aacttattcc gtccacttca atcattgttt gcctccctgc tgcgg            45

<210> SEQ ID NO 34
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
cttactctga aaataaagat tctctttgta gagctcatcc atgcc            45

<210> SEQ ID NO 35
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
aaagagaatc tttattttca gagtaaggga ccacgtgatt acaac            45

<210> SEQ ID NO 36
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
cgattggaag tataggtttt cttgcgagta caccaattca ctcat            45

<210> SEQ ID NO 37

```
<210> SEQ ID NO 37
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
caagaaaacc tatacttcca atcgatgtta cgtcctgtag aaacc          45

<210> SEQ ID NO 38
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gtcactttgt ttagcgtgac ttagcagctt gcttctacct gacac          45

<210> SEQ ID NO 39
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gtgtcaggta gaagcaagct gctaagtcac gctaaacaaa gtgac          45

<210> SEQ ID NO 40
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
ttagtctctc catcttgcgt gtagcagctt gcttctacct gacac          45

<210> SEQ ID NO 41
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gtgtcaggta gaagcaagct gctacacgca agatggagag actaa          45

<210> SEQ ID NO 42
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
atggatgagc tctacaaatg agtttcagaa attgtcgaat cgcat          45

<210> SEQ ID NO 43
<211> LENGTH: 45
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
atgcgattcg acaatttctg aaactcattt gtagagctca tccat            45

<210> SEQ ID NO 44
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
atggatgagc tctacaaatg agttaatacg cttctcagaa cgtgt            45

<210> SEQ ID NO 45
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
acacgttctg agaagcgtat taactcattt gtagagctca tccat            45

<210> SEQ ID NO 46
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
tttagcgcat attaaatact aacgatgtac ccatacgatg ttcca            45

<210> SEQ ID NO 47
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
tggaacatcg tatgggtaca tcgttagtat ttaatatgcg ctaaa            45

<210> SEQ ID NO 48
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
actgtgtcag gtagaagcaa gctgttactt gtacagctcg tccat            45

<210> SEQ ID NO 49
<211> LENGTH: 45
<212> TYPE: DNA
```

<213> ORGANISM: Artificial Sequence
<220> FEATURE:
<223> OTHER INFORMATION: Description of Artificial Sequence: Synthetic primer

<400> SEQUENCE: 49
gtaacctaga gcgaagtgca atcaatggac tacaaagacg atgac     45

<210> SEQ ID NO 50
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 50
gtcactttgt ttagcgtgac ttagggcgat cacgacagag ccgtg     45

<210> SEQ ID NO 51
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 51
cacggctctg tcgtgatcgc cctaagtcac gctaaacaaa gtgac     45

<210> SEQ ID NO 52
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 52
gtcactttgt ttagcgtgac ttagttcgac ctcggtcgtc ttagt     45

<210> SEQ ID NO 53
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 53
actaagacga ccgaggtcga actaagtcac gctaaacaaa gtgac     45

<210> SEQ ID NO 54
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 54
cacaacgtct atatcatggc ctaggtttca gaaattgtcg aatcg     45

<210> SEQ ID NO 55
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
cgattcgaca atttctgaaa cctaggccat gatatagacg ttgtg         45

<210> SEQ ID NO 56
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
ggcatggacg agctgtacaa gtaattgaag tggacggaat aagtt         45

<210> SEQ ID NO 57
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
aacttattcc gtccacttca attacttgta cagctcgtcc atgcc         45

<210> SEQ ID NO 58
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
tcgctcttac cttgcgataa ctagcagctt gcttctacct gacac         45

<210> SEQ ID NO 59
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
gtaacctaga gcgaagtgca atcaatgtta cgtcctgtag aaacc         45

<210> SEQ ID NO 60
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
ggtttctaca ggacgtaaca ttgattgcac ttcgctctag gttacaa         47

<210> SEQ ID NO 61
<211> LENGTH: 45
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 61
ccgcagcagg gaggcaaaca atgagtttca gaaattgtcg aatcg              45

<210> SEQ ID NO 62
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
cgattcgaca atttctgaaa ctcattgttt gcctccctgc tgcgg              45

<210> SEQ ID NO 63
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
gtgtcaggta gaagcaagct gctagttatc gcaaggtaag agcga              45

<210> SEQ ID NO 64
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
atggatgagc tctacaaatg aagtctactc agtagtacgt ctatt              45

<210> SEQ ID NO 65
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
aatagacgta ctactgagta gacttcattt gtagagctca tccat              45

<210> SEQ ID NO 66
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
gcggatgcat tatttggttt tacaacaacg gtacgtttca aaatg              45

<210> SEQ ID NO 67
<211> LENGTH: 45
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 67
atgaaaactt acaatgttgg agggatggct agcaaaggag aagaa         45

<210> SEQ ID NO 68
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
ttcttctcct tgctagcca tccctccaac attgtaagtt ttcat         45

<210> SEQ ID NO 69
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
gagaatcttt attttcagag taagggacca cgtgattaca acc         43

<210> SEQ ID NO 70
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
gaaaacctat acttccaatc gatggctagc aaaggagaag aact         44

<210> SEQ ID NO 71
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
agttcttctc ctttgctagc catcgattgg aagtataggt tttc         44

<210> SEQ ID NO 72
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
aagacctata acgtaggtgg catgaaggga ccacgtgatt acaac         45

<210> SEQ ID NO 73
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

```
<210> SEQ ID NO 73
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
ccctccaaca ttgtaagttt tcatttgcga gtacaccaat tcact              45

<210> SEQ ID NO 74
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
gagaatcttt attttcagag taaggctcaa tattcggatc taaag              45

<210> SEQ ID NO 75
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
cgattggaag tataggtttt cttcggattc caaacctgaa tgaac              45

<210> SEQ ID NO 76
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
gccacctacg ttataggtct tcatgatgaa gtggtgttca cggag              45

<210> SEQ ID NO 77
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
actctgaaaa taaagattct cgatgaagtg gtgttcacgg agaac              45

<210> SEQ ID NO 78
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
catttacgaa cgatagccat ggctagcaaa ggagaagaa                     39
```